United States Patent
Iversen et al.

(10) Patent No.: US 9,572,899 B2
(45) Date of Patent: *Feb. 21, 2017

(54) COMPOSITIONS FOR ENHANCING TRANSPORT OF MOLECULES INTO CELLS

(75) Inventors: Patrick L. Iversen, Corvallis, OR (US); Hong M. Moulton, Corvallis, OR (US); Michelle H. Nelson, Corvallis, OR (US); Andrew D. Kroeker, Corvallis, OR (US); David A. Stein, Corvallis, OR (US)

(73) Assignee: AVI BIOPHARMA, INC., Corvallis, OR (US)

( * ) Notice: Subject to any disclaimer, the term of this patent is extended or adjusted under 35 U.S.C. 154(b) by 209 days.

This patent is subject to a terminal disclaimer.

(21) Appl. No.: 12/265,499

(22) Filed: Nov. 5, 2008

(65) Prior Publication Data

US 2009/0082547 A1    Mar. 26, 2009

Related U.S. Application Data

(63) Continuation of application No. 10/836,804, filed on Apr. 29, 2004, now Pat. No. 7,468,418.

(60) Provisional application No. 60/466,703, filed on Apr. 29, 2003.

(51) Int. Cl.
| | |
|---|---|
| *A61K 38/10* | (2006.01) |
| *C07K 4/00* | (2006.01) |
| *A61K 38/08* | (2006.01) |
| *C07H 21/02* | (2006.01) |
| *A61K 49/00* | (2006.01) |
| *A61K 47/48* | (2006.01) |
| *C12N 15/113* | (2010.01) |
| *C12N 15/87* | (2006.01) |

(52) U.S. Cl.
CPC ..... *A61K 49/0056* (2013.01); *A61K 47/48246* (2013.01); *A61K 49/0043* (2013.01); *A61K 49/0054* (2013.01); *C12N 15/113* (2013.01); *C12N 15/87* (2013.01); *C12N 2310/11* (2013.01); *C12N 2310/314* (2013.01); *C12N 2310/3233* (2013.01); *C12N 2310/3513* (2013.01); *C12N 2320/32* (2013.01)

(58) Field of Classification Search
None
See application file for complete search history.

(56) References Cited

U.S. PATENT DOCUMENTS

| | | | | |
|---|---|---|---|---|
| 5,087,617 | A | * 2/1992 | Smith | 514/44 A |
| 5,525,465 | A | * 6/1996 | Haralambidis et al. | 435/6 |
| 5,686,564 | A | * 11/1997 | Brundish et al. | 530/327 |
| 5,747,641 | A | 5/1998 | Frankel et al. | |
| 5,849,727 | A | 12/1998 | Porter et al. | |
| 6,159,946 | A | 12/2000 | Zalewski et al. | |
| 6,303,573 | B1 | 10/2001 | Ruoslahti et al. | |
| 6,306,993 | B1 | * 10/2001 | Rothbard | A61K 31/785 514/1.2 |
| 6,365,351 | B1 | 4/2002 | Iversen | |
| 6,495,663 | B1 | 12/2002 | Rothbard et al. | |
| 6,559,279 | B1 | * 5/2003 | Manoharan et al. | 530/322 |
| 6,593,292 | B1 | * 7/2003 | Rothbard et al. | 514/1.2 |
| 6,645,974 | B2 | 11/2003 | Hutchinson et al. | |
| 6,669,951 | B2 | 12/2003 | Rothbard et al. | |
| 7,138,238 | B2 | 11/2006 | Vodyanoy et al. | |
| 7,169,814 | B2 | 1/2007 | Rothbard et al. | |
| 7,456,146 | B2 | 11/2008 | Yu et al. | |
| 7,468,418 | B2 | 12/2008 | Iversen et al. | |
| 7,482,016 | B2 | 1/2009 | Doerr et al. | |
| 7,507,196 | B2 | 3/2009 | Stein et al. | |
| 7,524,829 | B2 | 4/2009 | Stein et al. | |
| 7,582,615 | B2 | 9/2009 | Neuman et al. | |
| 7,585,834 | B2 | 9/2009 | Wender et al. | |
| 7,786,151 | B2 | 8/2010 | Hagiwara et al. | |
| 7,790,694 | B2 | 9/2010 | Geller et al. | |
| 7,855,283 | B2 | 12/2010 | Iversen | |
| 7,888,012 | B2 | 2/2011 | Iversen et al. | |
| 7,943,762 | B2 | 5/2011 | Weller et al. | |
| 7,973,015 | B2 | 7/2011 | van Ommen et al. | |
| 7,989,608 | B2 | 8/2011 | Mourich et al. | |
| 8,008,469 | B2 | 8/2011 | Mourich et al. | |
| 8,030,291 | B2 | 10/2011 | Stein et al. | |
| 8,030,292 | B2 | 10/2011 | Stein et al. | |
| 8,067,571 | B2 | 11/2011 | Weller et al. | |

(Continued)

FOREIGN PATENT DOCUMENTS

| | | |
|---|---|---|
| EP | 1 938 802 A1 | 7/2008 |
| JP | 2002-511885 A | 4/2002 |

(Continued)

OTHER PUBLICATIONS

Chen et al (Bioconj. Chem. 14: 532-538, 2003).*
Rothbard et al ( J. Med. Chem. 45: 3612-3619, 2002).*
Arora et al (J. Pharm. Sci. 91(4) : 1009-1018).*
Moulton et al (Bioconj. Chem. 15: 290-299, 2004).*
Gen Bank XP_001635778.*
Dapic, V. et al., "Biophysical and biological properties of quadruplex oligodeoxyribonucleotides", *Nucleic Acids Research*, 31(8):2097-2107 (2003).

(Continued)

*Primary Examiner* — Richard Schnizer
(74) *Attorney, Agent, or Firm* — Brian C. Trinque; Lathrop & Gage LLP

(57) ABSTRACT

Compositions and methods for enhancing delivery of molecules, e.g. biological agents, into cells are described. The composition is a conjugate of the biological agent, preferably a nucleic acid analog having a substantially uncharged backbone, covalently linked to a peptide transporter moiety as described. Conjugation of the peptide transporter to a substantially uncharged nucleic acid analog, such as a morpholino oligomer, is also shown to enhance binding of the oligomer to its target sequence and enhance antisense activity.

22 Claims, 30 Drawing Sheets

(56) References Cited

U.S. PATENT DOCUMENTS

| | | | |
|---|---|---|---|
| 8,084,433 B2 | 12/2011 | Iversen et al. | |
| 8,129,352 B2 | 3/2012 | Iversen et al. | |
| 8,168,604 B2 | 5/2012 | Stein et al. | |
| 8,835,402 B2 | 9/2014 | Kole et al. | |
| 8,865,883 B2 | 10/2014 | Sazani et al. | |
| 8,871,918 B2 | 10/2014 | Sazani et al. | |
| 9,068,185 B2 | 6/2015 | Iversen | |
| 2001/0021700 A1* | 9/2001 | Moore et al. | 514/44 |
| 2002/0045736 A1* | 4/2002 | Yu et al. | 530/389.1 |
| 2002/0127198 A1* | 9/2002 | Rothbard et al. | 424/78.37 |
| 2003/0022831 A1* | 1/2003 | Rothbard et al. | 514/12 |
| 2003/0031655 A1* | 2/2003 | Woolf | 424/93.21 |
| 2003/0032593 A1 | 2/2003 | Wender et al. | |
| 2003/0040466 A1 | 2/2003 | Vodyanoy et al. | |
| 2003/0045488 A1 | 3/2003 | Brown et al. | |
| 2003/0087861 A1 | 5/2003 | Iversen | |
| 2003/0185788 A1 | 10/2003 | Rothbard et al. | |
| 2003/0228348 A1 | 12/2003 | Hirayama et al. | |
| 2003/0235845 A1 | 12/2003 | Van Ommen et al. | |
| 2004/0170955 A1 | 9/2004 | Arap et al. | |
| 2004/0247614 A1 | 12/2004 | Dorr et al. | |
| 2005/0171026 A1 | 8/2005 | Hagiwara et al. | |
| 2006/0014712 A1 | 1/2006 | Neuman | |
| 2006/0078542 A1 | 4/2006 | Mah et al. | |
| 2006/0127981 A1 | 6/2006 | Bergman et al. | |
| 2006/0148747 A1 | 7/2006 | Stein et al. | |
| 2006/0276425 A1 | 12/2006 | Mourich et al. | |
| 2007/0004661 A1 | 1/2007 | Stein et al. | |
| 2007/0066556 A1 | 3/2007 | Stein et al. | |
| 2007/0129323 A1 | 6/2007 | Stein et al. | |
| 2007/0135333 A1 | 6/2007 | Geller et al. | |
| 2007/0265214 A1 | 11/2007 | Stein et al. | |
| 2008/0182973 A1 | 7/2008 | Iversen et al. | 530/358 |
| 2008/0267978 A1 | 10/2008 | Zutter | |
| 2009/0075377 A1 | 3/2009 | Lu et al. | |
| 2009/0082547 A1 | 3/2009 | Iversen et al. | |
| 2009/0088562 A1 | 4/2009 | Weller et al. | |
| 2009/0099066 A1 | 4/2009 | Moulton et al. | |
| 2009/0110689 A1 | 4/2009 | Mourich et al. | |
| 2009/0180958 A1 | 7/2009 | Koivistoinen et al. | |
| 2009/0318676 A1 | 12/2009 | Manoharan et al. | |
| 2010/0016215 A1 | 1/2010 | Moulton et al. | |
| 2010/0021456 A1 | 1/2010 | Miossec et al. | |
| 2010/0063133 A1 | 3/2010 | Neuman et al. | |
| 2010/0130591 A1 | 5/2010 | Sazani et al. | |
| 2010/0184670 A1 | 7/2010 | Mourich et al. | |
| 2010/0184833 A1 | 7/2010 | De Kimpe et al. | |
| 2010/0190689 A1 | 7/2010 | Thornton et al. | |
| 2010/0234280 A1 | 9/2010 | Geller et al. | |
| 2010/0234281 A1 | 9/2010 | Weller et al. | |
| 2011/0118334 A1 | 5/2011 | Iversen | |
| 2011/0269665 A1 | 11/2011 | Kole | |
| 2011/0289608 A1 | 11/2011 | Schnell et al. | |
| 2011/0306550 A1 | 12/2011 | Vitek et al. | |
| 2012/0058946 A1 | 3/2012 | Moulton et al. | |
| 2012/0141463 A1 | 6/2012 | Wu et al. | |
| 2012/0148622 A1 | 6/2012 | tenOever | |
| 2012/0289457 A1 | 11/2012 | Hanson | |
| 2013/0005792 A1 | 1/2013 | Haining et al. | |
| 2013/0045202 A1 | 2/2013 | Irving et al. | |
| 2013/0089517 A1 | 4/2013 | Brady et al. | |
| 2013/0131312 A1 | 5/2013 | Iversen et al. | |
| 2015/0080311 A1 | 3/2015 | Moulton et al. | |
| 2015/0141321 A1 | 5/2015 | Kole et al. | |
| 2015/0152415 A1 | 6/2015 | Sazani et al. | |

FOREIGN PATENT DOCUMENTS

| | | |
|---|---|---|
| JP | 2007-536253 A | 12/2007 |
| JP | 2011-505846 A | 3/2011 |
| WO | 9404686 A1 | 3/1994 |
| WO | WO 00/44897 A1 | 8/2000 |
| WO | WO 00/71706 A1 | 11/2000 |
| WO | WO 01/62297 A1 | 8/2001 |
| WO | 02/38764 A2 | 5/2002 |
| WO | WO 03/068942 A2 | 8/2003 |
| WO | 2004/097017 A2 | 11/2004 |
| WO | 2005/010044 A2 | 2/2005 |
| WO | 2005/030799 A1 | 4/2005 |
| WO | 2005/072527 A2 | 8/2005 |
| WO | 2005/089247 A2 | 9/2005 |
| WO | 2005/115479 A2 | 12/2005 |
| WO | 2006/000057 A1 | 1/2006 |
| WO | 2006/033933 A2 | 3/2006 |
| WO | 2006/047683 A2 | 5/2006 |
| WO | 2006/050414 A2 | 5/2006 |
| WO | 2006/083183 A1 | 8/2006 |
| WO | 2006/086667 A2 | 8/2006 |
| WO | 2006/088833 A2 | 8/2006 |
| WO | 2007/009094 A2 | 1/2007 |
| WO | 2007/030576 A2 | 3/2007 |
| WO | 2007/030691 A2 | 3/2007 |
| WO | 2007/056466 A2 | 5/2007 |
| WO | 2007/103529 A2 | 9/2007 |
| WO | 2008/005002 A1 | 1/2008 |
| WO | 2008/008113 A1 | 1/2008 |
| WO | 2008/025025 A2 | 2/2008 |
| WO | 2008/036127 A2 | 3/2008 |
| WO | 2009/005793 A2 | 1/2009 |
| WO | 2009/026412 A1 | 2/2009 |
| WO | 2009/086469 A2 | 7/2009 |
| WO | 2009/144481 A2 | 12/2009 |
| WO | 2010/048586 A1 | 4/2010 |
| WO | 2010/054267 A1 | 5/2010 |
| WO | 2010/080554 A1 | 7/2010 |
| WO | 2011/143608 A1 | 11/2011 |

OTHER PUBLICATIONS

Devi, G., "Prostate cancer: status of current treatments and emerging antisense-based therapies", Current Opinion Therapies, 4(2):138-148 (2002).

Hudziak, R. et al., "Resistance of morpholino phosphorodiamidate oligomers to enzymatic degradation", Antisense Nucleic Acid Drug Dev., 6:267-272 (1996).

Kang, S-H. et al., "Up-regulation of luciferase gene expression with antisense oligonucleotides: implications and applications in functional assay development", Biochemistry, 37(18):6235-6239 (1998).

Knapp, D. et al., "Resistance to chemotherapeutic drugs overcome by c-Myc inhibition in a Lewis lung carcinoma murine model.", Anticancer Drugs, 14(1):39-47 (2003).

Mizutani, M. et al., "Enhancement of sensitivity of urinary bladder tumor cells to cisplatin by c-myc antisense oligonucleotide", Cancer, 74(9):2546-2554 (1994).

Moulton, H. et al., "Cellular uptake of antisense morpholino oligomers conjugated to arginine-rich peptides", Bioconjugate Chemistry, 15:290-299 (2004).

Shafer, R. and Smirnov, I., "Biological aspects of DNA/RNA quadruplexes", Biopolymers, 56(3):209-27 (2000).

Stein, D. et al., "Inhibition of Vesivirus infections in mammalian tissue culture with antisense morpholino oligomers", Antisense Nucleic Acid Drug Dev., 11(5):317-325 (2001).

Summerton, J. and Weller, D., "Morpholino Antisense Oligomers: Design, Preparation, and Properties", Antisense Nucleic Acid Drug Dev., 7:187-195 (1997).

Vanin, E. and Ji, T., "Synthesis and application of cleavable photoactivable heterobifunctional reagents", Biochemistry, 20(24):6754-6760 (1981).

Alter et al., "Systemic delivery of morpholino oligonucleotide restores dystrophin expression bodywide and improves dystrophic pathology", Nature Medicine, 12(2):175-7 (2006).

Burrer et al., "Antiviral effects of antisense morpholino oligomers in murine coronavirus infection models", Journal of Virology, 81(11):5637-5648 (2007).

EMBL/GenBank/DDBJ database (Deshazer) May 26, 2007 Sequence CH899747. Retrieved from the Internet URL,:http://www.ebi.ac.uk/sgi-bin/emblfetch?style+html&id+CH899747> 196 pages (2007).

(56) References Cited

OTHER PUBLICATIONS

Gebski et al., "Morpholino antisense oligonucleotide induced dystrophin exon 23 skipping in mdx mouse muscle", *Human Molecular Genetics*, 12(15):1801-11 (2003).

Jearawiriyapaisarn, N. et al., "Sustained Dystrophin Expression Induced by Peptide-conjugated Morpholino Oligomers in the Muscles of mdx Mice.", *Mol. Therapy*, 16(9):1624-1629 (2008).

Kolonin et al., "Synchronous selection of homing peptides for multiple tissues by in vivo phage display", *The FASEB Journal*, 20(7):979-81 (2006).

Meade, B.R. and Dowdy, S.F., "Exogenous siRNA delivery using peptide transduction domains/cell penetrating peptides", *Advanced Drug Delivery Reviews*, 59(2-3):134-40 (2007).

Samoylova, T.I. and Smith, B.F., "Elucidation of muscle-binding peptides by phage display screening", *Muscle & Nerve*, 22(4):460-6 (1999).

Wu, R.P., D.S. Youngblood et al. (2007). "Cell-penetrating peptides as transporters for morpholino oligomers: effects of amino acid composition on intracellular delivery and cytotoxicity." Nucleic Acids Res. 35(15):5182-91. (Epub Aug. 1, 2007).

Youngblood et al., "Stability of cell-penetrating peptide-morpholino oligomer conjugates in human serum and in cells", *Bioconjugate Chemistry*, 18(1):50-60 (2007).

Abes et al., "Vectorization of morpholino oligomers by the (R-Ahx-R)4 peptide allows efficient splicing correction in the absence of endosomolytic agents", *Journal of Controlled Release*, 116(3):304-13 (2006).

Abes et al., "Arginine-rich cell penetrating peptides: design, structure-activity, and applications to alter pre-mRNA splicing by steric-block oligonucleotides", *Journal of Peptide Science*, 14:455-460 (2008).

Arora et al., "Bioavailability and efficacy of antisense morpholino oligomers targeted to c-myc and cytochrome P-450 3A2 following oral administration in rats", *J. Pharm Sci.*, 91(4):1009-1018 (2002).

Chen, C.P. et al., "A concise method for the preparation of peptide and arginine-rich peptide-conjugated antisense oligonucleotide", *Bioconjugate Chemistry*, 14:532-538 (2003).

International Search Report from PCT Application No. PCT/US2004/013660, search report dated Feb. 21, 2005, 5 pages (2005).

Eriksson, M. et al.,"Cell permeabilization and uptake of antisense peptide-peptide nucleic acid (PNA) into *Escherichia coli*", *The Journal of Biological Chemistry*,277(9):7144-7147 (2002).

Ghosh, C. and Iversen, P., "Intracellular delivery strategies for antisense phosphorodiamidate morpholino oligomers", *Antisense & Nucleic Acid Drug Development* 10:263-274 (2000).

Iversen, P., "Phosphorodiamidate morpholino oligomers: favorable properties for sequence-specific gene inactivation", *Current Opinion in Molecular Therapeutics* 3(3):235-238 (2001).

Lebleu, B. et al., "Cell penetrating peptide conjugates of steric block oligonucleotides", *Advanced Drug Delivery Reviews*, 60:517-529 (2008).

Marshall, N.B. et al., "Arginine-rich cell-penetrating peptides facilitate delivery of antisense oligomers into murine leukocytes and alter pre-mRNA splicing", *Journal of Immunological Methods*, 325:114-126 (2007).

Moulton, H. et al., "HIV Tat peptide enhances cellular delivery of antisense morpholino oligomers", *Antisense and Nucleic Acid Drug Development* , 13(1):31-43 (2003).

Richard, Jean Philippe et al., "Cell-penetrating peptides. A reevaluation of the mechanism of cellular uptake", *The Journal of Biological Chemistry*, 278(1):585-590, 2003.

Rothbard, J. et al., "Arginine-rich molecular transporters for drug delivery: role of backbone spacing in cellular uptake", *J. Med. Chem.* 45:3612-3618 (2002).

Wender, P. et al., "Oligocarbamate molecular transporters: design, synthesis, and biological evaluation of a new class of transporters for drug delivery", *J. Am. Chem. Soc.* 124:13382-13383, 2002.

Wender P. et al., "The design, synthesis, and evaluation of molecules that enable or enhance cellular uptake: peptoid molecular transporters", *Proc. Natl. Acad. Sci. USA*, 97(24):13003-13008 (2000).

Zubin, E. et al., "Oligonucleotide-peptide conjugates as potential antisense agents", *FEBS Letters*, 456(1):59-62 (1999).

Astriab-Fisher et al., "Antisense Inhibition of P-glycoprotein Expression Using Peptide-Oligonucleotide Conjugates," Biochemical Pharmacology 60:83-90, 2000.

Astriab-Fisher et al., "Conjugates of Antisense Oligonucleotides with the Tat and Antennapedia Cell-Penetrating Peptides: Effects on Cellular Uptake, Binding to Target Sequences, and Biologic Actions," Pharmaceutical Research 19(6):744-754, 2002.

Mourich et al., "Antisense compound and method for selectively killing activated T cells," U.S. Appl. No. 60/505,418, filed Sep. 23, 2003, 60 pages.

Yoo et al., "PAMAM Dendrimers as Delivery Agents for Antisense Oligonucleotides," Pharmaceutical Research 16 (12):1799-1804, 1999.

Written Opinion for PCT/US2004/013660, dated Feb. 21, 2005, 7 pages.

International Preliminary Examination Report for PCT/US2004/013660, dated Nov. 4, 2005, 8 pages.

International Preliminary Report on Patentability for International Application No. PCT/US2005/018213, mailed Oct. 23, 2007, 7 pages.

International Search Report for International Application No. PCT/US2005/018213, mailed Sep. 26, 2007, 2 pages.

Written Opinion of the International Searching Authority for International Application No. PCT/US2005/018213, mailed Sep. 26, 2007, 6 pages.

Vivès et al., "TAT Peptide Internalization: Seeking the Mechanism of Entry," *Current Protein and Peptide Science* 4:125-132, 2003.

International Preliminary Report on Patentability for corresponding International Application No. PCT/US2008/008168, dated Oct. 12, 2009, 10 pgs.

International Search Report and Written Opinion, mailed Mar. 19, 2009, for PCT/US08/08168, 9 pages.

PubChem (online), 6-Aminocaproic Acid—Compound Summary (CID 5460263), retrieved from URL=http://pubchem.ncbi.nlm.nih.gov/summary/summary.cgi?cid=5460263&loc=ec_rcs, download date Jun. 3, 2010, 3 pages.

Abes et al., "Delivery of steric block morpholino oligomers by (R-X-R)4 peptides: structure-activity studies," *Nucleic Acids Research* 36(20): 6343-6354, 2008.

Carlson et al., "In vitro-differentiated TH17 cells mediate lethal acute graft-versus-host disease with severe cutaneous and pulmonary pathologic mainifestations," *Blood* 113(6): 1365-1374, 2009.

Derossi et al., "Trojan peptides: the penetratin system for intracellular delivery," *Trends in Cell Biology* 8(2):84-87, 1998.

Devi et al , "Inhibition of Human Chorionic Gonadotropin β-Subunit Modulates the Mitogenic Effect of c-*myc* in Human Prostate Cancer Cells," *The Prostate* 53:200-210, 2002.

Egholm et al., "PNA hybridizes to complementary oligonucleotides obeying the Watson-Crick hydrogen-bonding rules," *Nature* 365:566-568, 1993.

Heineke et al., "Genetic Deletion of Myostatin From the Heart Prevents Skeletal Muscle Atrophy in Heart Failure," *Circulation* 121:419-425, 2010.

Iversen, "Phosphorodiamidate morpholino oligomers: Favorable properties for sequence-specific gene inactivation," *Current Opinion in Molecular Therapeutics* 3(3):235-238, 2001.

Matsui et al., "Protein Therapy: In Vivo Protein Transduction by Polyarginine (11R) PTD and Subcellular Targeting Delivery," *Current Protein and Peptide Science* 4:151-157, 2003.

Moskophidis et al., "Resistance of Lymphocytic Choriomeningitis Virus to Alpha/Beta Interferon and to Gamma Interferon," *Journal of Virology* 68(3):1951-1955, Mar. 1994.

Moskophidis et al., "Role of virus and host variables in virus persistence or immunopathological disease caused by a non-cytolytic virus," *Journal of General Virology* 76:381-391, 1995.

Nasevicius et al., "Effective targeted gene 'knockdown' in zebrafish," *Nature Genetics* 26:216-220, Oct. 2000.

Park et al., "Peroxisome Proliferator-Activated Receptor γ Agonist Down-Regulates IL-17 Expression in a Murine Model of Allergic Airway Inflammation," *The Journal of Immunology* 183:3259-3267, 2009.

(56) References Cited

OTHER PUBLICATIONS

Qin et al., "In Vivo Evaluation of a Morpholino Antisense Oligomer Directed Against Tumor Necrosis Factor-α," *Antisense & Nucleic Acid Drug Development 10*:11-16, 2000.

Rangachari et al., "T-bet negatively regulates autoimmune myocarditis by suppressing local production of interleukin 17," *The Journal of Experimental Medicine 203*(8):2009-2019, 2006.

Ricker et al., "*c-myc* antisense oligonucleotide treatment ameliorates murine ARPKD," *Kidney International 61*:S125-S131, 2002.

Spence et al., "Generation of cellular immunity to lymphocytic choriomeningitis virus is independent of CD1d1 expression," *Immunology 104*:168-174, 2001.

Stein et al., "Inhibition of Vesivirus Infections in Mammalian Tissue Culture with Antisense Morpholino Oligomers," *Antisense & Nucleic Acid Drug Development 11*(5)267-272, 1996.

Summerton, "Morpholino antisense oligomers: the case for an RNase H-independent structural type," *Biochimica et Biophysica Acta 1489*:141-158, 1999.

Wright et al., "The Human IL-17F/IL-17A Heterodimeric Cytokine Signals through the IL-17RA/IL-17RC Receptor Complex," *The Journal of Immunology 181*:2799-2805, 2008.

Yauch et al., "Mouse models of dengue virus infection and disease," *Antiviral Research 80*:87-93, 2008.

Yin et al., "Effective Exon Skipping and Restoration of Dystrophin Expression by Peptide Nucleic Acid Antisense Oligonucleotides in *mdx* Mice," *Molecular Therapy 16*(1):38-45, Jan. 2008.

Zhang et al., "Construction of a novel chimera consisting of a chelator-containing Tat peptide conjugated to a morpholino antisense oligomers for technetium-99m labeling and accelerating cellular kinetics," *Nuclear Medicine and Biology 33*:263-269, 2006.

Zhou et al., "IL-17A versus IL-17F induced intracellular signal transduction pathways and modulation by IL-17RA and IL-17RC RNA interference in AGS gastric adenocarcinoma cells," *Cytokine 38*:157-164, 2007.

Andreasen et al., "Expression and Functional Importance of Collagen-Binding Integrins, α2β1 and α2β1, on Virus-Activated T Cells," *The Journal of Immunology 171*:2804-2811, 2003.

Blattman et al., "Therapeutic use of IL-2 to enhance antiviral T-cell responses in vivo," *Nature Medicine 9*(5):540-547, May 2003.

Ge et al., "Inhibition of Multiple Subtypes of Influenza A Virus in Cell Cultures with Morpholino Oligomers," *Antimicrobial Agents and Chemotherapy 50*(11):3724-3733, 2006.

Wherry et al., "Viral Persistence Alters CD8 T-Cell Immunodominance and Tissue Distribution and Results in Distinct Stages of Functional Impairment," *Journal of Virology 77*(8):4911-4927, Apr. 2003.

\* cited by examiner

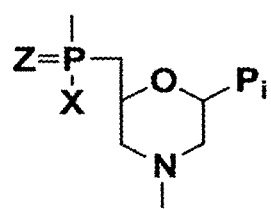 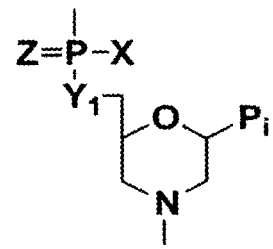
Fig. 1A    Fig. 1B
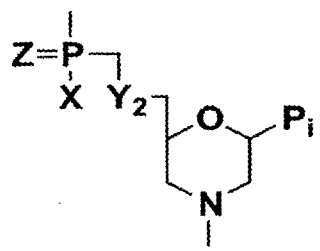 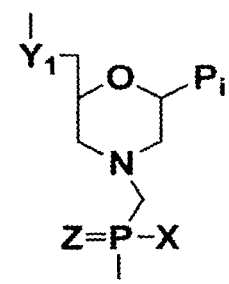
Fig. 1C    Fig. 1D

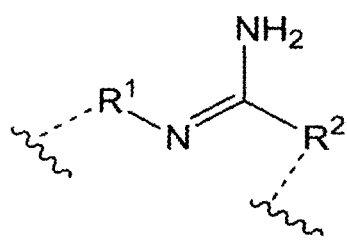 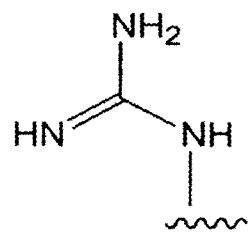 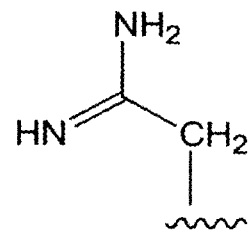
Fig. 3A     Fig. 3B     Fig. 3C
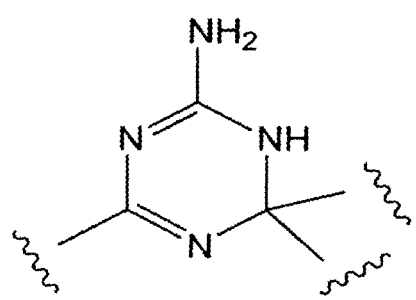 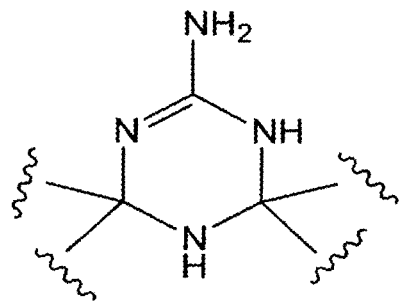
Fig. 3D     Fig. 3E
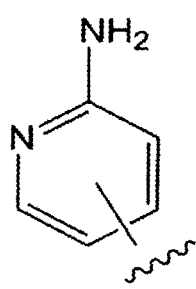 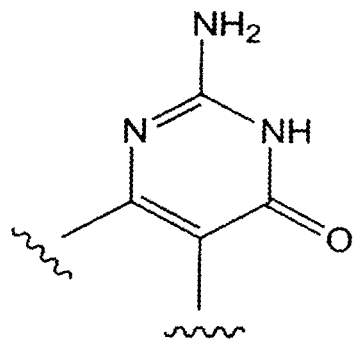
Fig. 3F     Fig. 3G

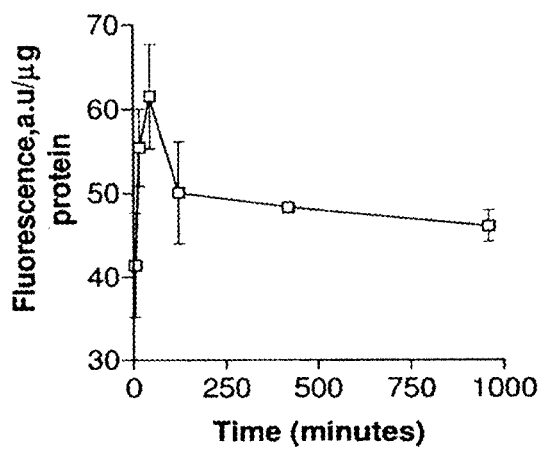
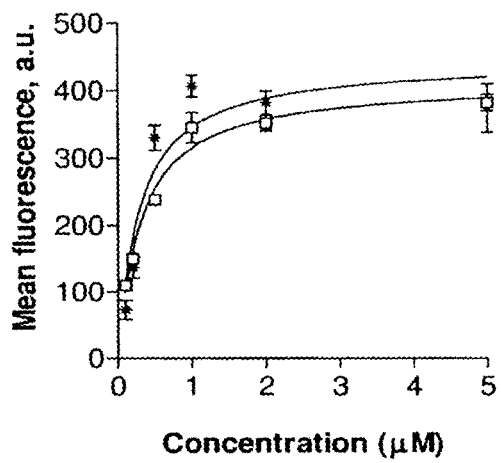
Fig. 5A     Fig. 5B
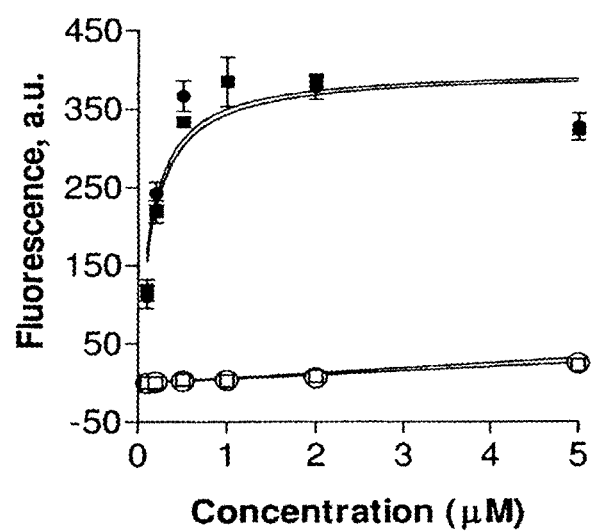
Fig. 6

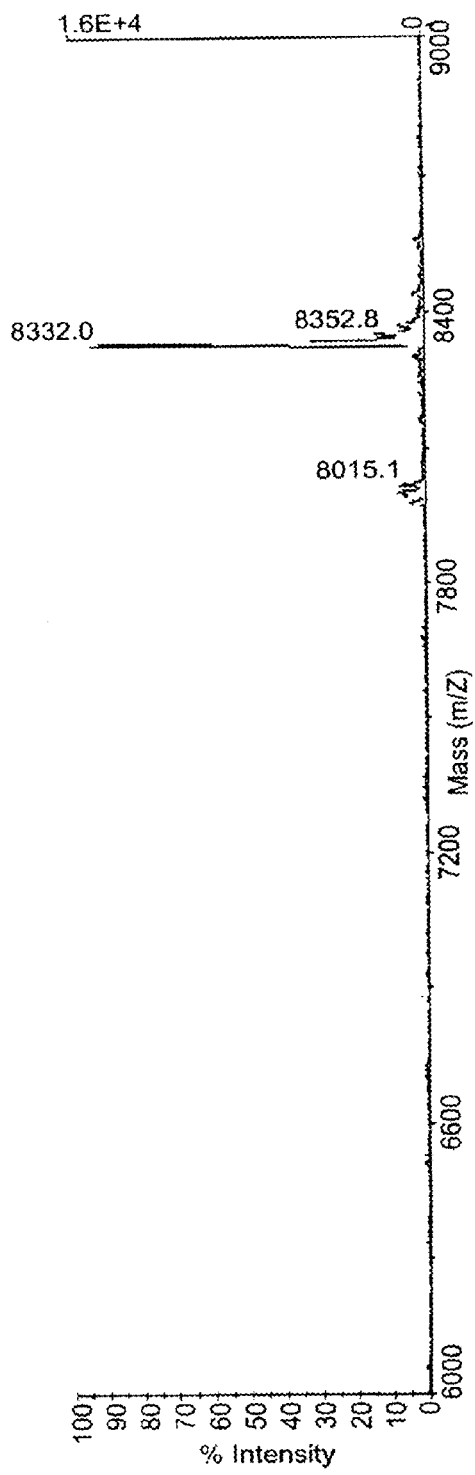
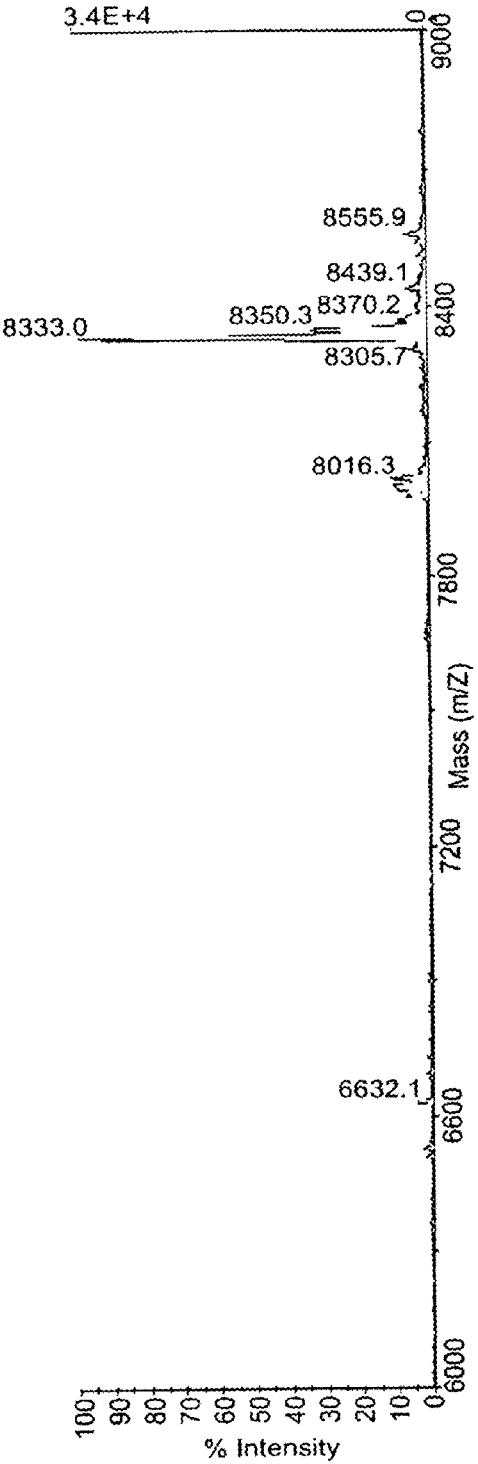
Fig. 26A
Fig. 26B

COMPOSITIONS FOR ENHANCING TRANSPORT OF MOLECULES INTO CELLS

This application is a continuation of U.S. patent application Ser. No. 10/836,804 filed on Apr. 29, 2004, now U.S. Pat. No. 7,468,418, which claims the benefit of U.S. Provisional Patent Application No. 60/466,703 filed on Apr. 29, 2003, both of which are incorporated in their entirety herein by reference.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 120178_401C1_SEQUENCE_LISTING.txt. The text file is 11.7 KB, was created on Oct. 1, 2014, and is being submitted electronically via EFS-Web.

FIELD OF THE INVENTION

The invention relates to compositions and methods for enhancing delivery of molecules, e.g. biological agents, into cells, and in particular to intracellular delivery and enhanced binding of substantially uncharged nucleic acid analogs, particularly phosphorodiamidate-linked morpholino oligomers.

REFERENCES

Arora, V. and P. L. Iversen (2000). "Antisense oligonucleotides targeted to the p53 gene modulate liver regeneration in vivo." *Drug Metab Dispos* 28(2): 131-8.

Astriab-Fisher, A., D. Sergueev et al. (2002). "Conjugates of antisense oligonucleotides with the Tat and antennapedia cell-penetrating peptides:effects on cellular uptake, binding to target sequences, and biologic actions." *Pharm Res* 19(6):744-54.

Astriab-Fisher, A., D. S. Sergueev et al. (2000). "Antisense inhibition of P-glycoprotein expression using peptide-oligonucleotide conjugates." *Biochem Pharmacol* 60(1): 83-90.

Devi, G. R. (2002). "Prostate cancer:status of current treatments and emerging antisense-based therapies." *Curr Opin Mol Ther* 4(2):138-48.

Devi, G. R., J. R. Oldenkamp et al. (2002). "Inhibition of human chorionic gonadotropin beta-subunit modulates the mitogenic effect of c-myc in human prostate cancer cells." *Prostate* 53(3):200-10.

Heasman, J., M. Kofron et al. (2000). "Beta-catenin signaling activity dissected in the early *Xenopus embryo*: a novel antisense approach." *Dev Biol* 222(1): 124-34.

Hudziak, R. M., E. Barofsky et al. (1996). "Resistance of morpholino phosphorodiamidate oligomers to enzymatic degradation." *Antisense Nucleic Acid Drug Dev* 6(4):267-72.

Iversen, P. L. (2001). Phosphoramidite Morpholino Oligomers. Antisense Drug Technology. S. T. Crooke. New York, Marcel Dekker, Inc.

Kang, S. H., M. J. Cho et al. (1998). "Up-regulation of luciferase gene expression with antisense oligonucleotides: implications and applications in functional assay development." *Biochemistry* 37(18):6235-9.

Khromykh, A. A., N. Kondratieva et al. (2003). "Significance in replication of the terminal nucleotides of the flavivirus genome." *J Virol* 77(19):10623-9.

Kipshidze, N., E. Keane et al. (2001). "Local delivery of c-myc neutrally charged antisense oligonucleotides with transport catheter inhibits myointimal hyperplasia and positively affects vascular remodeling in the rabbit balloon injury model." *Catheter Cardiovasc Interv* 54(2): 247-56.

Kipshidze, N. N., H. S. Kim et al. (2002). "Intramural coronary delivery of advanced antisense oligonucleotides reduces neointimal formation in the porcine stent restenosis model." *J Am Coll Cardiol* 39(10):1686-91.

McCaffrey, A. P., L. Meuse et al. (2003). "A potent and specific morpholino antisense inhibitor of hepatitis C translation in mice." *Hepatology* 38(2):503-8.

Moulton, H. M., M. C. Hase et al. (2003). "HIV Tat peptide enhances cellular delivery of antisense morpholino oligomers." *Antisense Nucleic Acid Drug Dev* 13(1):31-43.

Moulton, H. M., M. H. Nelson et al. (2004). "Cellular uptake of antisense morpholino oligomers conjugated to arginine-rich peptides." *Bioconjug Chem* 15(2):290-9.

Nasevicius, A. and S. C. Ekker (2000). "Effective targeted gene 'knockdown' in zebrafish." *Nat Genet.* 26(2):216-20.

Qin, G., M. Taylor et al. (2000). "In vivo evaluation of a morpholino antisense oligomer directed against tumor necrosis factor-alpha." *Antisense Nucleic Acid Drug Dev* 10(1):11-6.

Richard, J. P., K. Melikov et al. (2003). "Cell-penetrating peptides. A reevaluation of the mechanism of cellular uptake." *J Biol Chem* 278(1):585-90.

Ricker, J. L., J. E. Mata et al. (2002). "c-myc Antisense oligonucleotide treatment ameliorates murine ARPKD." *Kidney Int* 61 Suppl 1: 125-131.

Rothbard, J. B., E. Kreider et al. (2002). "Arginine-rich molecular transporters for drug delivery: role of backbone spacing in cellular uptake." *J Med Chem* 45(17):3612-8.

Stein, D., E. Foster et al. (1997). "A specificity comparison of four antisense types: morpholino, 2'-O-methyl RNA, DNA, and phosphorothioate DNA." *Antisense Nucleic Acid Drug Dev* 7(3):151-7.

Stein, D. A., D. E. Skilling et al. (2001). "Inhibition of vesivirus infections in mammalian tissue culture with antisense morpholino oligomers." *Antisense Nucleic Acid Drug Dev* 11(5):317-25.

Summerton, J. and D. Weller (1997). "Morpholino antisense oligomers: design, preparation, and properties." *Antisense Nucleic Acid Drug Dev* 7(3): 187-95.

Tisne, C., B. P. Roques et al. (2004). "The annealing mechanism of HIV-1 reverse transcription primer onto the viral genome." *J. Biol. Chem.* 279(5):3588-3595.

Wender, P. A., D. J. Mitchell et al. (2000). "The design, synthesis, and evaluation of molecules that enable or enhance cellular uptake: peptoid molecular transporters." *Proc Natl Acad Sci USA* 97(24):13003-8.

Yoo, H., P. Sazani et al. (1999). "PAMAM dendrimers as delivery agents for antisense oligonucleotides." *Pharm Res* 16(12): 1799-804.

Zuker, M. (2003). "Mfold web server for nucleic acid folding and hybridization prediction." *Nucleic Acids Res* 31(13):3406-15.

BACKGROUND OF THE INVENTION

The practical utility of many drugs having potentially useful biological activity is often stymied by difficulty in delivering such drugs to their targets. Compounds to be delivered into cells must generally be delivered from a largely aqueous extracellular environment and then penetrate a lipophilic cell membrane to gain entry to the cell. Unless the substance is actively transported by a specific transport mechanism, many molecules, particularly large molecules, are either too lipophilic for practical solubilization or are too hydrophilic to penetrate the membrane.

A segment of the HIV Tat protein consisting of amino acid residues 49-57 (Tat 49-57, having the sequence RKKRRQRRR) (SEQ ID NO: 42) has been used to deliver biologically active peptides and proteins to cells (e.g. Barsoum et al., 1994, PCT Pubn. No. WO 94/04686). Tat (49-60) has been used to enhance delivery of phosphorothioate oligonucleotides (Astriab-Fisher, Sergueev et al. 2000; Astriab-Fisher, Sergueev et al. 2002). Reverse Tat, or rTat (57-49) (RRRQRRKKR) (SEQ ID NO.:12), has been reported to deliver fluorescein into cells with enhanced efficacy compared to Tat (49-57) (Wender, Mitchell et al. 2000; Rothbard, Kreider et al. 2002). Rothbard and Wender have also disclosed other arginine-rich transport polymers (PCT Pubn. No. WO 01/62297; U.S. Pat. No. 6,306,993; US Patent Appn. Pubn. No. 2003/0032593).

Oligonucleotides are one class of potentially useful drug compounds whose delivery has often been an impediment to therapeutic use. Phosphorodiamidate-linked morpholino oligomers (PMOs; see e.g. Summerton and Weller, 1997) have been found more promising in this regard than charged oligonucleotide analogs such as phosphorothioates. The PMOs are water-soluble, uncharged or substantially uncharged antisense molecules that inhibit gene expression by preventing binding or progression of splicing or translational machinery components. PMOs have also been to shown to inhibit or block viral replication (Stein, Skilling et al. 2001; McCaffrey, Meuse et al. 2003). They are highly resistant to enzymatic digestion (Hudziak, Barofsky et al. 1996). PMOs have demonstrated high antisense specificity and efficacy in vitro in cell-free and cell culture models (Stein, Foster et al. 1997; Summerton and Weller 1997), and in vivo in zebrafish, frog and sea urchin embryos (Heasman, Kofron et al. 2000; Nasevicius and Ekker 2000), as well as in adult animal models, such as rats, mice, rabbits, dogs, and pigs (see e.g. Arora and Iversen 2000; Qin, Taylor et al. 2000; Iversen 2001; Kipshidze, Keane et al. 2001; Devi 2002; Devi, Oldenkamp et al. 2002; Kipshidze, Kim et al. 2002; Ricker, Mata et al. 2002).

Antisense PMO oligomers have been shown to be taken up into cells and to be more consistently effective in vivo, with fewer nonspecific effects, than other widely used antisense oligonucleotides (see e.g. P. Iversen, "Phosphoramidite Morpholino Oligomers", in *Antisense Drug Technology*, S. T. Crooke, ed., Marcel Dekker, Inc., New York, 2001). However, further enhancement in uptake and antisense efficacy is desirable in order to fully explore their potential.

SUMMARY OF THE INVENTION

In one aspect, the invention provides a method for enhancing the ability of an nucleic acid analog, having a substantially uncharged backbone and a targeting base sequence, to bind to a target sequence in a nucleic acid, the method comprising:

conjugating to the nucleic acid analog a peptide consisting of 8 to 16 subunits selected from X subunits, Y subunits, and optional Z subunits, including at least six, and preferably at least eight, X subunits, at least two Y subunits, and at most three Z subunits, where >50% of said subunits are X subunits, and where (a) each X subunit independently represents arginine or an arginine analog, said analog being a cationic α-amino acid comprising a side chain of the structure $R^1N=C(NH_2)R^2$, where $R^1$ is H or R; $R^2$ is R, $NH_2$, NHR, or $NR_2$, where R is lower alkyl or lower alkenyl and may further include oxygen or nitrogen; $R^1$ and $R^2$ may together form a ring; and the side chain is linked to said amino acid via $R^1$ or $R^2$;

(b) each Y subunit independently represents a neutral amino acid $—C(O)—(CHR)_n—NH—$, where (i) n is 2 to 7 and each R is independently H or methyl, or (ii) n is 1 and R is a neutral side chain selected from substituted or unsubstituted alkyl, alkenyl, alkynyl, aryl, and aralkyl, wherein said neutral side chain, when selected from substituted alkyl, alkenyl, and alkynyl, includes at most one heteroatom for every two, preferably every four, and more preferably every six carbon atoms; and (c) each Z subunit independently represents an amino acid selected from alanine, asparagine, cysteine, glutamine, glycine, histidine, lysine, methionine, serine, and threonine.

Preferably, the above-described peptide, when conjugated to an antisense oligomer having said substantially uncharged backbone (i.e. the same type of backbone as the nucleic acid analog), is effective to enhance the binding of the antisense oligomer to its target sequence, relative to the antisense oligomer in unconjugated form, as evidenced by:

(i) a decrease in expression of an encoded protein, relative to that observed with unconjugated oligomer, when binding of the antisense oligomer to its target sequence is effective to block a translation start codon for the encoded protein, or (ii) an increase in expression of an encoded protein, relative to that observed with unconjugated oligomer, when binding of the antisense oligomer to its target sequence is effective to block an aberrant splice site in a pre-mRNA which encodes said protein when correctly spliced.

Assays suitable for measurement of these effects are described further below. In one embodiment, conjugation of the peptide provides this activity in a cell-free translation assay, as described herein. Preferably, activity is enhanced by a factor of at least two, more preferably by a factor of at least five, and most preferably by a factor of at least ten. In some embodiments, activity may be enhanced by factors of 50, 100 or more.

Alternatively or in addition, the peptide is effective to enhance the transport of the nucleic acid analog into a cell, relative to the analog in unconjugated form. Preferably, transport is enhanced by a factor of at least two, more preferably by a factor of at least five, and most preferably by a factor of at least ten. In some embodiments, uptake may be enhanced by factors of 50, 100 or more.

In the conjugates, the nucleic acid analog may be conjugated to the peptide via a Y subunit, a cysteine subunit, or an uncharged, non-amino acid linker moiety, as described further below.

The optional Z subunits, when present, are preferably selected from alanine, glycine, methionine, serine, and threonine. The peptide may include zero, one, two, or three Z subunits.

Preferably, for each X subunit, the side chain moiety is independently selected from the group consisting of guanidyl ($HN=C(NH_2)NH—$), amidinyl ($HN=C(NH_2)C<$), 2-amino dihydropyrimidyl, 2-aminotetrahydropyrimidyl, 2-aminopyridinyl, and 2-amino pyrimidonyl. More preferably, for each X, the side chain moiety is guanidyl, such as in an arginine subunit.

Preferably, when Y is defined as a neutral amino acid subunit —C(O)—(CHR)$_n$—NH—, where n is 2 to 7, the subunit is of the form —C(O)—(CH$_2$)$_{n-1}$(CHR)—NH—, where R is H or methyl, and is preferably H.

In other preferred embodiments, the at least two Y subunits include (i) two neutral, hydrophobic α-amino acid subunits having side chains independently selected from substituted or unsubstituted alkyl, alkenyl, alkynyl, aryl, and aralkyl, wherein said side chain, when selected from substituted alkyl, alkenyl, and alkynyl, includes at most one heteroatom for every six carbon atoms, and wherein said subunits are contiguous or are flanking a linker moiety, or (ii) two neutral, hydrophobic amino acid subunits —C(O)—(CH$_2$)$_{n-1}$(CHR)—NH—, where n is 2 to 7 and R is H or methyl and is preferably H.

In selected embodiments, the peptide has exactly two Y subunits of type (i), which are contiguous or are flanking a cysteine subunit, which acts as a linker Preferably, the two Y subunits are contiguous. In these embodiments, each Y preferably represents a hydrophobic α-amino acid subunit having an aryl or aralkyl side chain, such as, for example, phenylalanine, tyrosine, tryptophan, leucine, isoleucine, or valine. In selected embodiments of the peptide, each Y is independently selected from phenylalanine and tyrosine. One such embodiment is a peptide having the formula Arg$_9$Phe$_2$ (SEQ ID NO: 13). Such a peptide may be linked to the nucleic acid analog via a cysteine subunit attached to the terminal Phe.

In other embodiments, each Y is a neutral, hydrophobic amino acid subunit —CO—(CH$_2$)$_n$—CHR—NH—, where n is 2 to 7 and R is H. For example, when n is 5 and R is H, Y is a 6-aminohexanoic acid subunit, abbreviated herein as Ahx. In selected embodiments of this group, each X comprises a guanidyl side chain moiety, as in an arginine subunit. Preferred peptides of this type include those comprising arginine dimers alternating with single Y subunits, where Y is preferably Ahx. Examples include peptides having the formula (RYR)$_4$ (SEQ ID NO: 45) or the formula (RRY)$_4$ (SEQ ID NO: 46), where Y is preferably Ahx. In the latter case, the nucleic acid analog is preferably linked to a terminal Y subunit.

The nucleic acid analog to which the peptide is conjugated, having a substantially uncharged backbone, is preferably a morpholino oligomer or a peptide nucleic acid. Preferably, the oligomer backbone is fully uncharged. In preferred embodiments, the nucleic acid analog is a morpholino oligomer, comprising morpholino subunits linked by phosphorus-containing linkages, one to three atoms long, between the morpholino nitrogen of one subunit and an exocyclic carbon at the morpholino 3-position of an adjacent subunit. The linkages are preferably two-atom uncharged phosphorodiamidate linkages, in accordance with the structure:

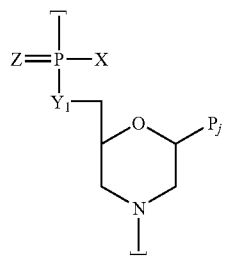

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, or alkyl amino.

Conjugation of a peptide to a nucleic acid analog as described above forms a peptide-oligomer conjugate which is more effective than the unconjugated oligomer in various functions, including: inhibiting expression of targeted mRNA in a protein expression system; inhibiting splicing of targeted pre-mRNA; and inhibiting replication of a virus, by targeting cis-acting elements which control nucleic acid replication or mRNA transcription of the virus.

In another aspect, the invention provides a peptide-nucleic acid analog conjugate, comprising a nucleic acid analog having a substantially uncharged backbone and a targeting base sequence, and covalently linked to the nucleic acid analog, a peptide consisting of 8 to 16 subunits selected from X subunits, Y subunits, and optional Z subunits, including at least eight X subunits, at least two Y subunits, and at most three Z subunits, wherein >50% of said subunits are X subunits, and where (a) each X subunit independently represents arginine or an arginine analog, said analog being a cationic α-amino acid subunit comprising a side chain of the structure R$^1$N=C(NH$_2$)R$^2$, where R$^1$ is H or R; R$^2$ is R$^1$, NH$_2$, NHR, or NR$_2$, where R is lower alkyl or lower alkenyl and may further include oxygen or nitrogen; R$^1$ and R$^2$ may together form a ring; and the side chain is linked to said amino acid subunit via R$^1$ or R$^2$;

(b) said at least two Y subunits include (i) two neutral α-amino acid subunits having side chains independently selected from substituted or unsubstituted alkyl, alkenyl, alkynyl, aryl, and aralkyl, wherein said side chain, when selected from substituted alkyl, alkenyl, and alkynyl, includes at most one heteroatom for every two, preferably every four, and more preferably every six carbon atoms, and wherein said subunits are contiguous or are flanking a linker moiety, or (ii) two neutral, hydrophobic amino acid subunits —C(O)—(CH$_2$)$_{n-1}$(CHR)—NH—, where n is 2 to 7 and R is H or methyl; and (c) Z represents an amino acid subunit selected from alanine, asparagine, cysteine, glutamine, glycine, histidine, lysine, methionine, serine, and threonine.

Preferably, the conjugate includes a peptide which, when conjugated to an antisense oligomer having the same type of substantially uncharged backbone as the nucleic acid analog, is effective to enhance the binding of the antisense oligomer to its target sequence, relative to the antisense oligomer in unconjugated form, as evidenced by:

(i) a decrease in expression of an encoded protein, relative to that observed with unconjugated oligomer, when binding of the antisense oligomer to its target sequence is effective to block a translation start codon for the encoded protein, or (ii) an increase in expression of an encoded protein, relative to that observed with unconjugated oligomer, when binding of the antisense oligomer to its target sequence is effective to block an aberrant splice site in a pre-mRNA which encodes said protein when correctly spliced.

Assays suitable for measurement of these effects are described further below. In one embodiment, conjugation of the peptide provides this activity in a cell-free translation assay, as described herein. Preferably, activity is enhanced by a factor of at least two, more preferably by a factor of at least five, and most preferably by a factor of at least ten. In some embodiments, activity may be enhanced by factors of 50, 100 or more.

Alternatively or in addition, the peptide is effective to enhance the transport of the nucleic acid analog into a cell, relative to the analog in unconjugated form. Preferably, transport is enhanced by a factor of at least two, more preferably by a factor of at least five, and most preferably by a factor of at least ten. In some embodiments, activity may be enhanced by factors of 50, 100 or more.

In the conjugates of the invention, the nucleic acid analog is preferably conjugated to the peptide via a linker moiety selected from a Y subunit, a cysteine subunit, and an uncharged, non-amino acid linker moiety.

Preferably, the side chain moieties of the X subunits are independently selected from the group consisting of guanidyl (HN=C(NH$_2$)NH—), amidinyl (HN=C(NH$_2$)C<), 2-aminodihydropyrimidyl, 2-aminotetrahydropyrimidyl, 2-aminopyridinyl, and 2-amino pyrimidonyl. More preferably, each such side chain moiety is guanidyl; for example, each X can be an arginine subunit.

The optional Z subunits, when present, are preferably selected from alanine, glycine, methionine, serine, and threonine. The peptide may include zero, one, two, or three Z subunits, and preferably includes at most one Z subunit.

In selected embodiments, the peptide has exactly two Y subunits of type (i), which are contiguous or are flanking a cysteine subunit. Preferably, the two Y subunits are contiguous.

In further preferred embodiments, each Y represents a hydrophobic α-amino acid subunit having an aryl or aralkyl side chain; for example, each Y may be independently selected from the group consisting of phenylalanine, tyrosine, tryptophan, leucine, isoleucine, and valine.

In selected embodiments, each Y is independently selected from phenylalanine and tyrosine; in further embodiments, each Y is phenylalanine. This includes, for example, conjugates which consist of arginine subunits, phenylalanine subunits, a linker moiety, and the nucleic acid analog. One such conjugate includes a peptide having the formula Arg$_9$Phe$_2$.

The linker moiety may be, for example, a cysteine subunit attached to the terminal Phe.

In other embodiments, each Y is a neutral, hydrophobic amino acid subunit —C(O)—(CH$_2$)$_{n-1}$(CHR)—NH—, where n is 2 to 7 and R is H. In one such embodiment, n is 5, such that Y is a 6-aminohexanoic acid subunit. In selected embodiments of this class, each X has a guanidyl side chain, e.g. as in arginine subunits. These include conjugates in which the peptide comprises arginine dimers alternating with single Y subunits. Examples of such peptides are the peptide having the formula (RYR)$_4$ (SEQ ID NO: 45) and the peptide having the formula (RRY)$_4$ (SEQ ID NO: 46). In the latter case, the nucleic acid analog is preferably linked to a terminal Y subunit.

The nucleic acid analog to which the peptide is conjugated, having a substantially uncharged backbone, is preferably a morpholino oligomer, as described above, or a peptide nucleic acid.

The peptide-oligomer conjugates of the invention are more effective than the unconjugated oligomer in various functions, including: inhibiting expression of targeted mRNA in a protein expression system, including cell free translation systems; inhibiting splicing of targeted pre-mRNA; and inhibiting replication of a virus, by targeting cis-acting elements which control nucleic acid replication or mRNA transcription of the virus. Preferably, activity is enhanced by a factor of at least two, more preferably by a factor of at least five, and most preferably by a factor of at least ten.

Alternatively or in addition, the peptide is effective to enhance the transport of the nucleic acid analog into a cell, relative to the analog in unconjugated form. Preferably, transport is enhanced by a factor of at least two, more preferably by a factor of at least five, and most preferably by a factor of at least ten.

In another aspect, the invention provides a conjugate comprising a pharmacological agent covalently linked to a peptide, wherein the peptide consists of 8 to 16 subunits selected from X subunits, Y subunits, and optional Z subunits, including at least six, and preferably at least eight, X subunits, at least two Y subunits, and at most three Z subunits, wherein >50% of said subunits are X subunits, and where (a) each X subunit independently represents arginine or an arginine analog, said analog being a cationic α-amino acid comprising a side chain of the structure R$^1$N=C(NH$_2$)R$^2$, where R$^1$ is H or R; R$^2$ is R, NH$_2$, NHR, or NR$_2$, where R is lower alkyl or lower alkenyl and may further include oxygen or nitrogen; R$^1$ and R$^2$ may together form a ring; and the side chain is linked to said amino acid via R$^1$ or R$^2$;

(b) each Y subunit independently represents a neutral amino acid —C(O)—(CHR)—NH—, where R is a neutral side chain selected from substituted or unsubstituted alkyl, alkenyl, alkynyl, aryl, and aralkyl, wherein said neutral side chain, when selected from substituted alkyl, alkenyl, and alkynyl, includes at most one heteroatom for every two, preferably every four, and more preferably every six carbon atoms; and (c) each Z subunit independently represents an amino acid selected from alanine, asparagine, cysteine, glutamine, glycine, histidine, lysine, methionine, serine, and threonine.

The peptide is effective to enhance the transport of the agent into a cell relative to the agent in unconjugated form. The agent may be conjugated to the peptide via a Y subunit, a cysteine subunit, or an uncharged, non-amino acid linker moiety.

The optional Z subunits, when present, are preferably selected from alanine, glycine, methionine, serine, and threonine. The peptide may include zero, one, two, or three Z subunits, and preferably includes at most one Z subunit.

In selected embodiments of X, the side chain moiety is independently selected from the group consisting of guanidyl (HN=C(NH$_2$)NH—), amidinyl (HN=C(NH$_2$)C<), 2-amino dihydropyrimidyl, 2-aminotetrahydropyrimidyl, 2-aminopyridinyl, and 2-amino pyrimidonyl. Preferably, for each X, the side chain moiety is guanidyl; more preferably, each X is an arginine subunit.

In selected embodiments of Y, the at least two Y subunits include two neutral, hydrophobic α-amino acid subunits having side chains independently selected from substituted or unsubstituted alkyl, alkenyl, alkynyl, aryl, and aralkyl, wherein said side chain, when selected from substituted alkyl, alkenyl, and alkynyl, includes at most one heteroatom for every six carbon atoms, and wherein said subunits are contiguous or are flanking a linker moiety. Preferably, the peptide has exactly two Y subunits which are contiguous or are flanking a cysteine subunit, which acts as a linker moiety; more preferably, the Y subunits are contiguous.

In further preferred embodiments, each Y represents a hydrophobic α-amino acid subunit having an aryl or aralkyl side chain; for example, each Y may be independently selected from the group consisting of phenylalanine, tyrosine, tryptophan, leucine, isoleucine, and valine.

In selected embodiments, each Y is independently selected from phenylalanine and tyrosine; in further embodiments, each Y is phenylalanine. This includes, for example, conjugates which consist of arginine subunits, phenylalanine subunits, a linker moiety, and the nucleic acid analog. One such conjugate includes a peptide having the formula $Arg_9Phe_2$ (SEQ ID NO: 13).

The linker moiety may be, for example, a cysteine subunit attached to the terminal Phe.

In a related aspect, the invention provides a method for enhancing cell uptake of a pharmacological agent, the method comprising conjugating the agent to a transport peptide as described above; i.e. where the peptide consists of 8 to 16 subunits selected from X subunits, Y subunits, and optional Z subunits, including at least six, and preferably at least eight, X subunits, at least two Y subunits, and at most three Z subunits, wherein >50% of said subunits are X subunits, and where (a) each X subunit independently represents arginine or an arginine analog, said analog being a cationic α-amino acid comprising a side chain of the structure $R^1N=C(NH_2)R^2$, where $R^1$ is H or R; $R^2$ is R, $NH_2$, NHR, or $NR_2$, where R is lower alkyl or lower alkenyl and may further include oxygen or nitrogen; $R^1$ and $R^2$ may together form a ring; and the side chain is linked to said amino acid via $R^1$ or $R^2$;

(b) each Y subunit independently represents a neutral amino acid —C(O)—(CHR)—NH—, where R is a neutral side chain selected from substituted or unsubstituted alkyl, alkenyl, alkynyl, aryl, and aralkyl, wherein said neutral side chain, when selected from substituted alkyl, alkenyl, and alkynyl, includes at most one heteroatom for every two, preferably every four, and more preferably every six carbon atoms; and (c) each Z subunit independently represents an amino acid selected from alanine, asparagine, cysteine, glutamine, glycine, histidine, lysine, methionine, serine, and threonine.

The invention also provides a composition useful for intracellular delivery of an nucleic acid analog in vivo, comprising a peptide-nucleic acid analog conjugate, as described above, and a suspension of insoluble gas-containing microbubbles in an aqueous vehicle comprising at least one filmogenic compound selected from a protein, surfactant, lipid, polysaccharide, and combinations thereof. Preferably, the microbubbles are suspended in an aqueous vehicle comprising albumin, and the insoluble gas is selected from the group consisting of perfluoromethane, perfluoroethane, perfluoropropane, perfluorobutane, and perfluoropentane.

In another aspect, the invention provides a modified nucleic acid analog, comprising (i) a plurality of subunits connected by intersubunit linkages, and supporting a sequence of bases effective to hybridize to a complementary-sequence target polynucleotide, to form a target/antisense duplex; and (ii) carried on at least six contiguous intersubunit linkages, a charged moiety of the structure $R^1N=C(NH_2)R^2$, where $R^1$ is H or R; $R^2$ is R, $NH_2$, NHR, or $NR_2$, where R is lower alkyl or lower alkenyl and may further include oxygen or nitrogen; $R^1$ and $R^2$ may together form a ring; and the side chain moiety is linked to said amino acid subunit via $R^1$ or $R^2$.

Preferably, the charged moiety is selected from the group consisting of guanidyl (—N=C(NH$_2$)NH—), amidinyl (—C(=NH)(NH$_2$)), 2-amino hexahydropyrimidyl (=HN—H(NH$_2$)NH—), 2-aminopyridinyl (—C(=N) (NH$_2$)), and 2-aminopyrimidonyl (—N—NH$_2$)=N—). More preferably, the charged moiety is guanidyl. In one embodiment, the subunits are morpholino subunits, and the linkages are phosphorodiamidate linkages.

These and other objects and features of the invention will become more fully apparent when the following detailed description of the invention is read in conjunction with the accompanying drawings.

BRIEF DESCRIPTION OF THE DRAWINGS

FIGS. 1A-1D show several preferred morpholino-type subunits having 5-atom (A), six-atom (B) and seven-atom (C-D) linking groups suitable for forming polymers.

FIGS. 3A-G show exemplary X side chain structures, for use in various embodiments of the transporters of the invention.

FIG. 5A shows adsorption of a fluorescein-labeled peptide-PMO conjugate ($R_9F_2C$-705-FL) (SEQ ID NO.:43-SEQ ID NO: 1) over time, as measured in HeLa pLuc705 cells treated with 1 µM of the conjugate.

FIG. 5B shows absorption with increasing concentration, measured at 37° C. ( ) and 17° C. (*), in HeLa pLuc705 cells incubated with $R_9F_2C$-705-FL (SEQ ID NO.:43-SEQ ID NO: 1) for 70 minutes.

FIG. 6 shows adsorption with increasing concentration in HeLa pLuc705 cells incubated with $R_9F_2C$-705-FL (SEQ ID NO.:43-SEQ ID NO: 1) and with (D)-$R_9F_2C$-705-FL (SEQ ID NO: 49-SEQ ID NO:1), without trypsin treatment (closed square and circle, respectively), and with trypsin treatment (open square and circle, respectively).

FIG. 23 represents results obtained with the pDCLD reporter gene construct.

FIGS. 25A-B and 26A-B show that a transport peptide containing 6-aminohexanoic acid (Ahx), (RAhxR)$_4$ (SEQ ID NO.:34), is resistant to proteinase K degradation and that a transport peptide containing all natural amino acids, $R_9F_2$ (SEQ ID NO.:13), was not resistant to proteinase K degradation.

DETAILED DESCRIPTION OF THE INVENTION

I. Definitions

Figure 2A:
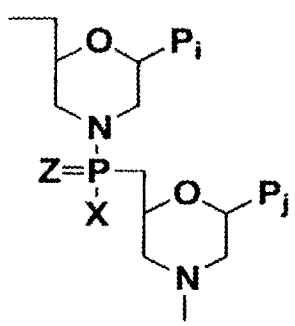
FIGS. 2A-D show the repeating subunit segment of exemplary morpholino oligonucleotides, constructed using subunits A-D, respectively, of FIG. 1.

"Alkyl" refers to a fully saturated monovalent radical containing carbon and hydrogen, which may be branched, linear, or cyclic (cycloalkyl). Examples of alkyl groups are methyl, ethyl, n-butyl, t-butyl, n-heptyl, isopropyl, cyclopropyl, cyclopentyl, ethylcyclopentyl, and cyclohexyl. Generally preferred are alkyl groups having one to six carbon atoms, referred to as "lower alkyl", and exemplified by methyl, ethyl, n-butyl, i-butyl, t-butyl, isoamyl, n-pentyl, and isopentyl. In one embodiment, lower alkyl refers to $C_1$ to $C_4$ alkyl.

"Alkenyl" refers to an unsaturated monovalent radical containing carbon and hydrogen, which may be branched, linear, or cyclic. The alkenyl group may be monounsaturated or polyunsaturated. Generally preferred are alkenyl groups having one to six carbon atoms, referred to as "lower alkenyl". In one embodiment, lower alkenyl refers to $C_2$ to $C_4$ alkenyl.

"Aryl" refers to a substituted or unsubstituted monovalent aromatic radical, generally having a single ring (e.g., benzene) or two condensed rings (e.g., naphthyl). Generally preferred are aryl groups having a single ring. Preferably, the rings are hydrocarbon rings.

"Aralkyl" refers to an alkyl, preferably lower ($C_1$-$C_4$, more preferably $C_1$-$C_2$) alkyl, substituent which is further substituted with an aryl group; examples are benzyl (—$CH_2C_6H_5$) and phenethyl (—$CH_2CH_2C_6H_5$).

The term "substituted", with respect to an alkyl, alkenyl, alkynyl, aryl, aralkyl, or alkaryl group in a neutral side chain, refers to replacement of a hydrogen atom with a lower alkyl group or a neutral heteroatom-containing substituent, such as, for example, halogen, e.g. fluorine, chlorine, or bromine; hydroxy, alkoxy, thiol, alkylthio, oxo (keto), nitro, cyano, or various esters such as carboxylic, sulfonic, or phosphonic. Preferably, such substituents are selected from hydroxy, lower alkoxy, thiol, lower alkylthio, and oxo (keto).

A nucleic acid analog having a "substantially uncharged" backbone (also referred to as a "substantially uncharged nucleic acid analog") is one having at most one charged (at physiological pH) intersubunit linkage for every four uncharged (at physiological pH) linkages, preferably at most one for every eight, and more preferably at most one for every sixteen uncharged linkages. In a preferred embodiment, the nucleic acid analogs described herein are fully uncharged.

In general, terms such as "charged", "uncharged", and "neutral" used herein refer to the state of the group so described at physiological pH, i.e. about 7.4.

The "backbone" of such an analog refers to the structure supporting the base-pairing moieties; i.e., for a morpholino oligomer, as described below, the "backbone" includes morpholino ring structures connected by phosphorus-containing linkages.

A "target sequence" refers to a complementary or near-complementary sequence to which an antisense oligomer is targeted, by virtue of its base sequence, and is able to stably bind under physiological conditions of temperature and pH.

The term "antisense activity", in reference to steric blocking oligomers, refers to the ability of an antisense oligomer to bind to its target sequence and inhibit the function of that target sequence, or closely adjacent sequences, e.g., blocking translation of an mRNA, blocking cis-acting elements in viral RNA replication, or blocking the accurate splicing of pre-RNA.

I. Compound-Transporter Conjugates

A. Peptide Conjugates

In one aspect, the invention provides a peptide-nucleic acid analog conjugate, comprising a nucleic acid analog having a substantially uncharged backbone and a targeting base sequence, and covalently linked to the nucleic acid analog, a peptide consisting of 8 to 16 subunits selected from X subunits, Y subunits, and optional Z subunits, including at least eight X subunits, at least two Y subunits, and at most three Z subunits, where >50% of said subunits are X subunits, and where (a) each X subunit independently represents arginine or an arginine analog, said analog being a cationic α-amino acid subunit comprising a side chain of the structure $R^1N=C(NH_2)R^2$ (see FIG. 3A), where $R^1$ is H or R; $R^2$ is R, $NH_2$, NHR, or $NR_2$, where R is lower alkyl or lower alkenyl and may further include oxygen or nitrogen; $R^1$ and $R^2$ may together form a ring; and the side chain is linked to said amino acid subunit via $R^1$ or $R^2$;

(b) said at least two Y subunits include (i) two neutral α-amino acid subunits having side chains independently selected from substituted or unsubstituted alkyl, alkenyl, alkynyl, aryl, and aralkyl, wherein said side chain, when selected from substituted alkyl, alkenyl, and alkynyl, includes at most one heteroatom for every two, preferably every four, and more preferably every six carbon atoms, and wherein said subunits are contiguous or are flanking a linker moiety, or (ii) two neutral, hydrophobic amino acid subunits —C(O)—$(CH_2)_{n-1}$(CHR)—NH—, where n is 2 to 7 and R is H or methyl; and (c) Z represents an amino acid subunit selected from alanine, asparagine, cysteine, glutamine, glycine, histidine, lysine, methionine, serine, and threonine.

Z may also include amino acids having side chains which are one- or two-carbon homologs of naturally occurring side chains, excluding side chains which are negatively charged at physiological pH (e.g. carboxylate side chains). Preferably, the side chains are neutral. More preferred side chains are side chains of naturally occurring amino acids. The optional Z subunits are preferably selected from alanine, glycine, methionine, serine, and threonine. The peptide may include zero, one, two, or three Z subunits, and preferably includes at most two Z subunits.

Preferably, the conjugate includes a peptide which, when conjugated to an antisense oligomer having the same type of substantially uncharged backbone as the nucleic acid analog, is effective to enhance the binding of the antisense oligomer to its target sequence, relative to the antisense oligomer in unconjugated form, as evidenced by:

(i) a decrease in expression of an encoded protein, relative to that provided by the unconjugated oligomer, when binding of the antisense oligomer to its target sequence is effective to block a translation start codon for the encoded protein, or (ii) an increase in expression of an encoded protein, relative to that provided by the unconjugated oligomer, when binding of the antisense oligomer to its target sequence is effective to block an aberrant splice site in a pre-mRNA which encodes said protein when correctly spliced. Assays suitable for measurement of these effects are described further below. In one embodiment, conjugation of the peptide provides this activity in a cell-free translation assay, as described herein. Preferably, activity is enhanced by a factor of at least two, more preferably by a factor of at least five, and most preferably by a factor of at least ten.

Alternatively or in addition, the peptide is effective to enhance the transport of the nucleic acid analog into a cell, relative to the analog in unconjugated form. Preferably, transport is enhanced by a factor of at least two, more preferably by a factor of at least five, and most preferably by a factor of at least ten.

In the conjugates of the invention, the nucleic acid analog is preferably conjugated to the peptide via a linker moiety selected from a Y subunit, a cysteine subunit, and an uncharged, non-amino acid linker moiety.

Preferably, the side chain moieties of the X subunits are independently selected from the group consisting of guanidyl (HN=C($NH_2$)NH—), amidinyl (HN=C($NH_2$)C<), 2-aminodihydropyrimidyl, 2-aminotetrahydropyrimidyl, 2-aminopyridinyl, and 2-amino pyrimidonyl (FIGS. 3B-G, respectively, with possible linkage sites indicated). Note that, in structures 3D, 3E, and 3G, linking of the side chain to the amino acid subunit could take place via any of the ring —NH— groups as well as via any of the carbon atoms indicated. In one embodiment, the side chain moiety is guanidyl, as in the amino acid subunit arginine (Arg).

In selected embodiments, the peptide has exactly two Y subunits of type (i), which are contiguous or are flanking a cysteine subunit. Preferably, the two Y subunits are contiguous. Preferred side chains for Y subunits of type (i) include side chains of naturally occurring amino acids and one- or two-carbon homologs thereof, excluding side chains which are charged at physiological pH. More preferred side chains are side chains of naturally occurring amino acids. In further preferred embodiments, the side chain is an aryl or aralkyl side chain; for example, each Y may be independently selected from the group consisting of phenylalanine, tyrosine, tryptophan, leucine, isoleucine, and valine.

In selected embodiments, each Y is independently selected from phenylalanine and tyrosine; in further embodiments, each Y is phenylalanine. This includes, for example, conjugates which consist of arginine subunits, phenylalanine subunits, a linker moiety, and the nucleic acid analog. One such conjugate includes a peptide having the formula $Arg_9Phe_2$ (SEQ ID NO: 13).

The linker moiety may be, for example, a cysteine subunit attached to the terminal Phe.

In other embodiments, each Y is a neutral, hydrophobic amino acid subunit —C(O)—$(CH_2)_{n-1}$(CHR)—NH—, where n is 2 to 7 and R is H. In one such embodiment, n is 5, such that Y is a 6-aminohexanoic acid subunit (Ahx). In selected embodiments of this class, each X has a guanidyl side chain, e.g. as in arginine subunits. These include conjugates in which the peptide comprises arginine dimers alternating with single Y subunits, where Y is preferably Ahx. Examples of such peptides are the peptide having the formula (RYR)$_4$ (SEQ ID NO: 45) and the peptide having the formula (RRY)$_4$ (SEQ ID NO: 46), where Y is preferably Ahx. In the latter case, the nucleic acid analog is preferably linked to a terminal Y subunit.

The nucleic acid analog to which the peptide is conjugated, having a substantially uncharged backbone, is preferably a morpholino oligomer, as described herein, or a peptide nucleic acid.

The peptide-oligomer conjugates of the invention are more effective than the unconjugated oligomer in various functions, including: inhibiting expression of targeted mRNA in a protein expression system, including cell free translation systems; inhibiting splicing of targeted pre-mRNA; and inhibiting replication of a virus, by targeting cis-acting elements which control nucleic acid replication or mRNA transcription of the virus. Preferably, activity is enhanced by a factor of at least two, more preferably by a factor of at least five, and most preferably by a factor of at least ten.

Alternatively or in addition, the peptide is effective to enhance the transport of the nucleic acid analog into a cell, relative to the analog in unconjugated form. Preferably, transport is enhanced by a factor of at least two, more preferably by a factor of at least five, and most preferably by a factor of at least ten.

Also included are conjugates of other pharmacological agents, not limited to nucleic acid analogs, linked to a peptide transporter where the Y subunits are of type (i) above. Specifically, the peptide consists of 8 to 16 subunits selected from X subunits, Y subunits, and optional Z subunits, including at least six, and preferably at least eight, X subunits, at least two Y subunits, and at most three Z subunits, wherein >50% of said subunits are X subunits. The X and Z subunits are as defined above, and each Y subunit independently represents a neutral amino acid —C(O)—(CHR)—NH—, where R is a neutral side chain selected from substituted or unsubstituted alkyl, alkenyl, alkynyl, aryl, and aralkyl, wherein said neutral side chain, when selected from substituted alkyl, alkenyl, and alkynyl, includes at most one heteroatom for every two, preferably every four, and more preferably every six carbon atoms. The agent may be conjugated to the peptide via a Y subunit, a cysteine subunit, or an uncharged, non-amino acid linker moiety.

The compound to be delivered is preferably a biologically active agent, e.g. a therapeutic or diagnostic agent, although it may be a compound employed for detection, such as a fluorescent compound. Biologically active agents include drug substances selected from biomolecules, e.g. peptides, proteins, saccharides, or nucleic acids, particularly antisense oligonucleotides, or "small molecule" organic or inorganic compounds. A "small molecule" compound may be defined broadly as an organic, inorganic, or organometallic compound which is not a biomolecule as described above. Typically, such compounds have molecular weights of less than 1000, or, in one embodiment, less than 500.

In one embodiment, the agent to be delivered does not include single amino acids, dipeptides, or tripeptides. In another embodiment, it does not include short oligopeptides; that is, oligopeptides having fewer than six amino acid subunits. In a further embodiment, it does not include longer oligopeptides; that is, oligopeptides having between seven and 20 amino acid subunits. In a still further embodiment, it does not include polypeptides, having greater than 20 amino acid subunits, or proteins.

The transport peptide is effective to enhance the transport of the agent into a cell relative to the agent in unconjugated form, and relative to the agent conjugated to a corresponding peptide lacking the Y subunits. Preferably, transport is enhanced by a factor of at least two, more preferably by a factor of at least five, and most preferably by a factor of at least ten.

B. Nucleic Acid Analogs

Nucleic acid analogs included in the conjugates of the invention are substantially uncharged synthetic oligomers capable of base-specific binding to a target sequence of a polynucleotide, e.g. antisense oligonucleotide analogs. Such analogs include, for example, methylphosphonates, peptide nucleic acids, substantially uncharged N3'→P5' phosphoramidates, and morpholino oligomers.

A nucleic acid analog having a "substantially uncharged" backbone (also referred to as a "substantially uncharged nucleic acid analog") is one having at most one charged (at physiological pH) intersubunit linkage for every four uncharged (at physiological pH) linkages, preferably at most one for every eight, and more preferably at most one for every sixteen uncharged linkages. In a preferred embodiment, the nucleic acid analogs described herein are fully uncharged.

The base sequence of the nucleic acid analog, provided by base pairing groups supported by the analog backbone, can be any sequence, where the supported base pairing groups include standard or modified A, T, C, G and U bases or the non-standard inosine (I) and 7-deaza-G bases.

A preferred nucleic acid analog is a morpholino oligomer, i.e. an oligonucleotide analog composed of morpholino subunit structures of the form shown in FIG. 1, where (i) the structures are linked together by phosphorus-containing linkages, one to three atoms long, preferably two atoms long, and preferably uncharged, joining the morpholino nitrogen of one subunit to the 5' exocyclic carbon of an adjacent subunit, and (ii) P$_i$ and P$_j$ are purine or pyrimidine base-pairing moieties effective to bind, by base-specific hydrogen bonding, to a base in a polynucleotide. The purine or pyrimidine base-pairing moiety is typically adenine, cytosine, guanine, uracil or thymine. The synthesis, structures, and binding characteristics of morpholino oligomers are detailed in U.S. Pat. Nos. 5,698,685, 5,217,866, 5,142, 047, 5,034,506, 5,166,315, 5,521,063, and 5,506,337, all of which are incorporated herein by reference.

Figure 2B:
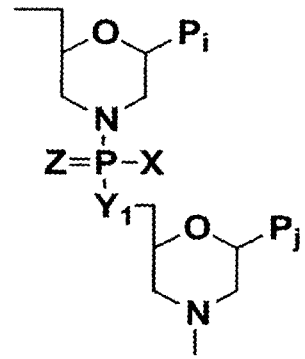
Figure 2C:
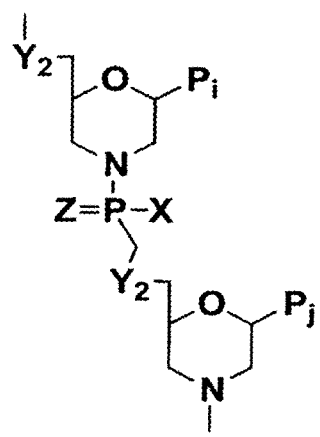
Figure 2D:
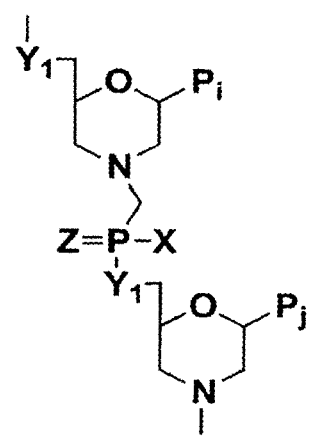

The subunit shown FIG. 1B, having a two-atom linkage, is used for 6-atom repeating-unit backbones, as shown in FIG. 2B. In these structures, the atom Y$_1$ linking the 5' morpholino carbon to the phosphorus group may be sulfur, nitrogen, carbon or, preferably, oxygen. The X moiety pendant from the phosphorus is any stable group which does not interfere with base-specific hydrogen bonding. Preferred groups include alkyl, alkoxy, thioalkoxy, and alkyl amino, including cyclic amines, all of which can be variously substituted, as long as base-specific bonding is not disrupted. Alkyl, alkoxy and thioalkoxy preferably include 1-6 carbon atoms. Alkyl amino preferably refers to lower alkyl ($C_1$ to $C_6$) substitution, and the cyclic amines are preferably 5- to 7-membered nitrogen heterocycles optionally containing 1-2 additional heteroatoms selected from oxygen, nitrogen, and sulfur. Z is sulfur or oxygen, and is preferably oxygen.

A preferred morpholino oligomer is a phosphorodiamidate-linked morpholino oligomer, referred to herein as a PMO. Such oligomers are composed of morpholino subunit structures of the form shown in FIG. 2B, where the structures are linked together by phosphorodiamidate linkages, where X=$NH_2$, NHR, or $NR_2$ (where R is lower alkyl, preferably methyl), Y=O, and Z=O, joining the morpholino nitrogen of one subunit to the 5' exocyclic carbon of an adjacent subunit, $P_i$ and $P_j$ are purine or pyrimidine base-pairing moieties effective to bind, by base-specific hydrogen bonding, to a base in a polynucleotide. Also preferred are structures having an alternate phosphorodiamidate linkage, where, in FIG. 2B, X=lower alkoxy, such as methoxy or ethoxy, Y=NH or NR, where R is lower alkyl, and Z=O.

Desirable chemical properties of the morpholino-based oligomers include the ability to selectively hybridize with a complementary-base target nucleic acid, including target RNA, with high Tm, even with oligomers as short as 8-14 bases, the ability to be actively transported into mammalian cells, and the ability of an oligomer:RNA heteroduplex to resist RNAse degradation.

A "substantially uncharged" morpholino oligomer includes at most one charged intersubunit linkage for every four, preferably for every eight, and more preferably for every sixteen, uncharged intersubunit linkages. Any charged linkages are preferably charged phosphoramidate (or thiophosphoramidate) linkages, e.g. a linkage as shown in FIG. 2B where X is $O^-$ or $S^-$. Preferably, the morpholino oligomers are fully uncharged.

In a preferred embodiment, the morpholino oligomer is about 8-40 subunits in length. More typically, the oligomer is about 8-20, about 8-16, about 10-30, or about 12-25 subunits in length. For some applications, such as antibacterial, short oligomers, e.g. from about 8-12 subunits in length, can be especially advantageous, particularly when attached to a peptide transporter as disclosed herein.

C. Linkers

The transport peptide can be linked to the agent to be delivered by a variety of methods available to one of skill in the art. Exemplary methods are provided in Examples 2-5 below and illustrated in FIGS. 4A-D. In one embodiment, the transport peptide contains a single cysteine residue whose side chain thiol is used for linking, such as shown in FIGS. 4B and 4C, where the cysteine is a terminal cysteine. The linker may also be provided by a hydrophobic subunit such as those defined as Y, e.g. a β-alanine or longer non-α amino acid subunit, as shown, for example, in FIG. 4D.

As discussed further below, the linkage point can be at various locations along the transporter. In selected embodiments, it is at a terminus of the transporter. Typically, it is adjacent (or even between) the hydrophobic residues of the transporter. Multiple transporters can be attached to a single compound if desired; alternatively, multiple compounds can be conjugated to a single transporter.

Figure 4A:
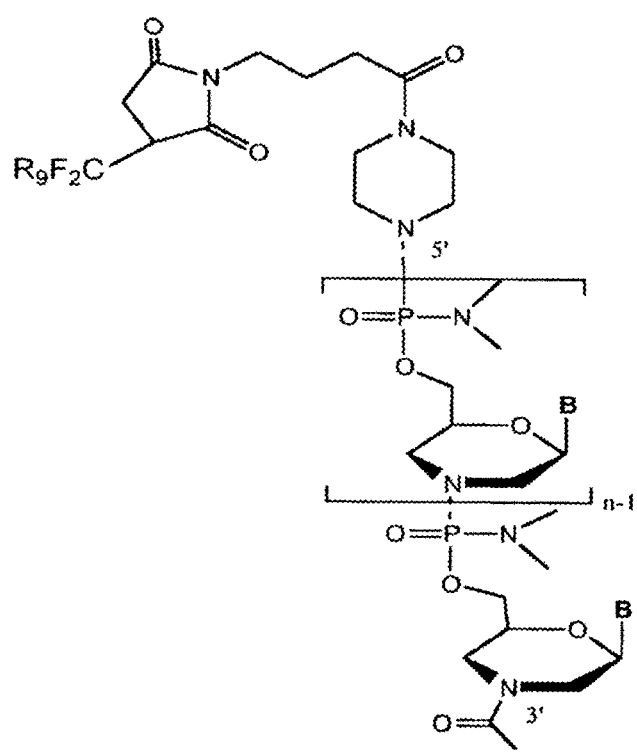
FIGS. 4A-D show oligomer-transporter conjugates and methods of their preparation, where FIG. 4C (SEQ ID NO:43) shows preparation of an in vivo cleavable conjugate.
Figure 4B:
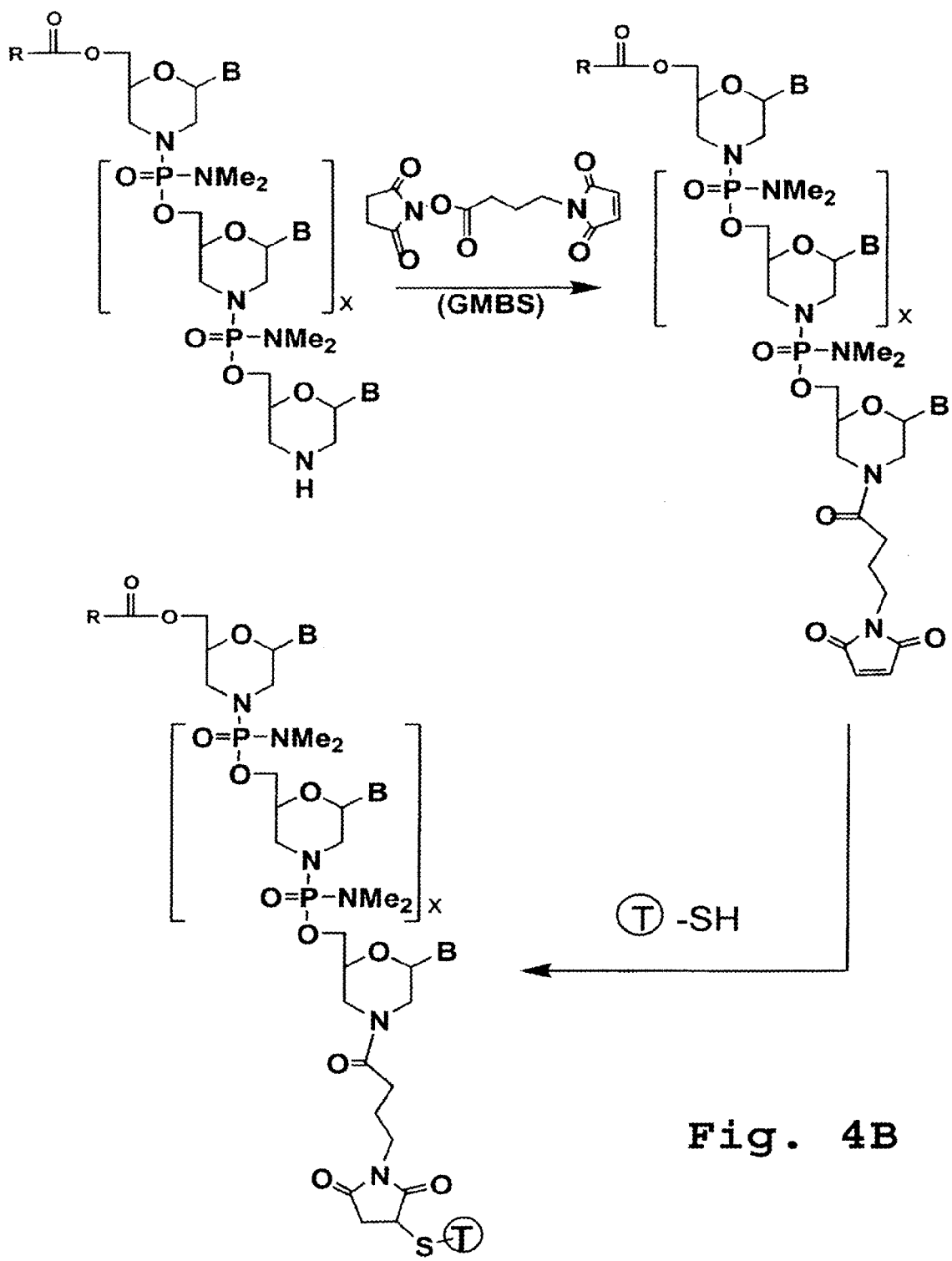
Figure 4C:
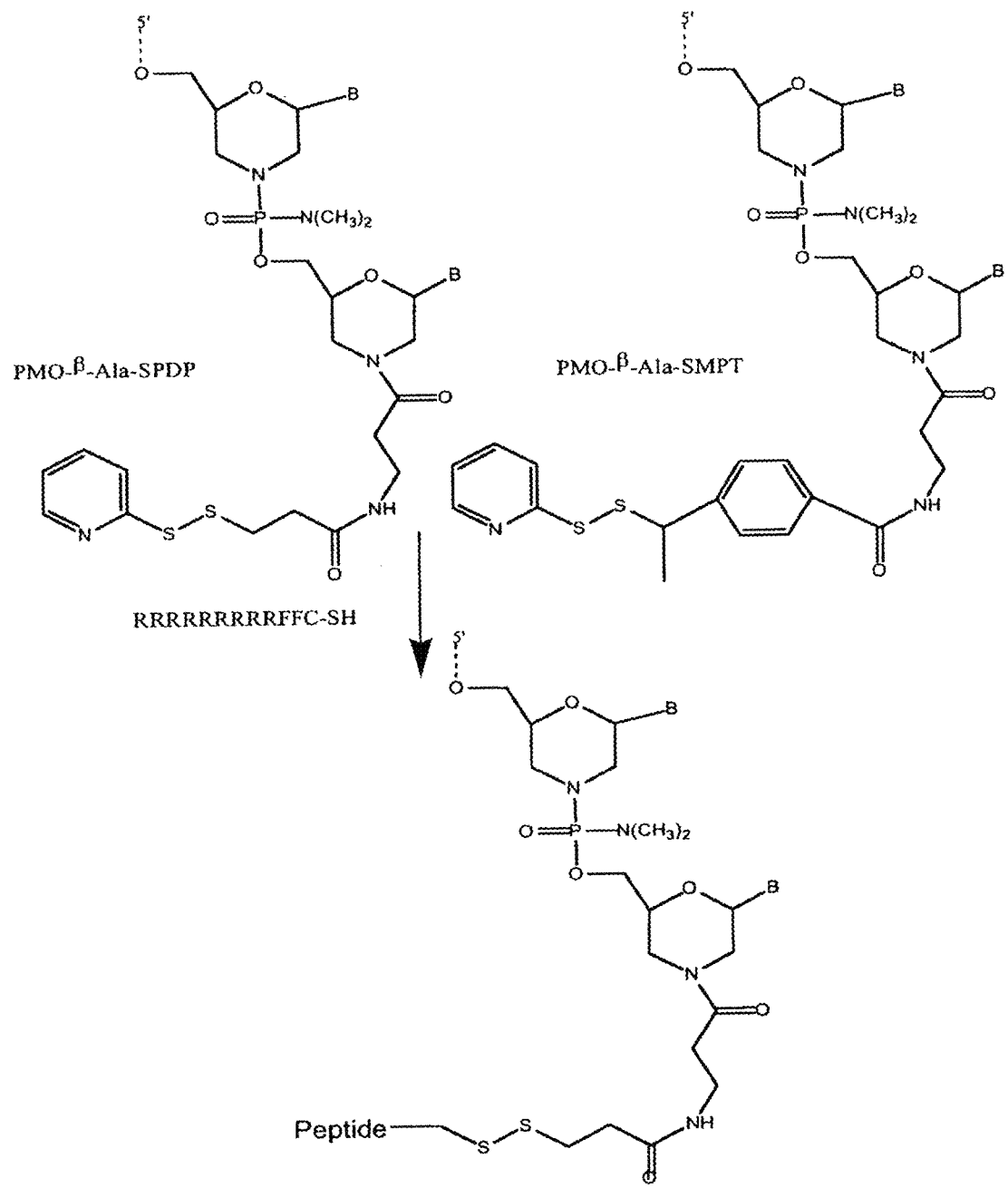
Figure 4D:
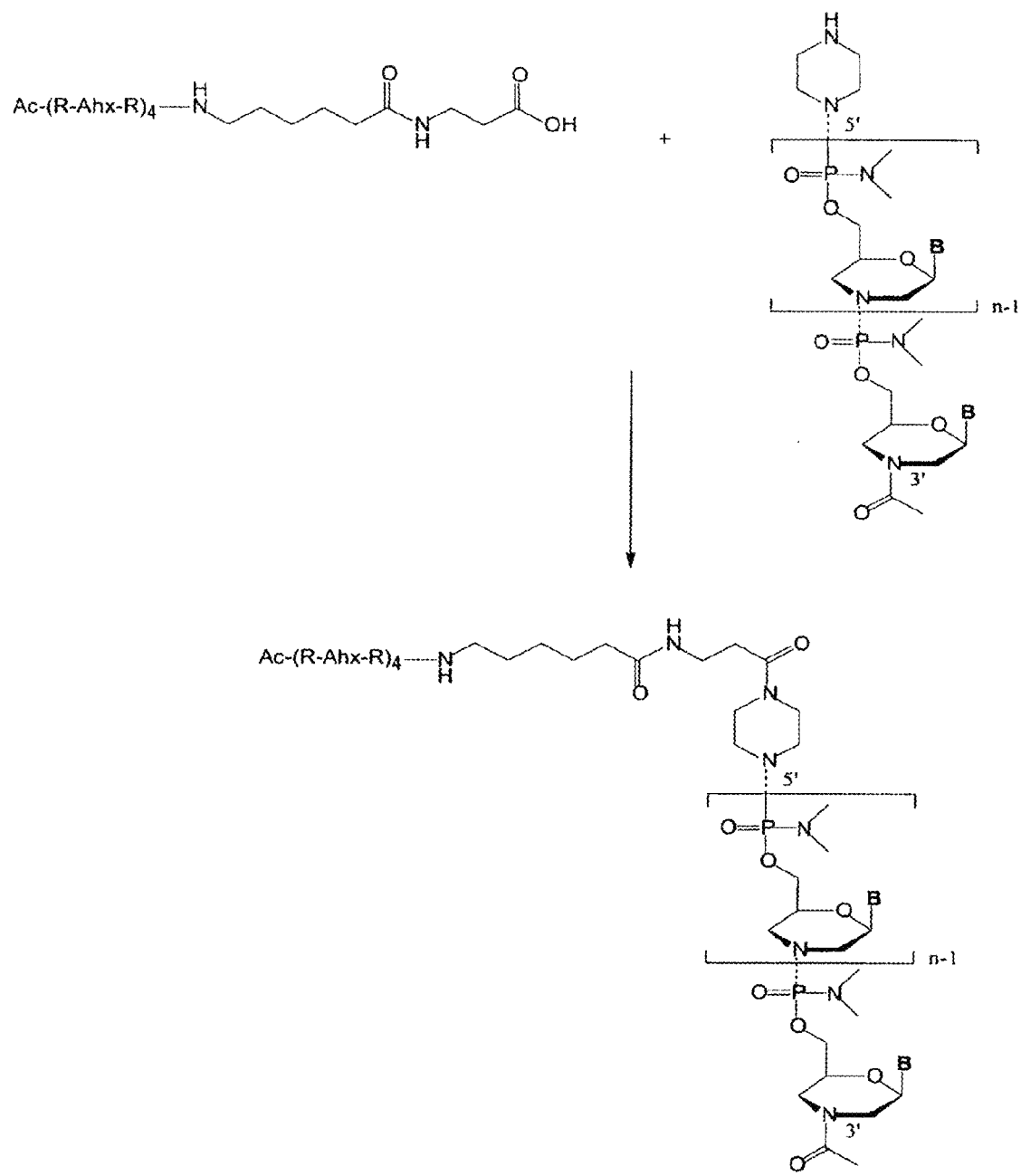

When the compound is a PMO, the transporter can be attached at the 5' end of the PMO via an amine capping moiety, as described in Examples 2-3 and illustrated in FIGS. 4A and 4D. Alternatively, the transporter may be attached at the 3' end, e.g. via a morpholino ring nitrogen, as described in Example 4 and shown in FIG. 4B, or via the side chain of an intersubunit linkage, either at a terminus or an internal linkage.

The linker between the transport peptide and the PMO may also consist of natural or non-natural amino acids (e.g., 6-aminohexanoic acid or β-alamine) added to the peptide at the C-terminal and as described in Example 2. The linker may also comprise a direct bond between the carboxy terminus of a transporter peptide and an amine or hydroxy group of the PMO, formed by condensation promoted by e.g. carbodiimide.

In general, the linker may comprise any nonreactive moiety which does not interfere with transport or function of the conjugate. The linker preferably includes a chain of up to about sixteen atoms, including lengths of up to 12 or up to 8 atoms, comprising linkages selected from alkyl, ether (e.g. PEG linkages), thioether, ester, amide, amino, carbamate, or combinations thereof. More preferably, the linkages are selected from alkyl, ether, and amide, when linkages which are stable (non-cleavable) in vivo are desired.

Linkers can be selected from those which are non-cleavable under normal conditions of use, e.g., containing an ether, thioether, amide, or carbamate bond. In other embodiments, it may be desirable to include a linkage between the transporter moiety and compound which is cleavable in vivo. Bonds which are cleavable in vivo are known in the art and include, for example, carboxylic acid esters, which are hydrolyzed enzymatically, and disulfides, which are cleaved in the presence of glutathione. It may also be feasible to cleave a photolytically cleavable linkage, such as an ortho-nitrophenyl ether, in vivo by application of radiation of the appropriate wavelength.

For example, the preparation of a conjugate having a disulfide linker, using the reagent N-succinimidyl 3-(2-pyridyldithio) propionate (SPDP) or succinimidyloxycarbonyl α-methyl-α-(2-pyridyldithio) toluene (SMPT), is described in Example 5 and illustrated in FIG. 4C. Exemplary heterobifunctional linking agents which further contain a cleavable disulfide group include N-hydroxysuccinimidyl 3-[(4-azidophenyl)dithio]propionate and others described in Vanin, E. F. and Ji, T. H., *Biochemistry* 20:6754-6760 (1981).

D. Exemplary Peptides and Conjugates

A Table of sequences of exemplary transport peptides and PMOs discussed in the following sections is provided below. In general, the peptides include an N-terminal amino group and C-terminal amide (e.g., $NH_2$—CYGRKKRRQRRR—$CONH_2$) (SEQ ID NO: 11) or free carboxyl group (e.g., $NH_2$—CYGRKKRRQRRR—COOH) (SEQ ID NO: 11), or they include an N-terminal acetamide and C-terminal acid (e.g., Ac—NH(RAhxR)$_4$AhxβAla-OH) (SEQ ID NO: 44). The "Y" residues of peptides of the invention designated by SEQ ID NOs: 13-32 are indicated in boldface, and internal cysteine residues used for linkage to the PMO are shown in italics. (When no cysteine linker is shown, the peptide is typically linked via its C-terminus, i.e. at the right side as shown.)

Exemplary peptides containing 6-aminohexanoic acid (Ahx) subunits are shown in Table 1 as SEQ ID NOs: 33-41. The structure of the (RAhxR)$_4$ transport peptide (SEQ ID NO:34) conjugated to a PMO via an Ahx-βAla linker is shown in FIG. 4D.

TABLE 1

| PMO | Sequence (5' to 3') | SEQ ID NO: |
|---|---|---|
| 705 | 5'- CCT CTT ACC TCA GTT ACA-acetyl-3' | 1 |
| 705-FL | 5'- CCT CTT ACC TCA GTT ACA-fluorescein-3' | 1 |
| 705$_{2MM}$ | 5'- CCT CTT AAC TCC GTT ACA-acetyl-3' | 2 |
| 705$_{4MM}$ | 5'- CCT ATT AAC TCC GTT CCA-acetyl-3' | 3 |
| 705$_{SCR}$ | 5'- CTC TCT CAC CAT TGA CAT-acetyl-3' | 4 |
| c-myc | 5'- ACG TTG AGG GGC ATC GTC GC-acetyl-3' | 5 |
| DEN5'CS | 5'- CGT TTC AGC ATA TTG AAA GG-3' | 6 |
| DEN3'CS | 5'- CCC AGC GTC AAT ATG CTG-3' | 7 |
| DEN AUG | 5'- GGT TAT TCA TCA GAG ATC TG-3' | 8 |
| MHV lab | 5'- GCC CAT CTT TGC CAT TAT GC-3' | 9 |
| DSscr | 5'- AGT CTC GAC TTG CTA CCT CA-3 | 10 |

| Peptide | Sequence (N-terminal to C-terminal) | SEQ ID NO: |
|---|---|---|
| pTat | CYGRKKRRQRRR | 11 |
| rTat | RRRQRRKKR | 12 |
| R$_9$F$_2$ | RRRRRRRRRFF | 13 |
| 2d-R$_9$F$_2$ | $_D$R$_D$RRRRRRRRFF (mixed isomer) | 14 |
| D-R$_9$F$_2$ | $_D$R$_D$R$_D$R$_D$R$_D$R$_D$R$_D$R$_D$R$_D$R$_D$F$_D$F$_D$ (D-isomer) | 15 |
| R$_9$CF$_2$ | RRRRRRRRRCFF | 16 |
| R$_8$CF$_2$R | RRRRRRRRCFFR | 17 |
| R$_6$CF$_2$R$_3$ | RRRRRRCFFRRR | 18 |
| R$_5$FCFR$_4$ | RRRRRFCFRRRR | 19 |
| R$_5$F$_2$R$_4$ | RRRRRFFRRRR | 20 |
| R$_4$CF$_2$R$_5$ | RRRRCFFRRRRR | 21 |
| R$_2$CF$_2$R$_7$ | RRCFFRRRRRRR | 22 |
| CF$_2$R$_9$ | CFFRRRRRRRRR | 23 |
| CR$_9$F$_2$ | CRRRRRRRRRFF | 24 |
| F$_2$R$_9$ | FFRRRRRRRRR | 25 |
| R$_5$F$_2$CF$_2$R$_4$ | RRRRRFFCFFRRRR | 26 |
| R$_9$I$_2$ | RRRRRRRRRII | 27 |
| R$_8$F$_3$ | RRRRRRRRFFF | 28 |
| R$_9$F$_4$ | RRRRRRRRRFFFF | 29 |
| R$_8$F$_2$ | RRRRRRRRFF | 30 |
| R$_6$F$_2$ | RRRRRRFF | 31 |
| R$_5$F$_2$ | RRRRRFF | 32 |
| (RRAhx)$_4$ | RRAhxRRAhxRRAhxRRAhx | 33 |
| (RAhxR)$_4$ | RAhxRRAhxRRAhxRRAhxR | 34 |
| (AhxRR)$_4$ | AhxRRAhxRRAhxRRAhxRR | 35 |
| (RAhx)$_6$ | RAhxRAhxRAhxRAhxRAhxRAhx | 36 |
| (RAhxR)$_3$ | RAhxRRAhxRRAhxR | 37 |

TABLE 1-continued

| | | |
|---|---|---|
| (RAhxR)$_2$R | RAhxRRAhxRR | 38 |
| (RAhxR)$_2$ | RAhxRRAhxR | 39 |
| (RKAhx)$_4$ | RKAhxRKAhxRKAhxRKAhx | 40 |
| (RHAhx)$_4$ | RHAhxRHAhxRHAhxRHAhx | 41 |

II. Biological Activity of Transporter-PMO Conjugates

The peptide transporters described herein facilitate the delivery of substantially uncharged oligomers into living eukaryotic cells, as well as significantly enhancing antisense activity, as demonstrated below for PMOs. In one embodiment, the oligomer is a substantially uncharged morpholino oligomer as described above.

Cellular delivery can involve both cytoplasmic and nuclear compartments of the cell. Accordingly, in selected embodiments, the antisense oligomer includes a base sequence effective to hybridize to a target sequence which includes a splice site in a selected preprocessed mRNA (pre-mRNA). The antisense oligomer may also include a base sequence effective to hybridize to a target sequence which includes a translation start site in a selected mRNA. The antisense oligomer may also include a base specific sequence effective to hybridize to a target sequence required for viral replication. In another aspect, the antisense oligomer may be an antibacterial agent, e.g. by targeting ribosomal RNA or other bacterial nucleic acids, as described, for example, in co-owned PCT Pubn. Nos. WO 01/49775 and WO 01/42457 (US Pubn. No. 2002/0082226), which are incorporated herein by reference.

As demonstrated herein, the transport peptides as described above greatly enhance cell entry of attached compounds, relative to uptake of the compound in the absence of the attached peptide transport moiety, and relative to uptake by an attached transport moiety lacking the Y subunits. Such enhanced uptake is preferably evidenced by at least a one-fold increase, and preferably a more than two-fold increase, in the uptake of the compound into mammalian cells, relative to uptake of the agent by an attached transport moiety lacking the Y subunits. Uptake is preferably enhanced at least twenty fold, and more preferably at least forty fold, relative to the unconjugated compound.

Uptake is preferably measured in HeLa cells or in mononuclear blood cells, particularly lymph or spleen derived cells, such as lymphocytes or fibroblasts, by processes such as described in Materials and Methods, below, for HeLa cells, under the headings "Cell Culture" through "Flow Cytometry". See also Example 6, Example 9, Section A below for evaluation of transport only, and Section B below for evaluation of transport and antisense activity.

A further benefit of the transport moiety is the enhancement of binding of an attached nucleic acid analog to its target sequence. The transport moieties of the invention are shown herein to lower the concentration of an uncharged antisense oligomer effective to achieve antisense activity, as measured in both tissue culture and cell-free systems. Tissue culture experiments provide indications of enhanced antisense activity, due to enhanced intracellular delivery, enhanced antisense activity, e.g. binding of the antisense oligomer to its target sequence, or a combination of these phenomena.

Cell-free translation systems provide a means to assess, independently of transport, the enhancing effect of the conjugated peptide on the antisense oligomer's ability to bind to its target and, through steric blocking, inhibit translation of downstream sequences (or inhibit aberrant splicing, as in the assay of Example 6). Cell-free translation assays designed to test the antisense effect of R$_9$F$_2$-PMO (SEQ ID NO.:13-PMO) and (RAhxR)$_4$-PMO (SEQ ID NO.:34-PMO) conjugates demonstrate between 10 fold and 500 fold improvement in antisense activity compared to the unconjugated PMO (see, e.g., Example 8 and FIGS. 21-23 and 28). The term "enhancing the translation inhibiting ability" or "enhanced translation inhibiting ability" provided by the conjugated peptide, as used herein, preferably refer to antisense (translation inhibiting) activity as measured in such a cell free system, such as described in Materials and Methods, below, under the heading "Cell-free translations assays". See also Example 9 and Section C below.

A. Transporter-Mediated Delivery of Morpholino Oligomers into Cells

The cellular uptake of three test substances, including (1) unconjugated PMO (SEQ ID NO: 1), also designated herein as "705" or "PMO 705"), (2) a mixture of unconjugated PMO and the transport peptide R$_9$F$_2$ (SEQ ID NO:13)-C, and (3) a covalent conjugate of the PMO and the transport peptide (R$_9$F$_2$-C-705) (SEQ ID NO.:43-SEQ ID NO: 1), were determined by fluorescent microscopy in four cell lines: HeLa pLuc705 derived from HeLa S3, HeLa, NIH3T3, and Jurkat. HeLa pLuc/705 (Kang, Cho et al. 1998) is a HeLa S3 cell line stably transfected with a plasmid carrying the luciferase coding sequence interrupted by a mutated human β-globin intron 2 (Gene Tools, Philomath, Oreg.). Other cell lines were obtained from ATCC (Manassas, Va.). The PMO's were 3'-labeled with fluorescein as described in Example 1. To avoid artifacts, all fluorescent images were taken from live cells, and no fixative agent or mounting media were used.

In all four cell lines, the fluorescent images of cells treated with 705-FL (SEQ ID NO:21) alone, or with the mixture of unconjugated 705-FL PMO (SEQ ID NO: 1) and R$_9$F$_2$-C (SEQ ID NO:43), were essentially devoid of fluorescence. In cells treated with R$_9$F$_2$-C-PMO (SEQ ID NO.:43-SEQ ID NO: 1) conjugate, fluorescence was observed in 100% of the cells, although patterns varied among the different cell lines as follows. The NIH3T3 cells had very bright and diffused cytosolic and nuclear fluorescence with fewer punctate spots than other cell lines. The HeLa cells had mostly diffused fluorescence with more distinct punctate spots than NIH3T3. The HeLa S3 cells appeared to have less intense cytosolic diffuse fluorescence but with a very bright fluorescent spot localized near or in the nucleus. The Jurkat cells had the lowest level of fluorescence among these cell lines.

The association of the conjugate with cells is a fairly rapid process. As shown in FIG. 5A, fluorescence of cells incubated with $R_9F_2C$-PMO (SEQ ID NO.:43-SEQ ID NO: 1) increased within minutes and reached maximum intensity between 30-45 minutes over a 900 minute study period. The fluorescence of cells incubated at 37° C. was similar to those incubated at 17° C. over a concentration range of 0.1 to 5 µM (FIG. 5B). The adsorption appeared to be saturable, with an increase in fluorescence observed between 0.1-1 µM, but not between 1-5 µM.

As reported previously (Moulton, Hase et al. 2003), the majority of Tat peptide that becomes associated with cell membranes is not internalized. Because membrane-bound conjugate may artificially enhance the appearance of cellular fluorescence, trypsin treatment was used in the present case to reduce or eliminate the contribution from membrane-bound conjugate (Moulton, Hase et al. 2003; Richard, Melikov et al. 2003).

Thus, HeLa or NIH3T3 cells were incubated with conjugate, then trypsinized, as described below in Materials and Methods, washed, and replated. The trypsinized cells had much less fluorescence than non-trypsinized cells (FIG. 6), though patterns of fluorescence were similar.

As also shown in FIG. 6, both L-transporter and D-transporter conjugates gave identical association and internalization profiles; therefore, the decrease in fluorescence upon trypsinization cannot be attributed solely to trypsin digestion of $R_9F_2C$ (SEQ ID NO.:43) peptide. This suggests that the conjugate associates with membrane protein(s), which are digested by trypsin.

Figure 7A:
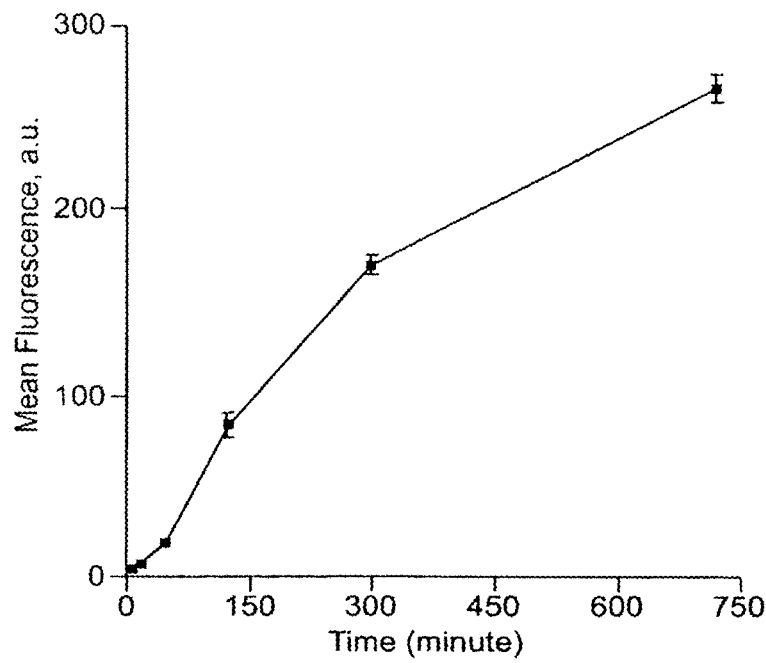
FIG. 7A shows internalization over time, as determined by flow cytometry in cells incubated with 1 µM fluorescein-labeled peptide-PMO conjugate ($R_9F_2C$-705-FL) (SEQ ID NO.:43-SEQ ID NO: 1) and then treated with trypsin.
Figure 7B:
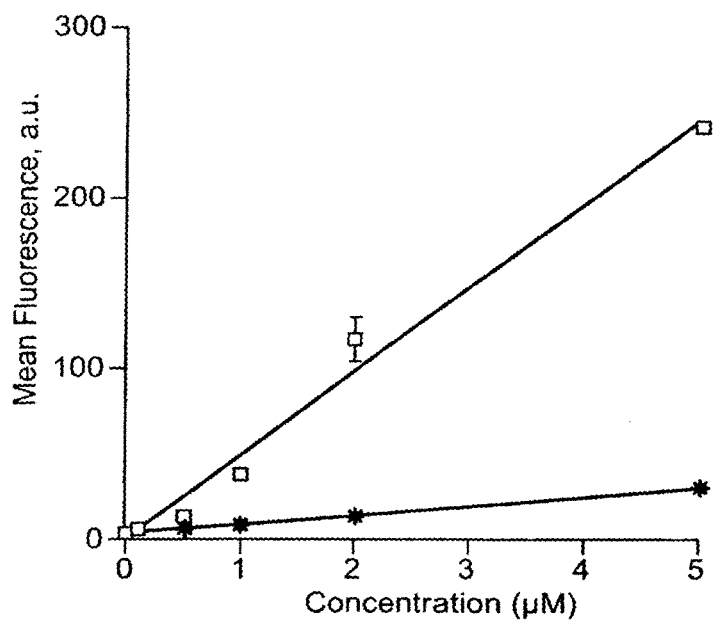
FIG. 7B shows internalization with increasing concentration, as determined by flow cytometry, in cells treated with $R_9F_2C$-705-FL (SEQ ID NO: 43-SEQ ID NO: 1), at 37° C. ( ) or 17° C. (*) for 70 minutes, and then treated with trypsin.

Having shown that trypsin can effectively remove most membrane-bound conjugate, factors affecting internalization of the conjugate could be studied in trypsinized cells by flow cytometry. As shown in FIG. 7A, gradual increases in fluorescence, due to conjugate internalization, are observed up to 700 minutes from incubation. Internalization is also seen to be temperature- and concentration-dependent, as shown in FIG. 7B. The profile shown in FIG. 7B is similar to that shown by the endocytosis marker FM4-64 (a fluorescent, lipophilic dye which labels the plasma membrane and is then endocytosed in a time-, temperature-, and energy-dependent manner). Internalization of conjugate was almost completely inhibited in cells pre-incubated with the metabolic inhibitor, $NaN_3$, indicating that internalization of the peptide-PMO conjugate is an energy dependent process.

B. Antisense Activity in Cell Culture

Various oligomer-transporter moiety conjugates in accordance with the invention were tested for antisense activity in vitro (Example 6). The data described below was obtained by targeting a β-globin splice correction sequence fused to luciferase. Specifically, the assay uses HeLa cells stably transfected with plasmid pLuc/705, which has a luciferase gene interrupted by a human β-globin intron mutated at nucleotide 705, thus causing incorrect splicing. An antisense oligonucleotide targeting the 705 splice site, when delivered effectively, corrects splicing and allows luciferase expression. For further description of the plasmid and assay, see e.g. Kang, Cho et al. 1998; Yoo, Sazani et al. 1999. Because the cell nucleus is the site of pre-mRNA splicing, these data demonstrate delivery of the oligomer to the cell nucleus.

Figure 8:
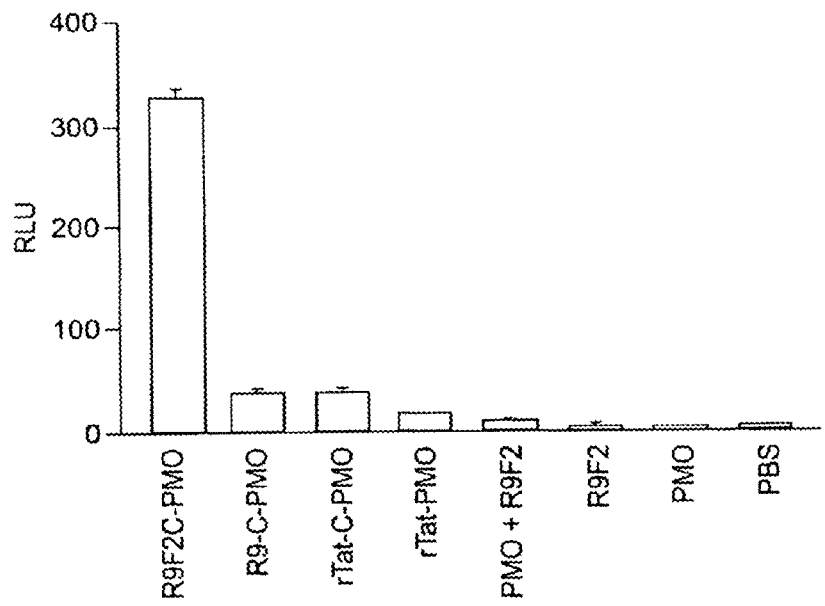
FIG. 8 shows the level of luciferase production observed (expressed as RLU) in HeLa pLuc705 cells after 6 hrs incubation with 25 µM of each of the following: the PMO-transporter conjugates $R_9F_2C$—PMO (SEQ ID NO.:43-PMO); $R_9C$-PMO (SEQ ID NO: 47-PMO); rTat (57-49)-C-PMO (SEQ ID NO: 50); and rTat (57-49)-PMO (SEQ ID NO.:12-PMO); a mixture of $R_9F_2C$ (SEQ ID NO.:43) and PMO; $R_9F_2C$ (SEQ ID NO.:43) alone; PMO alone; and PBS buffer. The PMO used was the 705 sequence (SEQ ID NO: 1).

A conjugate of an 18-mer antisense PMO (SEQ ID NO: 1) with the oligopeptide rTat (57-49) (SEQ ID NO:12) was previously shown to inhibit aberrant splicing in this assay (Moulton, Hase et al. 2003). Comparative assays were carried out using rTat (57-49) (SEQ ID NO: 12) conjugates and conjugates containing transporter molecules of the invention, as shown in FIG. 8.

As shown in the Figure, a conjugate consisting of the antisense PMO linked, via a cysteine residue, to a peptide having the sequence $Arg_9Phe_2$ ($R_9F_2$, SEQ ID NO:13) was much more effective in suppressing aberrant splicing than conjugates containing the peptides rTat (57-49) (RRRQR-RKKR) (SEQ ID NO.:12) and $R_9$ (SEQ ID NO: 51), also linked to the PMO via a cysteine residue.

Figure 9:
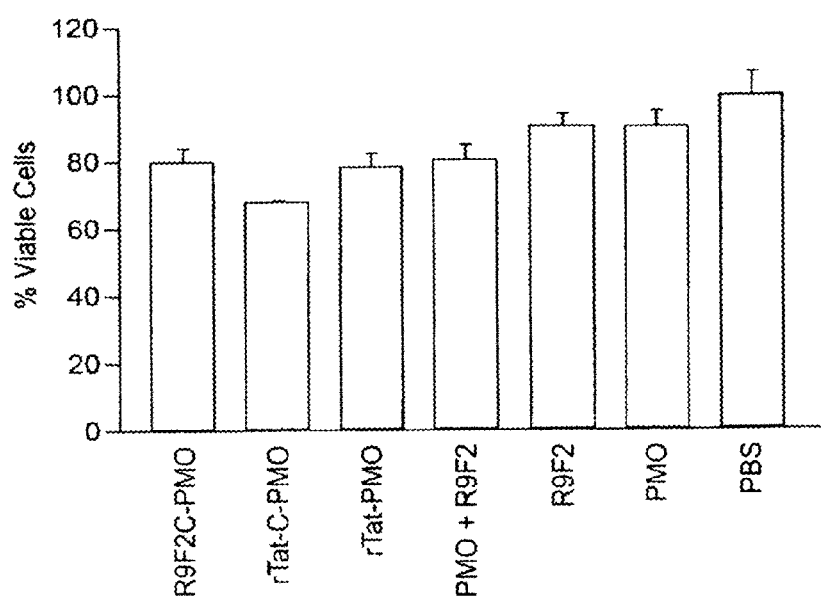
FIG. 9 shows viability of HeLa cells after 24 hrs incubation with 25 µM of the compositions listed for FIG. 8.

FIG. 9 gives the level of viable HeLa cells after 24 hrs incubation with several of these conjugates at a concentration of 25 µM, showing the low toxicity of the conjugates.

FIGS. 10-14 show the effect of various structural modifications of the transporter on the antisense activity of the PMO-transporter conjugates. In each Figure, results are expressed in relative light units normalized to microgram of protein, based on luciferase expression in the pLuc705 assay described above. In the conjugates represented in these figures, the PMO is attached, via a cysteine residue, at the C-terminus or right side of the transporter sequence as written and to the 5'-terminus, or left side as written, of the PMO.

Figure 10:
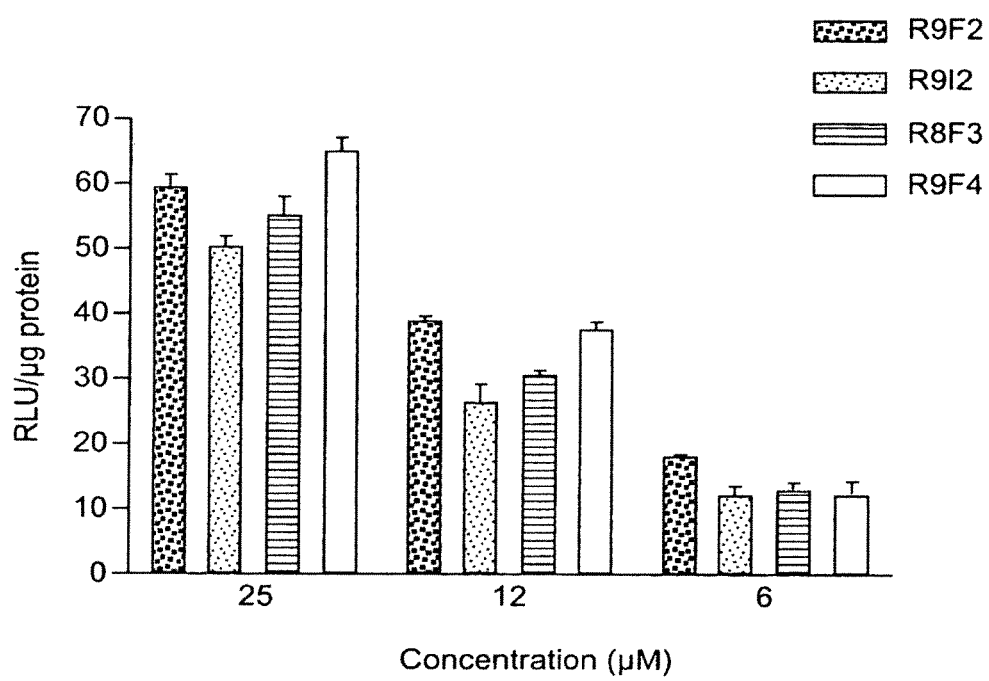
FIG. 10 shows the level of luciferase production normalized to microgram of protein (RLU/µg protein) observed in HeLa Luc705 cells after 24 hrs incubation with conjugates of PMO(705) (SEQ ID NO: 1) with $R_9F_2$ (SEQ ID NO.:13), $R_9I_2$ (SEQ ID NO.:27), $R_8F_3$ (SEQ ID NO.:28), and $R_9F_4$ (SEQ ID NO.:29), respectively, where in each case the PMO was attached via a cysteine residue at the C-terminus (right side) of the peptide transporter as shown.

FIG. 10 shows the effect of varying the nature or length of the hydrophilic segment of the transporter. As shown, phenylalanine (Phe or F)-containing transporters appeared to be more effective than isoleucine (Ile or I)-containing transporters. Increasing the length of the hydrophobic segment from 2 to 3 to 4 amino acid subunits did not appear to increase effectiveness.

Figure 11A:
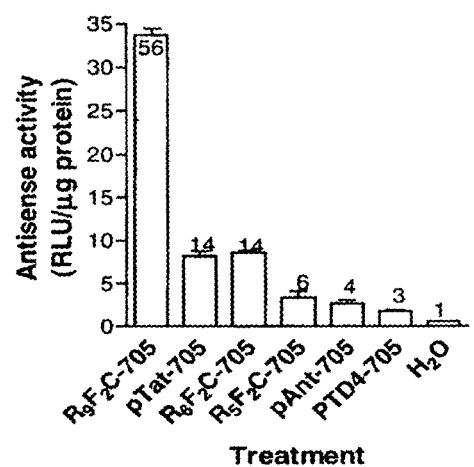
FIG. 11 shows (A) the level of luciferase production (RLU/µg protein), as in FIG. 10, and (B) fluorescence in HeLa pLuc705 cells after 24 hrs incubation with conjugates of PMO(705) (SEQ ID NO: 1) with $R_9F_2$ (SEQ ID NO.:13), $R_6F_2$ (SEQ ID NO.:31), and $R_5F_2$ (SEQ ID NO.:32) where in each case the PMO was attached via a cysteine residue at the C-terminus of the peptide transporter.
Figure 11B:
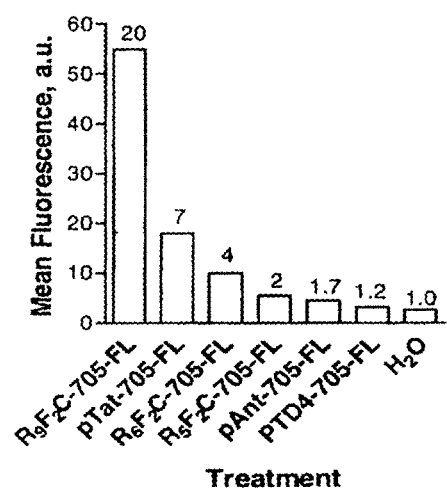

The total number of arginines in the transporter appears to be significant, in view of the data shown in FIG. 11. As shown therein, in oligopeptides of the series RnF2, oligopeptides where n was 6 or less were much less effective than those where n was 8 or 9. See also Moulton, Nelson et al., 2004, which is incorporated herein in its entirety by reference.

Figure 12:
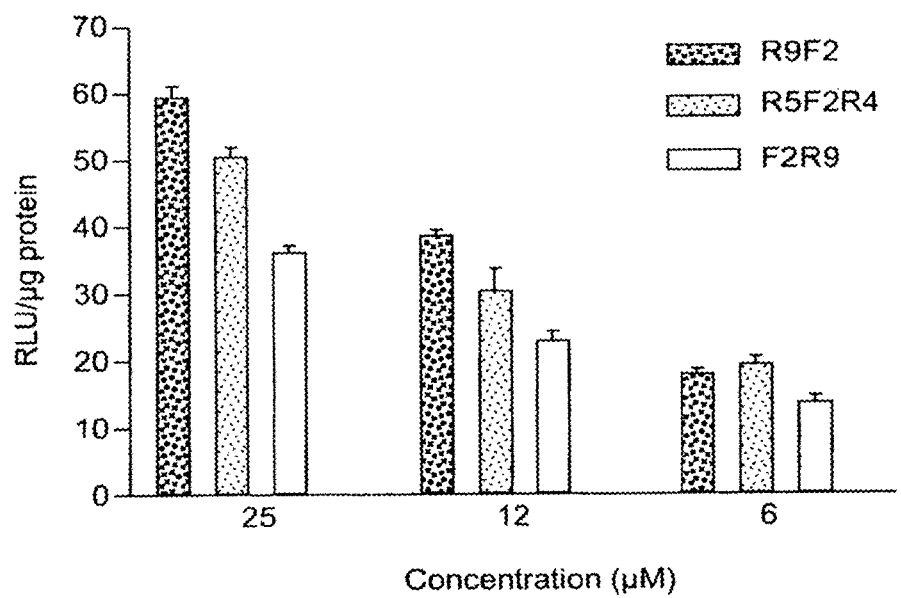
FIG. 12 shows the level of luciferase production (RLU/μg protein), as in FIG. 10, in HeLa pLuc705 cells after 24 hrs incubation with conjugates of PMO with $R_9F_2$ (SEQ ID NO.: 13), $R_5F_2R_4$ (SEQ ID NO.:20), and $F_2R_9$ (SEQ ID NO.:25), respectively, where in each case the PMO was attached via a cysteine residue at the C-terminus of the peptide transporter.

As shown in FIG. 12, the position of the hydrophobic segment can be altered. In the data represented by $F_2R_9$ (SEQ ID NO.:25), the $R_9$ (SEQ ID NO: 51) segment is at the C-terminus and is attached to the PMO. Significantly, the data shows that the sequence of cationic subunits can be non-contiguous ($R_5F_2R_4$) (SEQ ID NO.:20). Further examples are given in FIG. 15, below.

Figure 13:
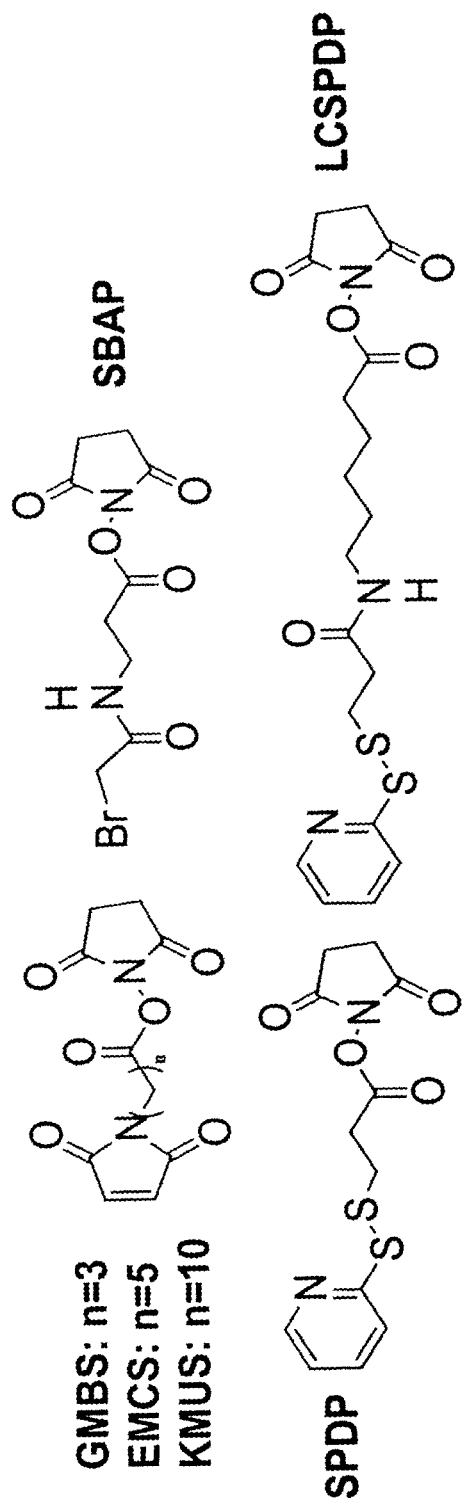
FIG. 13 shows structures of bifunctional cross linkers that may be used to link transport polymers to antisense oligomers.

Table 2 below shows the level of luciferase production (i.e., antisense activity) in HeLa pLuc705 cells after 24 hrs incubation with $R_9F_2$-PMO (SEQ ID NO.:13-SEQ ID NO: 1) conjugates, linked by either a cleavable linker or a non-cleavable linker of various lengths, where in each case the PMO was attached via a cysteine residue at the C-terminus of the peptide transporter. The structures of the bifunctional cross linkers used in this study are shown in FIG. 13. As shown in the Table, the use of a cleavable (disulfide) linker (see e.g. FIG. 4C) had no significant effect on activity. See also Moulton, Nelson et al., 2004.

TABLE 2

Effect of linker on antisense activity of R9F2C-PMO (705-FL) (SEQ ID NO: 43-SEQ ID NO: 1) conjugates

| Treatment | Linker type | Linker length Å | RLU/ug protein range |
|---|---|---|---|
| Vehicle control (H$_2$0) | N/A | N/A | 1 (0.1) |
| R$_9$F$_2$C-705-FL (SEQ ID NO. 43-SEQ ID NO: 1) | thio-maleimide | 6.8 | 102 (4.9) |
| R$_9$F$_2$C-EMCS-705-FL (SEQ ID NO. 43 - EMCS - SEQ ID NO: 1) | thio-maleimide | 9.4 | 141 (4.3) |
| R$_9$F$_2$C-KMUS-705-FL (SEQ ID NO. 43 - KMUS - SEQ ID NO: 1) | thio-maleimide | 15.7 | 171 (14.3) |
| R$_9$F$_2$C-SMPB-705-FL (SEQ ID NO. 43 - SMPB - SEQ ID NO: 1) | thio-maleimide | 11.6 | 123 (2.1) |
| R$_9$F$_2$C-SMCC-705-F (SEQ ID NO. 43 - SMCC - SEQ ID NO: 1) | thio-maleimide | 11.6 | 86 (1.4) |
| R$_9$F$_2$C-SBAP-705-F (SEQ ID NO. 43 - SBAP - SEQ ID NO: 1) | thio-ether | 6.2 | 98 (3.2) |
| R$_9$F$_2$C-SPDP-705-FL (SEQ ID NO. 43 - SPDP - SEQ ID NO: 1) | disulfide | 6.8 | 109 (2.9) |
| R$_9$F$_2$C-LCSPDP-705-FL (SEQ ID NO. 43 - LCSPDP - SEQ ID NO: 1) | disulfide | 15.6 | 181 (7.8) |

Figure 14:
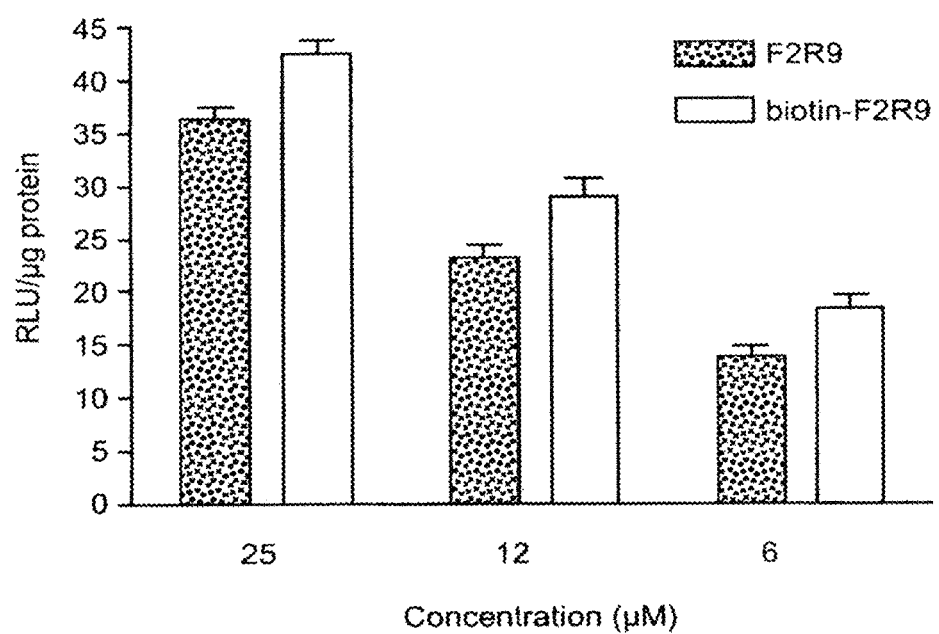
FIG. 14 shows the level of luciferase production (RLU/μg protein), as in FIG. 10, in HeLa pLuc705 cells after 24 hrs incubation with the conjugates R9F2-C-PMO (SEQ ID NO.:43-PMO) and biotin-R9F2-C-PMO (biotin-SEQ ID NO.:43-PMO).

As shown in FIG. 14, attachment of biotin to the conjugate (biotin-R$_9$F$_2$-PMO) (biotin-SEQ ID NO: 13-PMO) appeared to increase activity at high doses after 6 hours incubation (not shown), but little or no effect was seen at 24 hours.

Figure 15:
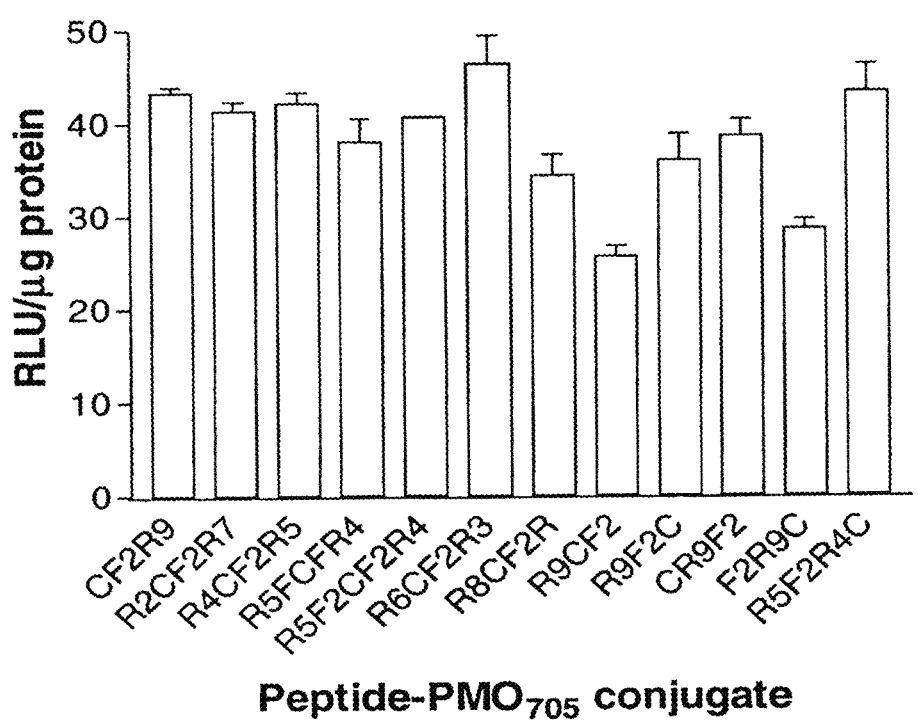
FIG. 15 shows the level of luciferase production (RLU/μg protein), as in FIG. 10, in HeLa pLuc705 cells after 24 hrs incubation with various PMO(705)-transport peptide (SEQ ID NO: 1-transport peptide) conjugates, as shown in Table 1 herein, at a concentration of 25 μM, where in each case the PMO is linked to the C (cysteine) residue.
Figure 16:
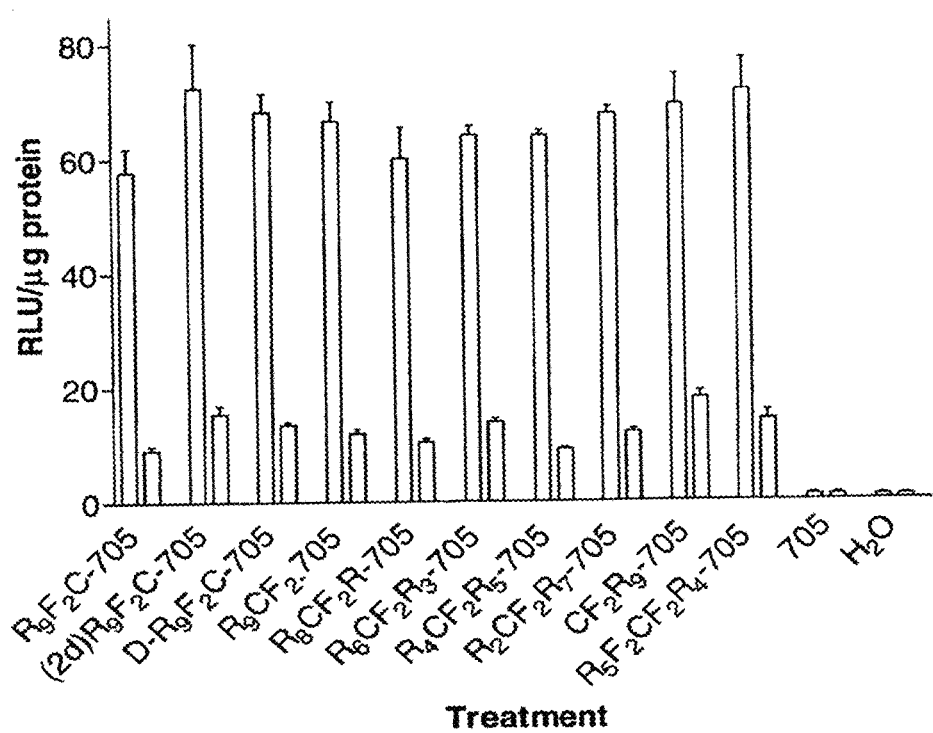
FIG. 16 shows luciferase production (RLU/μg protein), in HeLa pLuc705 cells treated with conjugates of antisense PMO (705) (SEQ ID NO: 1) with different-sequence transporter peptides, at a concentration of 1 μM (dark bars) or 5 μM (light bars) in serum-free medium for 6 hours, where in each case the PMO is linked to the C (cysteine) residue.

Further experiments were performed to evaluate the effect of the position of both the hydrophobic segment and the PMO attachment point within the transporter. FIGS. 15 and 16 show the results of the pLuc/705 assay carried out with conjugates of PMO 705 (SEQ ID NO.:1) linked to the transport peptides having SEQ ID NO: 13 and 16-26 as shown in Table 1. In each conjugate, the PMO is linked via a C-terminal or internal cysteine (C) residue. As shown by the data, transporters in which the Y subunits are internal (i.e. flanked by X subunits) generally performed as well or better than those in which the Y subunits are at a terminus. The linkage point could be adjacent the Y subunits or remote from the Y subunits.

Figure 17:
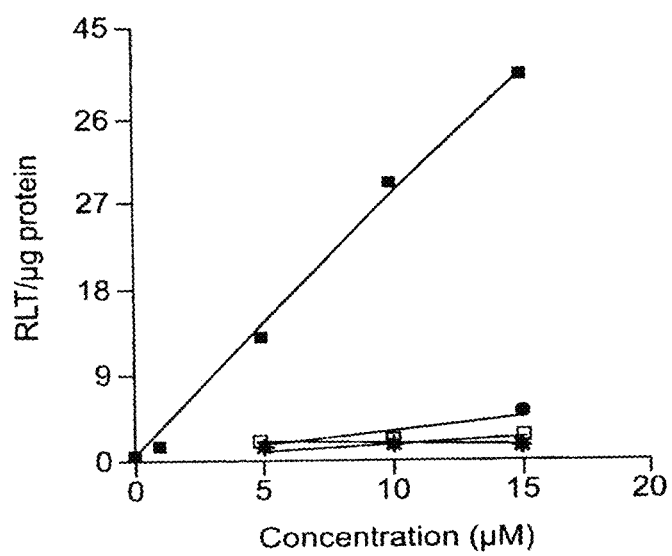
FIG. 17 shows luciferase production (RLU/μg protein) in HeLa pLuc705 cells treated with R9F2-C-PMO-705 (closed square) (SEQ ID NO.:43-SEQ ID NO: 1) and the following control PMOs containing either two or four mismatches, scrambled or irrelevant sequences: R9F2-C-$705_{2MM}$ (closed circle) (SEQ ID NO.:43-SEQ ID NO: 2), $R_9F_2$-C-$705_{4MM}$ ( ) (SEQ ID NO.:43-SEQ ID NO: 3), $R_9F_2$-C-$705_{SCR}$ (∇) (SEQ ID NO.:43-SEQ ID NO: 4) and $R_9F_2$-C-cmyc (*) (SEQ ID NO.:43-SEQ ID NO: 5).

To determine whether the presence of the transporter adversely affects the antisense specificity of the PMO, as has been observed for Tat transporters (Moulton, Hase et al. 2003), the assay was carried out with R$_9$F$_2$-C-PMO (SEQ ID NO: 43-PMO) conjugates of three mismatched-sequence control PMOs, designated 705$_{2MM}$ (two mismatches, SEQ ID NO.:2), 705$_{4MM}$ (four mismatches, SEQ ID NO.:3) and 705$_{SCR}$ (scrambled, SEQ ID NO.:4) (see Table 1 for sequences). Up to the highest concentration tested, the three control conjugates showed no antisense activity; that is, they did not restore luciferase activity by correcting the 705 splice defect (FIG. 17). Accordingly, there was no indication of adverse effects on specificity by the transporter.

Fluorescence microscopy and the splice-correction assay were also used to determine the time required for the conjugate to enter the cytoplasm and nuclei of cells. HeLa, NIH3T3 or HeLa pLuc/705 cells were treated with the R$_9$F$_2$-C-PMO (SEQ ID NO: 43-PMO) conjugate for 20 minutes and imaged. A nuclear stain, dihydroethidium (DHE, Molecular Probes, Eugene, Oreg.), was used to locate the nucleus. Diffuse green fluorescence was seen in both cytoplasm and nucleus, and overlapped with the intense red of DHE in the nucleus.

Figure 18:
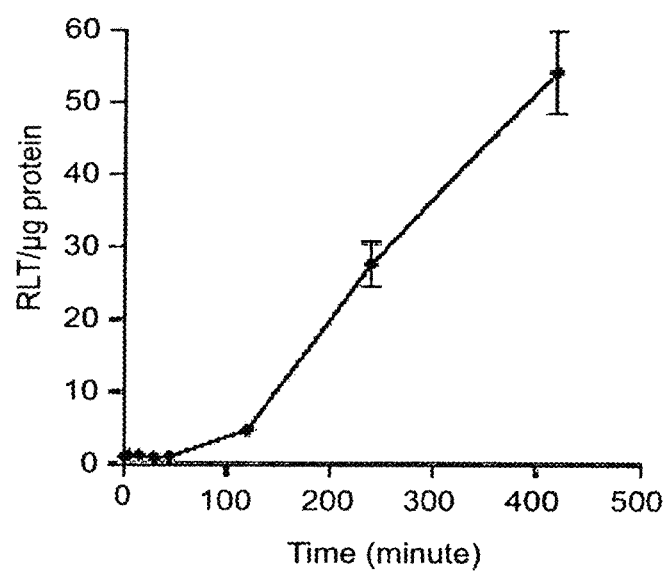
FIG. 18 shows luciferase production (RLU/μg protein) in HeLa pLuc705 cells treated with $R_9F_2C$—PMO-705 (SEQ ID NO.:43-SEQ ID NO: 1), measured at several times points.
Figure 19A:
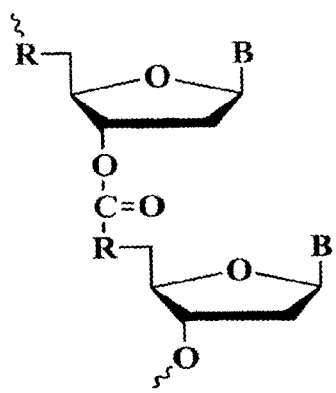
FIGS. 19A-G show examples of other uncharged antisense oligomer types which may be modified to contain the transport peptides as described herein.
Figure 19B:
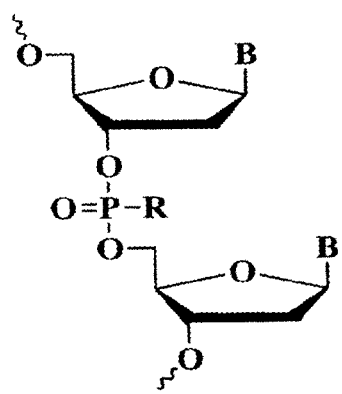
Figure 19C:
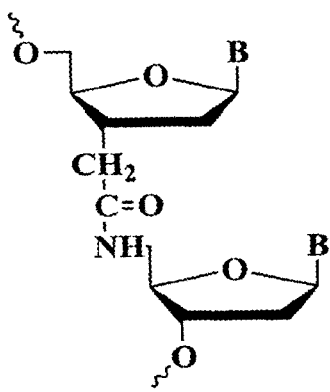
Figure 19D:
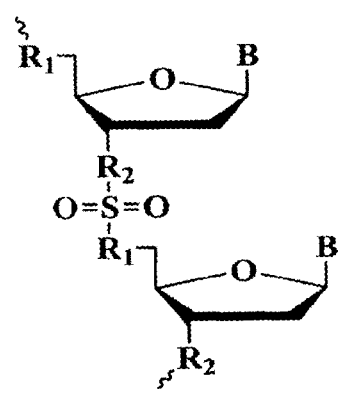
Figure 19E:
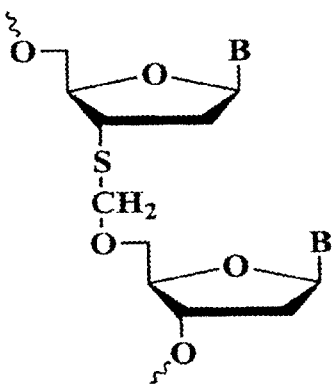
Figure 19F:
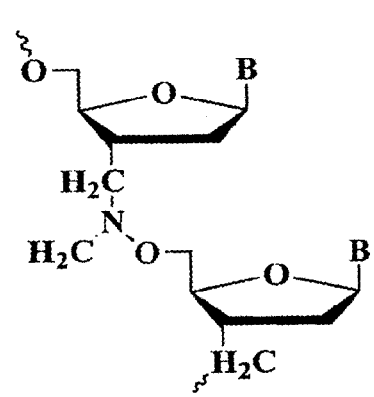
Figure 19G:
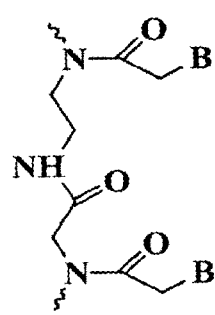

In the splice-correction assay, the production of functional luciferase was monitored over time, showing that luciferase was produced after as little as 120 minutes of incubation time with the R$_9$F$_2$C-705 PMO (SEQ ID NO: 43-PMO) (FIG. 18).

C. Antisense Activity in Cell-Free Systems

To investigate antisense activity of the conjugates in a manner independent of cellular transport, peptide-conjugated and unconjugated PMOs were tested in a cell-free translation system for their ability to sterically block translation of a downstream reporter gene. The effects of various antisense PMOs on translation of in vitro transcribed RNA from plasmids containing various viral nucleotide sequences fused directly upstream of the coding region for firefly luciferase (FLUC) were measured by in vitro translation reactions in a commercially available rabbit reticulocyte lysate (RRL) system, as described in Example 9. Specifically, three different regions of the Dengue type 2 virus were fused to the FLUC gene and a region surrounding the AUG start codon of the human c-myc gene. Also targeted was a sequence of murine hepatitis virus (MHV) that surrounds the start codon of the 1ab gene (Neuman, B. W. et al., J. Virol. 2004, in press).

Figure 21:
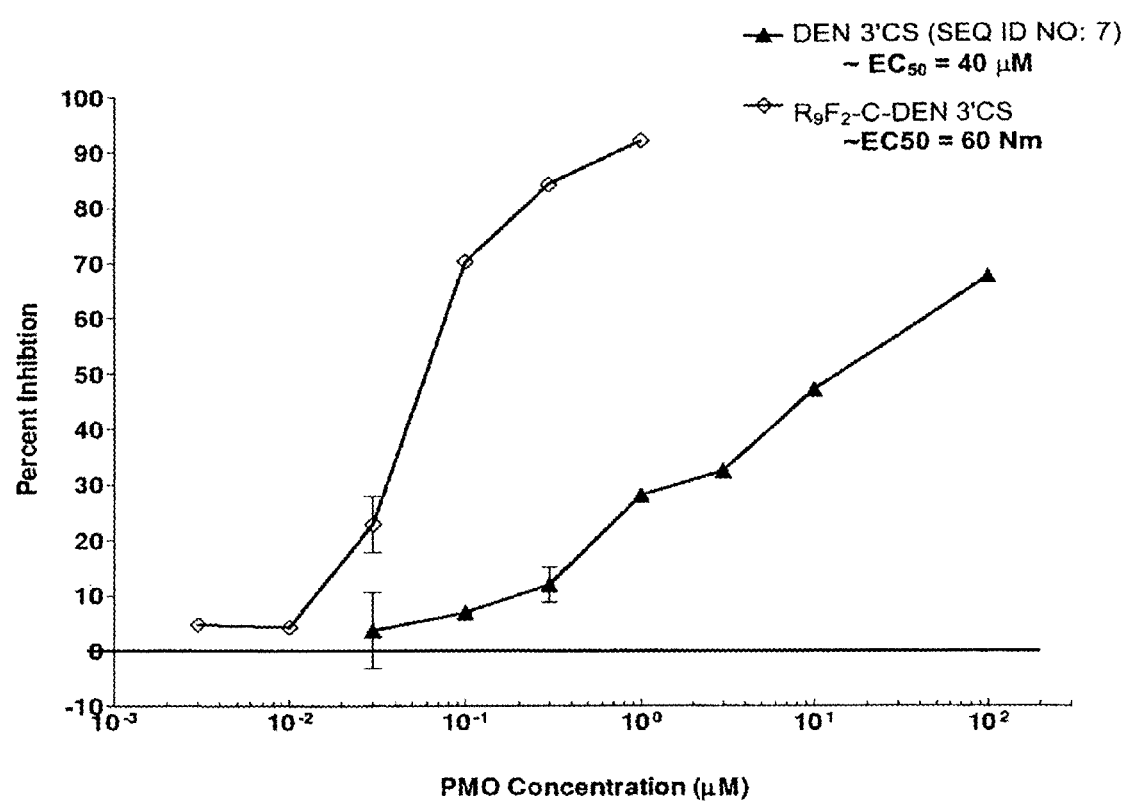
FIGS. 21-23 represent the results of inhibition of cell-free translation by peptide PMO conjugates directed to viral sequences placed immediately upstream of the firefly luciferase reporter gene.
Figure 22:
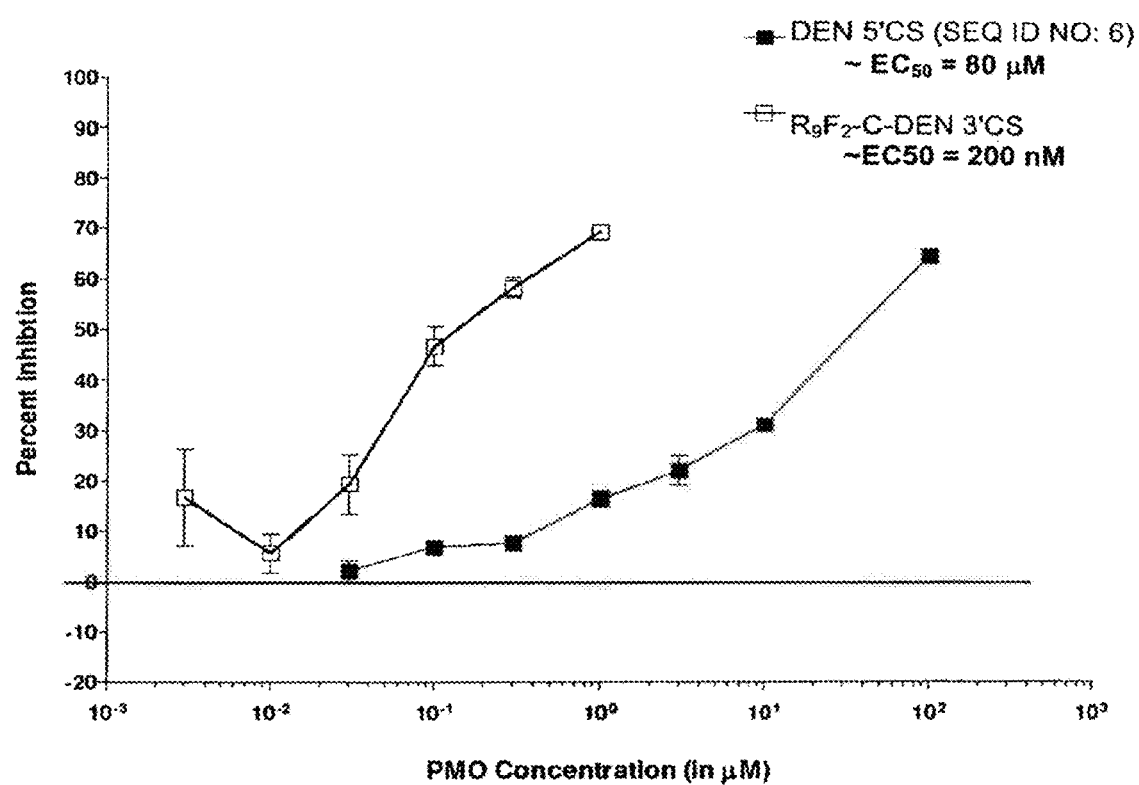
Figure 23:
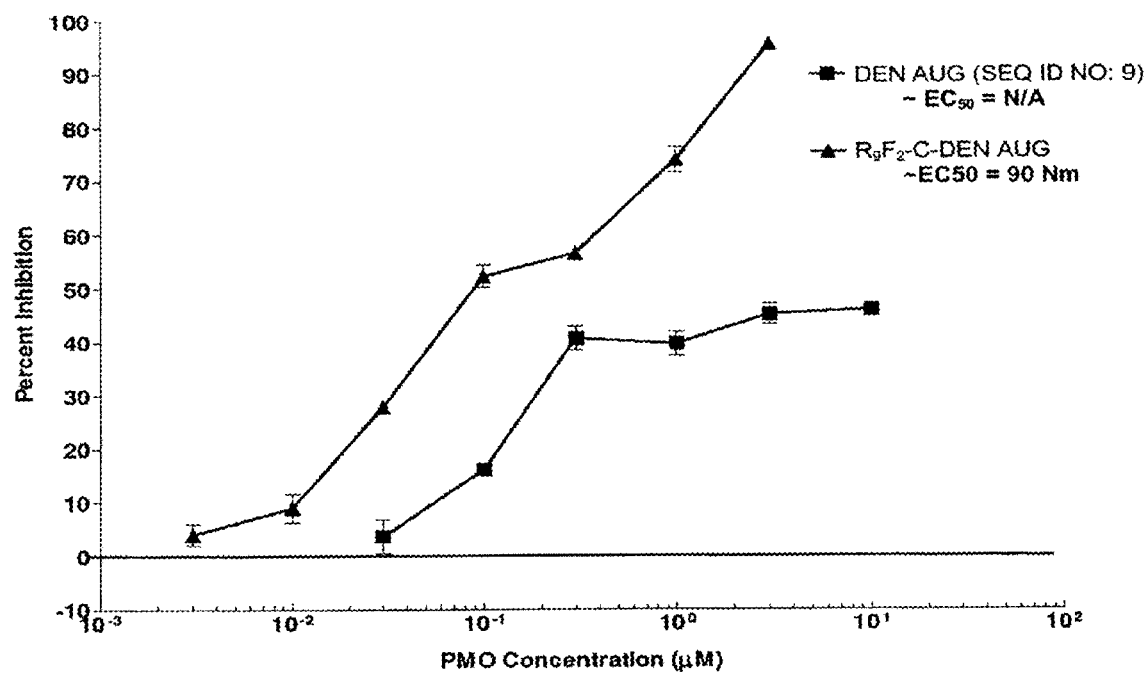
Figure 28:
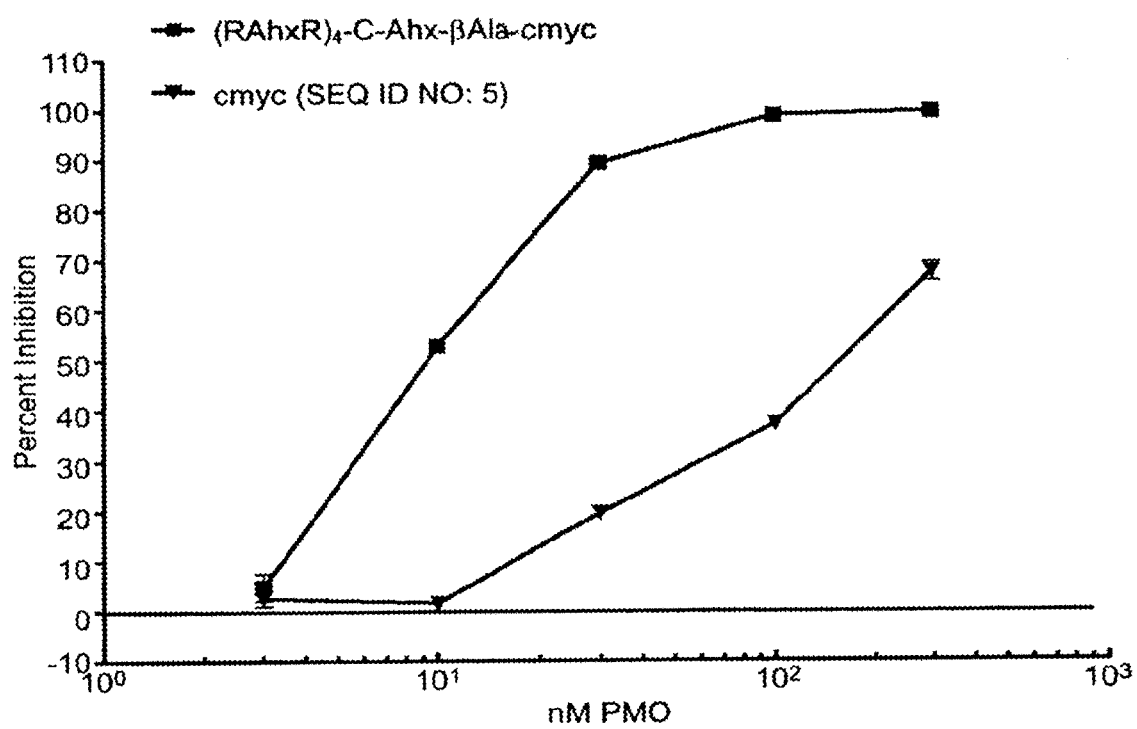
FIG. 28 shows the results of inhibition of cell-free translation by peptide-PMO conjugates targeted to a region of the human c-myc gene that surrounds the translational start codon fused to the firefly luciferase reporter gene.

As shown in FIGS. 21-23 and 28, conjugation of the antisense oligomers to peptide transporters of the invention was found to increase effectiveness of the antisense PMOs by between 10-500 fold, as reflected by the concentration required to achieve 50% inhibition of target expression (EC$_{50}$). Conjugation to R$_9$F$_2$ (SEQ ID NO: 13) enhanced the antisense effectiveness of the PMO compared to unconjugated PMO by as much as 500 fold (FIGS. 21-23). As shown in FIG. 28, similar results were obtained using the (RAhxR)$_4$ peptide (SEQ ID NO:34) conjugated to an anti-c-myc PMO (SEQ ID NO:5).

Although the scope of the invention is not limited by mechanism, the enhanced antisense activity observed with the peptide conjugates of the invention in cell free translation systems may be due to a localized disruption of RNA secondary structure by the peptide. One construct used in the RRL assays, pDCLD, contains the 5' most 204 bases of the Dengue virus genome, which encodes the initial 35 amino acids of the polyprotein, placed in frame with the FLUC gene. The computer-predicted RNA structure for this region, shown in FIG. 29, which was generated using the 'mfold' RNA folding program (Zuker 2003), indicates extensive secondary structure. The secondary structure shown in FIG.

29 also agrees with that predicted by Khromykh et al. for the same region of a distinct but related flavivirus, Kunjin virus (Khromykh, Kondratieva et al., 2003).

The ability of unconjugated antisense PMOs to hybridize and block translation can be inhibited by certain secondary structures, as appears to be the case for this segment of RNA, as shown in FIG. 23. In this example, unconjugated PMO was unable to produce a 50% reduction in translation despite increasing concentration. However, $R_9F_2$ (SEQ ID NO.: 13) peptide conjugated PMO has greatly enhanced antisense activity, producing nearly 100% suppression of the reporter gene translation at the same concentration (FIG. 23).

D. Biodistribution In Vivo

Tissue culture experiments from a variety of experimental systems clearly demonstrate that the transport peptides of the invention enhance delivery to intracellular compartments, including the cytoplasm and nucleus. To extend these observations to an in vivo system, a comparative analysis of PMO and peptide conjugated PMO uptake in spleen and lymph node cells was performed in mice. As described in Example 10 and shown in FIG. 27, the $R_5F_2R_4$ transport peptide (SEQ ID NO:20) greatly enhanced delivery to spleen and lymph node cells in total, and to specific sub-populations of cells from these tissues, including CD4 and CD8 positive lymphocytes, monocytes, macrophages and B cells. Furthermore, as described in Example 10, peptide conjugated PMO were shown to have significant residence time in spleen and lymph node-derived cells four days after a multidose PMO treatment regimen in mice had ended.

III. Applications

The transporters and conjugates of the invention are particularly useful for targeting a substantially uncharged antisense oligomer, such as a PMO, to a cell nucleus, by exposing the cell to a conjugate comprising the oligomer covalently linked to a transport peptide as described above. The transporters are effective to deliver the antisense oligomer across both the cell and nuclear membranes, and to enhance the antisense activity of the oligomer, as demonstrated above.

Nuclear delivery allows targeting of splice sites, which can be implemented for generating dominant/negative proteins, which preserve, for example, the feedback function of a protein, but not its enzymatic activity. This is accomplished by selectively inhibiting splice donor or acceptor sites in pre-mRNA that eliminate from the mature spliced mRNA one or more exons encoding unwanted functions. Useful gene targets for this approach include, but are not limited to, CD86, c-FLIP, CTLA-4, TGF-b and c-myc.

The translation start site (i.e. the AUG start codon) is another useful target for antisense therapy, as are cis-acting elements required for viral replication or transcription. The inhibition of viral replication can be accomplished either by blocking translation of essential viral proteins or by targeting regions of the viral genome required for either nucleic acid replication or mRNA transcription. These cis-acting elements are often located in untranslated regions (UTRs) of the viral genome and typically found at either or both the 5' and 3' termini of the genome. Examples of these elements include internal ribosome entry sites (IRES) as found in hepatitis C virus (HCV), transcriptional regulatory sequences (TRS) as found in the human coronavirus that causes systemic acquired respiratory syndrome (SARS), cyclization sequences (CS) as found in flaviviruses, and the tRNA primer binding site (PBS) found in retroviruses such as human immunodeficiency virus (HIV). Often, these elements have extensive secondary structural characteristics and are recalcitrant to binding of antisense oligomers. Conjugation of peptides as disclosed herein to substantially uncharged antisense oligomers is believed to allow disruption of such secondary structures and thus enhanced binding of the oligomers to their targets. Therefore, the methods and compositions of the invention described herein provide the ability to more effectively target these regions of viral genomes and inhibit viral replication.

PMO conjugates find use, in general, in any indication in which delivery of an oligonucleotide to a cell is desired, including antisense applications. Such indications include, but are not limited to, proliferative disorders or ischemia, by targeting p53; polycystic kidney disease, restenosis, and cancer, by targeting c-myc; pulmonary inflammation or septic shock, by targeting TNF-α; alteration of drug metabolism, by targeting P450 enzymes; prostate cancer, by targeting β-HCG or androgen receptor; glioblastoma, by targeting integrin αV. Treatment of stem cells with antisense oligonucleotides targeted to genes preferentially expressed in such cells can also be used for cancer treatment (e.g. co-owned and copending U.S. application Ser. No. 09/679, 475; PCT Pubn. No. WO 01/25405). Treatment of infectious diseases using antisense oligonucleotides targeted to either viral genes or cis-acting sequences involved in replication or transcription can be used as antiviral therapeutic treatments (e.g. co-owned US applications: Ser. No. 10/272,865, pubn. no. US 2002/0171335, issued as U.S. Pat. No. 6,828,105; copending application Ser. No. 10/422,671, pubn. no. US 2003/0224353; 60/493,990; 60/493,043; 60/514,064; and 60/532,701, expired). Treatment of certain immunologic conditions can be facilitated using antisense oligonucleotides conjugated to peptides that can provide intracellular delivery specifically to naïve or activated lymphocytes (e.g. co-owned U.S. application 60/505,418, expired).

The conjugates are particularly useful in treatment of vascular proliferative disorders such as restenosis. Areas of vessel injury include, for example, restenosis or renarrowing of the vascular lumen following vascular intervention, such as coronary artery balloon angioplasty, with or without stent insertion. Restenosis is believed to occur in about 30% to 60% of lesions treated by angioplasty and about 20% of lesions treated with stents within 3 to 6 months following the procedure. (See, e.g., Dev, N. B. et al., *Cathet Cardiovasc Diagn* 45(3):337-45, 1998). Stenosis can also occur after a coronary artery bypass operation, wherein heart surgery is done to reroute, or "bypass," blood around clogged arteries and improve the supply of blood and oxygen to the heart. In such cases, the stenosis may occur in the transplanted blood vessel segments, and particularly at the junction of replaced vessels. Stenosis can also occur at anastomotic junctions created for dialysis.

In this aspect, a PMO conjugate, preferably targeting c-myc, is employed in a coated stent, in a soaking solution for treatment of saphenous veins, or otherwise delivered to the site of vascular injury. Microbubble compositions, such as described below, have been found particularly useful in delivery of attached molecules, such as oligonucleotides, to areas of thrombosis or vessel injury, e.g. damaged endothelium (see e.g. Kipshidze et al., 2001, 2002; Kim et al., 2001; PCT Pubn. No. WO 2000/02588) as well as to selected organs such as the liver and kidney. A preferred antirestenotic composition is an anti-c-myc PMO (e.g. SEQ ID NO:5) conjugated to an (RAhxR)$_4$ (SEQ ID NO:34) transport peptide through an Ahx-βAla linker (as shown in FIG. 4D).

IV. Compositions Containing PMO-Transporter Conjugates and Microbubble Carrier Suspensions Aqueous suspensions of insoluble gas-containing microbubbles have been shown to be effective vehicles for delivery of oligonucleotides, including PMOs, as described, for example, in co-owned U.S. Pat. Nos. 5,849,727 and 6,117,858 and pending U.S. application Ser. No. 10/668,988. In general, the composition comprises a liquid suspension, preferably an aqueous suspension, of microbubbles containing a blood-insoluble gas. The microbubbles are preferably about 0.1 to 10μ in diameter. Generally, any blood-insoluble gas which is nontoxic and gaseous at body temperature can be used. The insoluble gas should have a diffusion coefficient and blood solubility lower than nitrogen or oxygen, which diffuse in the internal atmosphere of the blood vessel. Examples of useful gases are the noble gases, e.g. helium or argon, as well as fluorocarbon gases and sulfur hexafluoride. Generally, perfluorocarbon gases, such as perfluoromethane, perfluoroethane, perfluoropropane, perfluorobutane, and perfluoropentane, are preferred.

The gaseous microbubbles are stabilized by a fluid filmogenic coating, to prevent coalescence and to provide an interface for binding of molecules to the microbubbles. The fluid is preferably an aqueous solution or suspension of one or more components selected from proteins, surfactants, lipids, including phospholipids, and polysaccharides. In preferred embodiments, the components are selected from proteins, surfactant compounds, and polysaccharides. Suitable proteins include, for example, albumin, gamma globulin, apotransferrin, hemoglobin, collagen, and urease. Human proteins, e.g. human serum albumin (HSA), are preferred.

Conventional surfactants include compounds such as alkyl polyether alcohols, alkylphenol polyether alcohols, and alcohol ethoxylates, having higher alkyl (e.g. 6-20 carbon atom) groups, fatty acid alkanolamides or alkylene oxide adducts thereof, and fatty acid glycerol monoesters. Surfactants particularly intended for use in microbubble contrast agent compositions are disclosed, for example, in Nycomed Imaging patents U.S. Pat. No. 6,274,120 (fatty acids, polyhydroxyalkyl esters such as esters of pentaerythritol, ethylene glycol or glycerol, fatty alcohols and amines, and esters or amides thereof, lipophilic aldehydes and ketones; lipophilic derivatives of sugars, etc.), U.S. Pat. No. 5,990,263 (methoxy-terminated PEG acylated with e.g. 6-hexadecanoyloxyhexadecanoyl), and U.S. Pat. No. 5,919,434.

Other filmogenic synthetic polymers may also be used; see, for example, U.S. Pat. No. 6,068,857 (Weitschies) and U.S. Pat. No. 6,143,276 (Unger), which describe microbubbles having a biodegradable polymer shell, where the polymer is selected from e.g. polylactic acid, an acrylate polymer, polyacrylamide, polycyanoacrylate, a polyester, polyether, polyamide, polysiloxane, polycarbonate, or polyphosphazene, and various combinations of copolymers thereof, such as a lactic acid-glycolic acid copolymer.

Such compositions have been used as contrast agents for diagnostic ultrasound, and have also been described for therapeutic applications, such as enhancement of drug penetration (Tachibana et al., U.S. Pat. No. 5,315,998), as thrombolytics (Porter, U.S. Pat. No. 5,648,098), and for drug delivery (Unger, U.S. Pat. No. 6,143,276; Klaveness et al., U.S. Pat. No. 6,261,537; Porter et al., U.S. Pat. No. 6,117,858).

In one embodiment, the carrier is a suspension of perfluorocarbon-containing dextrose/albumin microbubbles known as PESDA (perfluorocarbon-exposed sonicated dextrose/albumin). Human serum albumin (HSA) is easily metabolized within the body and has been widely used as a contrast agent. The composition may be prepared as described in co-owned U.S. Pat. Nos. 5,849,727 and 6,117,858. Briefly, a dextrose/albumin solution is sonicated while being perfused with the perfluorocarbon gas. The microbubbles are preferably formed in an $N_2$-depleted, preferably $N_2$-free, environment, typically by introducing an $N_2$-depleted (in comparison to room air) or $N_2$.free gas into the interface between the sonicating horn and the solution. Microbubbles formed in this way are found to be significantly smaller and stabler than those formed in the presence of room air. (See e.g. Porter et al., U.S. Pat. No. 6,245,747.)

The microbubbles are conjugated with a compound to be delivered, such as a PMO-transporter conjugate, simply by incubating the microbubble suspension, with agitation if necessary, with a liquid formulation of the compound. The incubation may be carried out at room temperature, or at moderately higher temperatures, as long as the stability of the drug or the microbubbles is not compromised. It is believed that compounds incubated with such suspensions non-covalently bind at the gas-fluid interface of the microbubbles, and that, upon administration, the cell membrane fluidizing feature of the insoluble (e.g. perfluorocarbon) gas enhances cell entry for the compound.

V. Modified Antisense Oligonucleotides

In another aspect, the invention provides antisense oligomers which are themselves modified with charged moieties of the structure $R^1N$=$C(NH_2)R^2$, where $R^1$ is H or R, and $R^2$ is R, $NH_2$, NHR, or $NR_2$, where R is lower alkyl or lower alkenyl and may further include oxygen or nitrogen; $R^1$ and $R^2$ may together form a ring; and the side chain moiety is linked to the amino acid subunit via $R^1$ or $R^2$. Specifically, the oligomer comprises a sequence of subunits connected by intersubunit linkages, where the sequence of subunits supports a sequence of bases effective to hybridize to a complementary-sequence target polynucleotide, to form a target/antisense duplex; and, carried on at least six contiguous intersubunit linkages, a charged moiety as described above. In a preferred embodiment, the charged moieties are independently selected from the group consisting of guanidyl (—HN=$C(NH_2)$NH—), amidinyl (—C(=NH)($NH_2$)), 2-amino hexahydropyrimidyl (=HN—CH($NH_2$)NH—), 2-aminopyridinyl (—C(=N)($NH_2$)), and 2-aminopyrimidonyl (—HN—$C(NH_2)$=N—) (see FIG. 3).

Preferably, the oligomer is an uncharged oligomer. Examples of uncharged antisense oligomers are shown in FIGS. 19A-G. A small number of charged linkages, e.g. phosphorothioate or, more preferably, charged phosphoramidate, may also be incorporated into the oligomers, preferably fewer than one charged linkage per four uncharged linkages. The uncharged linkages shown in FIG. 19 include carbonate (19A, R=O) and carbamate (19A, R=$NH_2$) linkages; alkyl phosphonate and phosphotriester linkages (19B, R=alkyl or O-alkyl); amide linkages (19C); sulfones (19D, $R_1$, $R_2$=$CH_2$); sulfonamides (19D, $R_1$=NH, $R_2$=$CH_2$, or vice versa); sulfamates (19D, $R_1$, $R_2$=NH); thioformacetyl (19E) and 3'-methylene-N-methylhydroxyamino (19F). Preferred uncharged antisense oligomer types include alkyl phosphonate-, phosphotriester-, and phosphoramidate- or phosphorodiamidate-linked oligonucleotides. In FIGS. 19A-G, B represents a purine or pyrimidine base-pairing moiety effective to bind, by base-specific hydrogen bonding, to a base in a polynucleotide, preferably selected from adenine, cytosine, guanine, thymine and uracil. Although FIGS. 19A-F depict deoxyribose rings, subunits may also comprise, for example, substituted ribose rings or morpholino rings, as described above.

In a preferred embodiment, the oligomer comprises morpholino subunits, e.g. as shown in FIG. 1, linked by phosphorodiamidate linkages, as shown in FIG. 2B. In this case, the charged moiety is preferably attached at the phosphorus atom of the linkage, via the side group X, which is typically amino.

Figure 20:
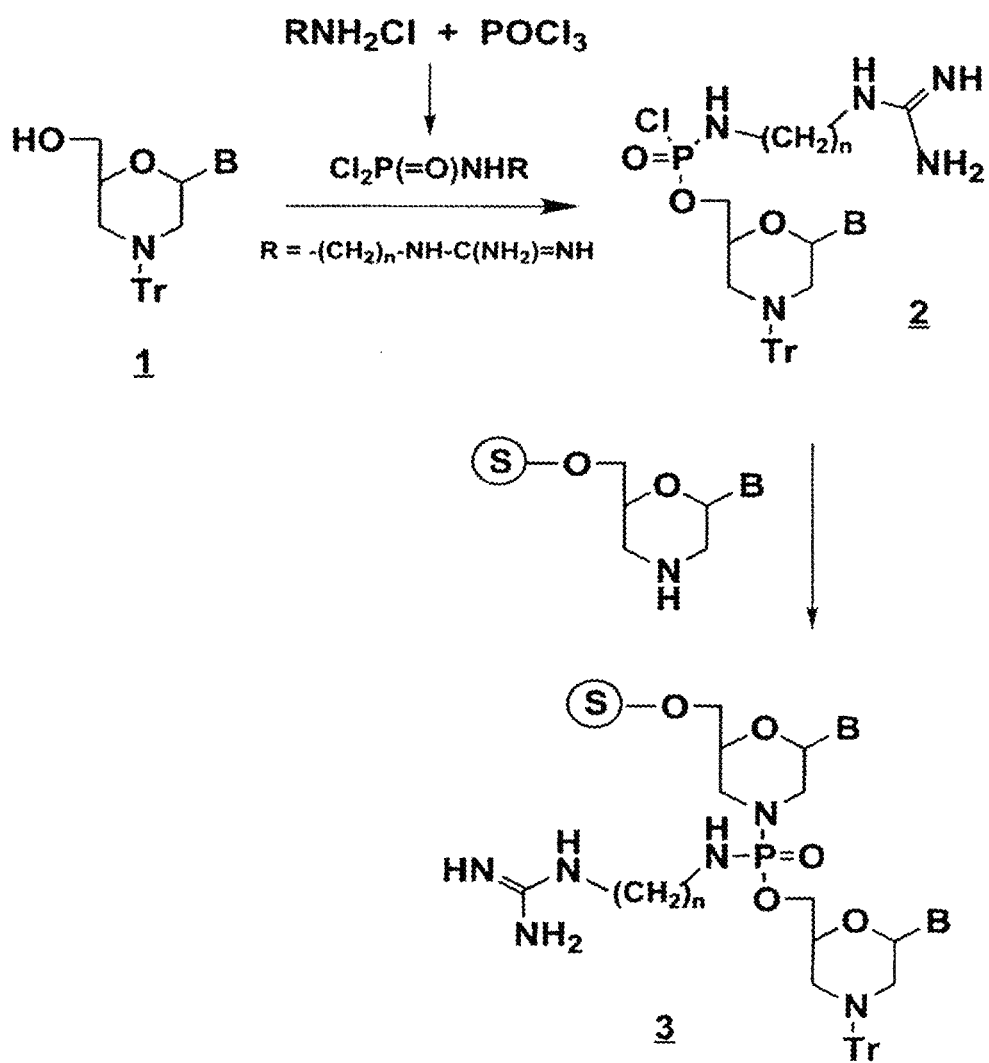
FIG. 20 shows a method of preparing a PMO having a modified intersubunit side chain containing cationic charge moieties.

For example, FIG. 20 shows the preparation of a phosphorodiamidate-linked morpholino oligomer having a modified amino side chain. PMOs are conveniently synthesized via 5'-activated morpholino subunits having a protected morpholino nitrogen, as shown, for example, in U.S. Pat. No. 5,185,444. Such subunits having dialkylamino side chains can be stored at low temperature for months prior to use (see e.g. Summerton and Weller, *Antisense & Nucleic Acid Drug Dev.* 7:187-195, 1997). As described, for example, in U.S. Pat. No. 5,378,841, which is incorporated herein by reference, such a subunit having a dimethyl amino side chain was prepared by reaction of the N-protected 5'-hydroxy morpholino subunit with dimethylamino dichlorophosphate ($POCl_2N(CH_3)_2$). Such N-substituted phosphoramidic dichlorides ($POCl_2NRR'$) can be prepared by reaction of the desired amine; i.e. dimethylamine HCl in this case, with phosphorous oxychloride.

EXAMPLES

The following examples are intended to illustrate but not to limit the invention.
Materials and Methods
Peptide and Morpholino Synthesis All peptides were custom synthesized by Global Peptide Services (Ft. Collins, Colo.) or at AVI BioPharma (Corvallis, Oreg.) and purified to >90% purity (see Example 2 below). PMOs were synthesized at AVI BioPharma in accordance with known methods, as described, for example, in Summerton and Weller, 1993, 1997, and U.S. Pat. No. 5,185,444.
Cell Culture HeLa pLuc/705 (Kang, Cho et al. 1998) is the HeLa S3 cell line stably transfected with a plasmid carrying the luciferase coding sequence interrupted by a mutated human β-globin intron 2 (Gene Tools, Philomath, Oreg.). Other cell lines were obtained from ATCC (Manassas, Va.). All cell lines were cultured in RPMI 1640 supplemented with 2 mM glutamine, 100 µg/ml streptomycin, 100 U/ml penicillin (DME/F12) and 10% of fetal bovine serum (FBS) (Hyclone, Ogden, Utah). All assays were carried out with exponentially growing cells in culture media containing 10% fetal bovine serum (FBS) unless otherwise specified.
Fluorescence Microscopy Cells were plated onto a 48-well plate. The next day the conditioned medium was removed and the test substances in fresh medium were added to the wells. After incubation, the cells were washed with phosphate-buffered saline (PBS) three times and visualized directly in the culture medium with a Nikon Diaphot 300 inverted microscope. Images were captured with an Olympus digital camera connected to a computer using MagnaFire software (Optronics, Goleta, Calif.).
Fluorometry HeLa pLuc/705 cells plated in a 48 well plate were treated with medium containing test substance. After incubation, cells were washed with PBS three times.

To measure the sum of membrane-bound and internalized fluorescence, cells were lysed directly in the wells by addition of 100 µl of cell lysis buffer (Promega, Madison, Wis.) to each well. Cell lysates were collected. The total fluorescence was determined by mixing 20 µl of cell lysate and 80 µl of 0.1 M $Na_2CO_3$ (pH 11) and measuring with an Flx 800 microplate fluorescence-luminescence reader with excitation at 485 nm and emission at 524 nm.

To measure internalized conjugate, the membrane-bound conjugate was removed by trypsinization, as follows. Trypsin (100 µl, 10%, Hyclone, Logan, Utah) was added to each well and incubated for 6 minutes at 37° C., followed by addition of 300 µl of culture media. The cells were spun down and washed with PBS, then lysed with 100 µl cell lysis buffer. The fluorescence of the cell lysate was measured as described above.
Flow Cytometry To analyze the internalization of fluorescein-labeled peptide-PMO conjugates by flow cytometry, HeLa pLuc/705 cells in a 48-well plate were treated with medium containing test substance. After incubation, cells were washed with PBS three times, and 100 µl of trypsin (see above) was added to each well, followed by incubation for 6 minutes at 37° C., then by addition of 300 µl of culture media. The cells were spun down and washed once with PBS, then suspended in 500 µl of a buffer containing PBS with 1% FBS and 0.2% $NaN_3$. The flow data was collected using a BD FACSCalibur™ cytometer, and data was analyzed using FCS Express 2 (De Novo Software, Thornhill, Ontario, Canada).
Cell-Free Translation Assays Plasmids. The coding sequence for firefly luciferase (FLUC) was subcloned into the multiple cloning site of plasmid pCi-Neo (Promega) at the Sal I and Not I sites and the resulting plasmid named pCNlucr. Subsequently, two different nucleotide regions of the Dengue type 2 virus (DEN2, Genbank accession number AY037116) were subcloned into the Nhe I and Sal I sites of pCNlucr. This placed the DEN2 sequences immediately upstream of the start codon of the FLUC gene. Two different plasmids were constructed: pCNDEN3'Cslucr, containing DEN2 nucleotides 10606 to 10646, and pCNDEN5'Cslucr, containing DEN2 nucleotides 119 to 161. PMOs targeting these regions (DEN3'CS and DEN5'CS) are listed in Table 1 as SEQ ID NOS: 7 and 6, respectively.

A similar construct using a portion of the murine hepatitis virus (MHV) genome was constructed in the same vector (pCNlucr) by inserting nucleotides 188 to 230 of MHV (Genbank accession number AF029248) into the NheI and SalI sites of pCNlucr. This fragment of MHV contains nucleotides −22 to +21 relative to the "A" of the AUG of the MHV Orf 1a gene and generates a fusion protein with the luciferase reporter gene. The PMO that targets this region is SEQ ID NO: 9.

A fourth plasmid construct (pDCLD) was made using a pUC-derived vector that placed a larger portion of the DEN2 sequence (GenBank accession number U87411, nucleotides 1 to 204), containing the 5' end of the DEN2 polyprotein coding sequence, immediately upstream and in frame with the fLUC gene. A PMO that targets this region (DEN AUG) is listed as SEQ ID NO: 8 in Table 1. The DEN AUG PMO targets the DEN2 polyprotein start codon and its target is highlighted in FIG. 29 (nucleotides 87-106).

A fifth plasmid construct was created with a 30 base pair region surrounding the ATG start codon of human c-myc gene (5'-AGCCTCCCGCGACGATGCCCCTCAACGTTA-3', (SEQ ID NO: 48), Genbank accession number V00568) subcloned into the Nhe I and Sal I sites of pCNlucr and named pCNmycluc. This placed the c-myc coding sequences in frame with the amino acid coding sequences of the fLUC gene (c-myc:fLUC). A PMO targeting this region of c-myc, designated AVI-4126, is listed as SEQ ID NO: 5.

Transcription and translation. All of the above-described plasmids include the T7 RNA polymerase promoter upstream of the viral:fLUC sequences and allow RNA to be produced from these plasmids, after linearization with either NotI or SnaBI, using the T7 polymerase-based Megascript kit and protocol (Ambion).

In vitro translations were carried out using transcribed RNA, at a final concentration in each reaction of 1 nM, with 12 µl nuclease-treated rabbit reticulocyte lysate (Promega) in addition to PMO, $R_9F_2$-PMO (SEQ ID NO: 13-PMO), or water. Translation reaction mixture (10 µl) was then mixed with 50 µl luciferase assay reagent (Promega) according to manufacturer's instructions, and light emission was read on a FLx800 microplate luminometer (BIO-TEC Instruments). Reactions were assayed for relative light units with the KC Junior program (BIO-TEC) using the luminescence function and a sensitivity setting of 125. In the experiments described herein, twelve reactions were assayed at one time, including water-control reactions in the first and last well of each row. The relative light units (RLU) produced by each reaction was normalized to the mean of all control reactions and expressed either as percent inhibition of luciferase expression or relative light units as a function of PMO concentration, as described in Example 8.

Protease Digestion of Peptide-PMO Conjugates

Experiments to measure the resistance of peptide-PMO conjugates to protease digestion were performed as follows. Proteinase K (10 units) was placed in 0.1 ml of 50 mM Tris-HCl (pH 7.2), 5 mM $CaCl_2$ buffer and 40 µg of peptide-PMO ($R_9F_2C$-705) conjugate (SEQ ID NO: 43-SEQ ID NO:1) was added. After either 5 minutes or 2 hours at 37 degrees C., samples were frozen on dry ice until analysis by MALDI TOF mass spectroscopy.

Example 1

3'-Fluoresceination of a PMO

A protected and activated carboxyfluorescein, e.g. 6-carboxyfluorescein dipivalate N-hydroxysuccinimide ester, commercially available from Berry & Associates, Inc. (Dexter, Mich.), was dissolved in NMP (0.05M), and the solution was added to a PMO synthesis column (see "Morpholino synthesis", above) in sufficient volume to cover the resin. The mixture was incubated at 45° C. for 20 minutes, then the column was drained and a second similar portion of protected and activated carboxyfluorescein was added to the column and incubated at 45° C. for 60 minutes. The column was drained and washed with NMP, and the oligomer was cleaved from the resin using 1 ml of cleavage solution (0.1M dithiothreitol in NMP containing 10% triethylamine). The resin was washed with 300 µl of cleavage solution three times, immediately followed by addition of 4 ml of concentrated ammonia hydroxide and 16 hours incubation at 45° C. to remove base protecting groups. The morpholino oligomer was precipitated by adding 8 volumes of acetone, the mixture was centrifuged, and the pellet was washed with 15 ml of $CH_3CN$. The washed pellet was re-dissolved in 4 ml of $H_2O$ and lyophilized. The product was analyzed by time-of-flight MALDI mass spectrometry (MALDI-TOF) and high pressure liquid chromatography (HPLC).

Example 2

Peptide Synthesis and Attachment of Transport Peptide

Peptides were synthesized by Fmoc Solid Phase Peptide Synthesis, referred to herein as SPPS. A p-benzyloxybenzyl alcohol resin was used for synthesis of peptides with a C-terminal acid, while a Rink Amide MBHA resin was used for peptide amides. Both resins are available from Novabiochem (San Diego, Calif.). A typical synthesis cycle began with N-terminal deprotection via 20% piperidine. Then, N-α-Fmoc-protected amino acids were coupled to the growing peptide chain by activation with 2-(1H-benzotriazole-1-yl)-1,1,3,3-tetramethyluronium hexafluorophosphate (HBTU) in the presence of N,N-diisopropyl ethylamine (DIEA). Arginine side chains were protected with the 2,2, 4,6,7-pentamethyldihydrobenzofuran-5-sulfonyl (Pbf) protecting group, cysteine with trityl, and lysine side chains with t-butoxycarbonyl (Boc). The cycle was repeated until all of the amino acids were added, in a carboxy-to-amino direction, in the desired sequence. Cleavage from the synthesis resin and side chain deprotection were carried out simultaneously by treating the peptidyl-resin with a solution of 2.5% $H_2O$, 2.5% triisopropyl silane (TIS), and 95% trifluoroacetic acid (TFA). For peptides containing a cysteine residue, 2.5% 1,2-ethanedithiol (EDT) was added to the cleavage cocktail. Crude peptides were isolated by precipitation using a tenfold excess of diethyl ether.

Strong cation exchange HPLC utilizing Source 15S resin (Amersham Biosciences, Piscataway, N.J.) was used for purification, followed by a reversed phase desalt employing Amberchrom 300M resin (Tosoh Bioscience, Montgomeryville, Pa.). Desalted peptides were lyophilized and analyzed for identity and purity by MALDI-TOF MS, strong cation exchange (SCX) HPLC, and capillary electrophoresis (CE).

Peptides containing various C-terminal hydrophobic linkages were prepared as follows. Peptides were prepared for direct condensation with an amine or hydroxy group of the PMO by including combinations of natural and/or non-natural amino acids at the C-terminal end of the peptide during SPPS. Specifically, the linkages were comprised of the amino acids glycine, beta-alanine, and/or 6-aminohexanoic acid, used in different combinations of one or two residues. Peptide synthesis was otherwise identical to the synthesis of other peptide acids.

Peptide sequences that contain amine side chains, such as rTat and pTat (Table 1), were prepared using the 1-(4,4-dimethyl-2,6-dioxocyclohex-1-ylidene)ethyl (Dde) amine side chain protecting group. Lysine Dde groups survived the resin cleavage and deprotection of other amino acid side chain protecting groups. The side chain amines remain masked by Dde through conjugation with the PMO and are subsequently deprotected by treatment with 2% hydrazine in DMF.

The 5' attachment of a transport peptide via an amide bond was performed as follows. A C-terminally reactive peptide-benzotriazolyl ester was prepared by dissolving the peptide-acid (15 µmol), HBTU (14.25 µmol), and HOBt (15 µmol) in 200 µl NMP and adding DIEA (22.5 µmol). Immediately after addition of DIEA, the peptide solution was added to 1 ml of a 12 mM solution of 5'-piperazine-functionalized, 3'-acetyl-PMO in DMSO. After 180 minutes at 30° C., the reaction was diluted with a four-fold excess of water. The crude conjugate was purified first through a CM-Sepharose weak cation exchange column (Sigma, St. Louis, Mo.), to remove unconjugated PMO, and then through a reversed phase column (HLB column, Waters, Milford, Mass.). The conjugate was lyophilized and analyzed by MALDI-TOF MS, SCX HPLC, and CE.

Example 3

3'-Acetylation of PMO and 5' Attachment of Transport Peptide

Acetic anhydride (0.1 M), dissolved in N-methyl-2-pyrrolidinone (NMP) containing 1% N-ethyl morpholine (v/v), was added to a PMO synthesis product while the oligomer was still attached to the synthesis resin. After 90 minutes at room temperature, the oligomer was washed with NMP, cleaved from the synthesis resin, and worked up as described above. The product was analyzed by MALDI-TOF mass spectrometry (MALDI-TOF) and HPLC. The desired product included a 3'-acetyl group and was capped at the 5'-end with piperazine, which was used for conjugation, as described below and shown in FIG. 4A.

The linker reagent, N-(γ-maleimidobutyryloxy)succinimide ester (GMBS), was dissolved in 50 µl of DMSO, and the solution was added to the oligomer (2-5 mM) in sodium phosphate buffer (50 mM, pH 7.2) at a 1:2 PMO/GMBS molar ratio. The mixture was stirred at room temperature in the dark for 30 minutes, and the product was precipitated using a 30-fold excess of acetone, then redissolved in water. The PMO-GMBS adduct was lyophilized and analyzed by MALDI-TOF and HPLC. The adduct was then dissolved in phosphate buffer (50 mM, pH 6.5, 5 mM EDTA) containing 20% $CH_3CN$, and the transport peptide was added, at a 2:1 peptide to PMO molar ratio (based on a PMO concentration as determined by its absorbance at 260 nm). The reaction was stirred at room temperature in the dark for 2 hours. The conjugate was purified first through a CM-Sepharose (Sigma, St. Louis, Mo.) cationic exchange column, to remove unconjugated PMO, then through a reverse phase column (HLB column, Waters, Milford, Mass.). The conjugate was lyophilized and analyzed by MALDI-TOF and capillary electrophoresis (CE). The final product contained about 70% material corresponding to the full length PMO conjugated to the transport peptide, with the balance composed of shorter sequence conjugates, a small amount of unconjugated PMO, both full length and fragments, and a very small amount (about 2%) of unconjugated peptide. The concentration determination used for all experiments was based on the total absorbance at 260 nm, including all shorter PMO sequences in the sample.

Example 4

3'-Attachment of Transport Peptide

A PMO having a free secondary amine (ring nitrogen of morpholine) at the 3'-end (see FIG. 4B) was dissolved in 100 mM sodium phosphate buffer, pH 7.2, to make a 2-5 mM solution. The linking reagent, GMBS, was dissolved in 100 µl of DMSO and added to the PMO solution at a PMO/GMBS ratio of 1:2. The mixture was stirred at room temperature in the dark for 30 min, then passed through a P2 (Biorad) gel filtration column to remove the excess GMBS and reaction by-products.

The GMBS-PMO adduct was lyophilized and re-dissolved in 50 mM phosphate buffer, pH 6.5, to make a 2-5 mM solution. A transport peptide, represented by T-SH in FIG. 4B, was added to the GMBS-PMO solution at a molar ratio of 2:1 peptide to PMO. (The thiol-SH is the side chain of a single cysteine residue.) The reaction mixture was stirred at room temperature for 2 hours or at 4° C. overnight. The conjugate was purified by passing through Excellulose gel filtration column (Pierce Chemical) to remove excess peptide, then through a cation exchange CM-Sepharose column (Sigma) to remove unconjugated PMO, and finally through an Amberchrom reverse phase column (Rohm and Haas) to remove salt. The conjugate was lyophilized and characterized by MS and HPLC.

Example 5

Preparation of a PMO-Peptide Conjugate Having a Cleavable Linker

The procedure of Example 3 or Example 4 is repeated, employing N-succinimidyl 3-(2-pyridyldithio) propionate (SPDP) or succinimidyloxycarbonyl α-methyl-α-(2-pyridyldithio) toluene (SMPT) as linking reagent (see FIG. 4C), in place of GMBS.

Example 6

Uptake of Labeled PMO-Peptide Conjugates

HeLa cells were stably transfected with plasmid pLuc/705, which has a luciferase gene interrupted by a human β-globin intron mutated at nucleotide 705, thus causing incorrect splicing (Kang et al., 1998; Kole et al., 2001; Yan et al., 2002). Because the mis-spliced transcripts do not produce functional reporter proteins, no reporter signals are observed unless wild-type splicing is induced with a splice-correcting oligomer. An antisense oligomer targeting the 705 splice site (having SEQ ID NO: 1, also designated "PMO 705"), when delivered effectively, corrects splicing and allows luciferase expression.

This assay measures the ability of steric blocking oligomers to enter cells and nuclei, block incorrect splicing of pre-mRNA, and thus cause expression of a reporter gene. It avoids the confusion of cytotoxicity with activity that can affect down-regulation assays, as cells must be able to carry out RNA processing and translation to produce a signal. Because oligomers must enter cells and cell nuclei to produce a signal in the assay, it is very useful for measuring uptake and effectiveness of delivery moieties. In addition, because no or very little signal is present before splice correction, the assay has a favorable signal-to-noise ratios. These unambiguously positive readouts allow convenient quantitative comparisons between the effects of different transporters on oligomer delivery (Moulton et al., 2003, Astriab-Fisher et al., 2002).

The time course of the uptake of various transporter-PMO-fluorescein conjugates, as described above, in HeLa pLuc/705 cells was studied by fluorescence spectroscopy. Experiments were generally run in triplicate. According to the general procedure, culture medium containing the test substance at a specified concentration was added to HeLa pLuc/705 cells plated in a 48-well plate. After incubation, at each time point, the cells were washed with PBS three times, and the cell lysate was collected as described under "Fluorometry", above. The amount of functional luciferase produced was determined by mixing 30 µl of cell lysate and 50 µl of Luciferase Assay Reagent (LAR) (Promega, Wis.) and measuring the light production using a Flx 800 microplate fluorescence/luminesence reader (Bio-tek, Vermont). The relative light units were normalized to µg of protein determined by the bicinchoninic acid (BCA) method, following the manufacturer's procedure (Pierce, Ill.).

Example 7

Preparation of PMO Having Modified Intersubunit Linkages

A. Preparation of $Cl_2P(O)NH—(CH_2)_n—NH—C(=NH—NH_2$

A suspension containing 0.1 mole of $RNH_2.HCl$, where $R=—(CH_2)_n—NH—C(=NH)—NH_2$ (e.g. 2-aminoethyl-guanidine hydrochloride, where n=2), in 0.2 mol of phosphorous oxychloride ($POCl_3$) is refluxed for 12 hours and then distilled under reduced pressure to give the N-substituted dichlorophosphoramide.

B. Preparation of Activated Morpholino Subunit

One mmol of a 5'-hydroxyl subunit, base-protected and tritylated on the morpholino nitrogen (Structure 1, FIG. 20), prepared by standard methods (see e.g. U.S. Pat. No. 5,378,841) is dissolved in 5 ml of dichloromethane. Six mmol of N-ethylmorpholine and 2 mmol of $Cl_2P(O)NH—(CH_2)_n—NH—C(=NH)—NH_2$, prepared as described above, are added, followed by 0.5 mmol N-methylimidazole. When the reaction is complete as assessed by thin layer chromatography, the reaction mixture is washed with aqueous $NaH_2PO_4$ and concentrated. The residue is fractionated on a silica gel column, eluting with 1:4 acetone/chloroform, to give the activated subunit (Structure 2, FIG. 20).

C. Oligomerization

The activated monomer 2 is reacted with a 5'-O-support-bound subunit to give the support-bound dimer 3. The dimer is detritylated and reacted in a similar manner with further activated subunits prepared in the manner described above.

Example 8

Peptide Conjugated PMOs Exhibit Enhanced Steric Blocking Properties in Cell-Free Translation Reactions Compared to Unconjugated PMO To investigate antisense activity of conjugates in a manner independent of cellular transport, peptide conjugated and unconjugated PMO were tested in a cell free translation system for their ability to sterically block translation of a downstream reporter gene.

Figure 29:
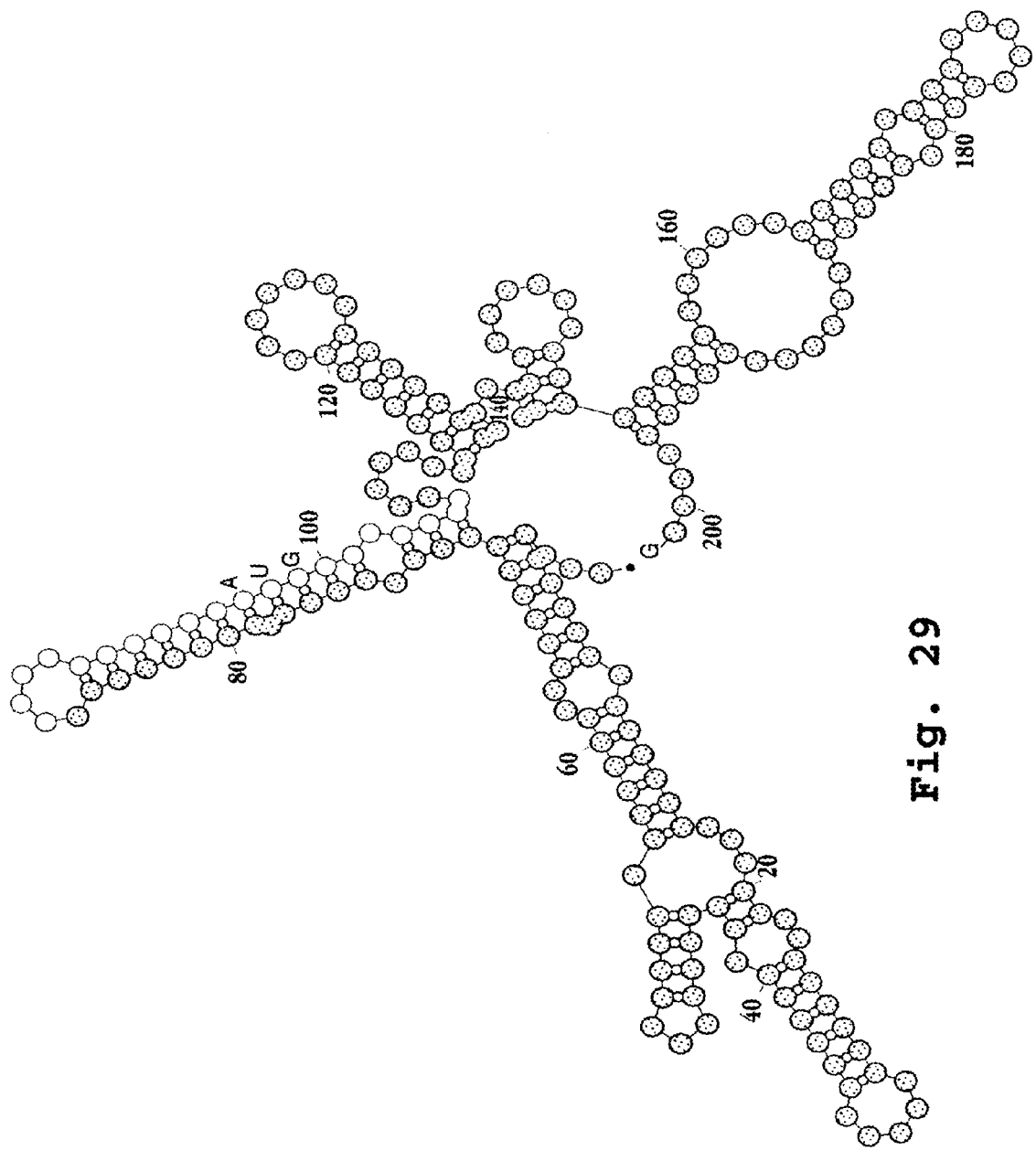
FIG. 29 shows the computer-predicted RNA secondary structure that surrounds the Dengue virus translational start codon and the target of the DEN AUG antisense PMO (highlighted, nucleotides 87-106). The AUG start codon is at nucleotides 97-99.

The effect of various antisense PMOs and PMO peptide conjugates on cell free in vitro translation of RNA, transcribed in vitro from plasmids containing various viral nucleotide sequences fused directly upstream of the coding region for firefly luciferase (fLUC), was measured in a rabbit reticulocyte lysate (RRL) system. As shown in FIGS. 21-23, conjugation of $R_9F_2$ (SEQ ID NO: 13) to PMOs increased effectiveness of the antisense PMOs by between 10-500 fold, based on the concentration required to achieve 50% inhibition of target expression. FIGS. 21-23 represent the results of these analyses using three different regions of the Dengue type 2 virus fused to the FLUC gene, as described above under Materials and Methods. The region of Dengue viral RNA genome used in the pDCLD construct is known to have a extensive secondary structure (Khromykh, Kondratieva et al. 2003), as shown in FIG. 29.

A plasmid construct with a 30 base pair region surrounding the ATG start codon of the human c-myc gene was placed in frame with the amino acid coding sequences of the fLUC gene (c-myc:fLUC). A PMO targeting this region of c-myc, AVI-4126, is listed as SEQ ID NO: 5. FIG. 28 shows the enhanced antisense effect that conjugation of the (RAhxR)$_4$ (SEQ ID NO: 34) peptide conveys to the c-myc PMO in the in vitro RRL translation system.

Results were also obtained targeting a sequence of MHV that surrounds the start codon of the 1ab gene (Neuman, B. W. et al., *J. Virol.* (2004), in press). In all the above described cases, $R_9F_2$ conjugation enhanced the antisense effectiveness of the PMO compared to unconjugated PMO by as much as 500 fold.

Example 9

Figure 24:
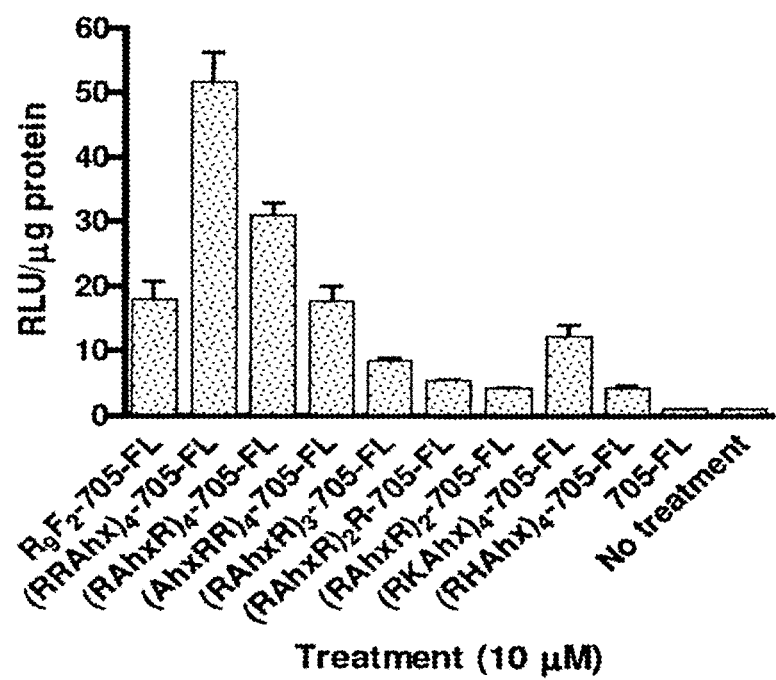
FIG. 24 shows the level of luciferase production observed (RLU per microgram of protein) in HeLa pLuc/705 cells after 24 hours treatment with 10 μM of each of the following: the PMO (705-FL) (SEQ ID NO: 1) conjugated to $R_9F_2$ (SEQ ID NO.:13), (RRAhx)$_4$ (SEQ ID NO.:33), (RAhxR)$_4$ (SEQ ID NO.:34), (AhxRR)$_4$ (SEQ ID NO.:35), (RAhxR)$_3$ (SEQ ID NO.:37), (RahxR)$_2$R (SEQ ID NO.:38), (RAhxR)$_2$ (SEQ ID NO.:39), (RKAhx)$_4$ (SEQ ID NO.:40), or (RHAhx)$_4$ (SEQ ID NO.:41).

Transport Peptides that Contain Non-Natural Amino Acids Show Enhanced Delivery into Cells, Enhanced Antisense Activity and Resistance to Enzymatic Proteolysis Cellular uptake and antisense activity was investigated, using the 705 splice correction assay described in Example 6, for several conjugates of the invention comprising PMOs conjugated to peptides containing dimers of cationic amino acids alternating with 6-aminohexonic acid (Ahx). The data are shown in FIG. 24 for a variety of such conjugates employing Ahx-containing transport peptides (SEQ ID NOs: 33-35 and 37-41). FIG. 24 shows the level of luciferase production in HeLa pLuc/705 cells after 24 hours treatment with each of the following: the PMO (705-FL, SEQ ID NO:1) conjugated to $R_9F_2$ (SEQ ID NO:13), (RRAhx)$_4$ (SEQ ID NO:33), (RAhxR)$_4$ (SEQ ID NO:34), (AhxRR)$_4$ (SEQ ID NO:35), (RAhxR)$_3$ (SEQ ID NO:37), (RahxR)$_2$R (SEQ ID NO:38), (RAhxR)$_2$ (SEQ ID NO:39), (RKAhx)$_4$ (SEQ ID NO:40), or (RHAhx)$_4$ (SEQ ID NO:41). It was observed that Ahx-containing transport peptides having at least eight arginine residues performed as well or better than $R_9F_2$ (SEQ ID NO: 13) in this assay.

The protease sensitivity of the transport peptides was also investigated, as follows. Each of the peptide-PMO conjugates $R_9F_2$-705-FL (SEQ ID NO.:13-SEQ ID NO: 1) and (RAhxR)$_4$-705-FL (SEQ ID NO.:34-SEQ ID NO: 1) was mixed with Proteinase K in 100 µl of 50 mM Tris 5 mM $CaCl_2$ buffer. The sample was incubated at 37° C. for 5 minutes or, in a separate analysis, 2 hours, then placed onto dry ice until analysis by MALDI-TOF mass spectroscopy. The results are shown in FIGS. 25 and 26, respectively.

Figure 25A:
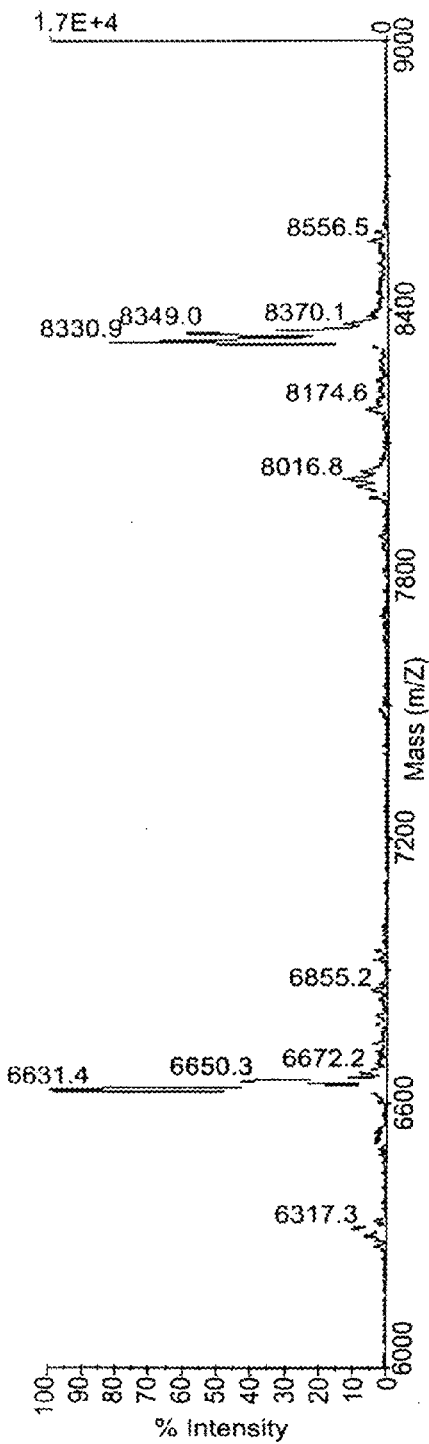
Figure 25B:
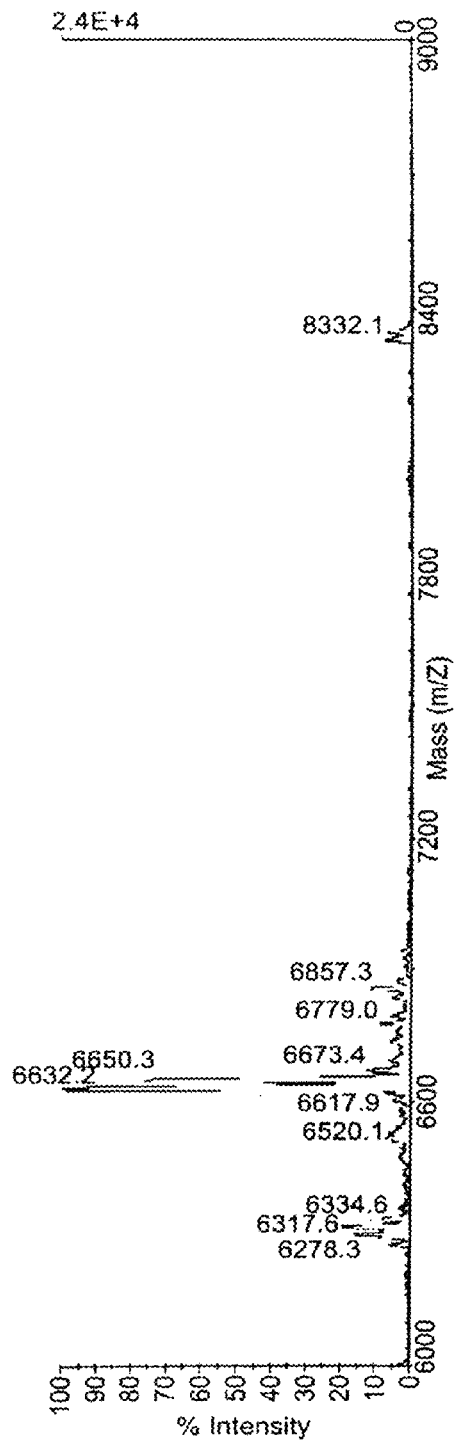

FIG. 25 shows that the transport peptide containing all natural amino acids, $R_9F_2$-C(SEQ ID NO.:43) (MW peak at 8331), was not resistant to proteinase K degradation, as it rapidly converted to the peptide-free PMO (MW peak at 6632). The $R_9F_2$-C-PMO (SEQ ID NO.:43-PMO) conjugate was also sensitive to degradation by trypsin (data not shown). FIG. 26 shows that the transport peptide containing Ahx, (RAhxR)$_4$ (SEQ ID NO: 34) (MW peak at 8332), was resistant to proteinase K degradation.

Example 10

Distribution and Bioavailability In Vivo of Peptide Conjugated PMO Compared to Unconjugated PMO Tissue culture results from a variety of experimental systems clearly demonstrate that the transport peptides described in the present invention enhance delivery to intracellular compartments including the cytoplasm and nucleus. To extend these observations to an in vivo system, a comparative analysis of PMO and peptide conjugated PMO uptake in spleen and lymph node cells was performed in mice.

Nine month old female Y10A mice (F1 of B10.A and A.B1; two mice per treatment) were injected intravenously (tail vein) with 0.5 ml of PBS containing 150 ug of a 3'-fluoresceinated PMO (scrambled sequence DSscr, 5'-AGT CTC GAC TTG CTA CCT CA-3'-FL; SEQ ID NO: 10) or the same PMO conjugated to $R_5F_2R_4$ (SEQ ID NO:20) through a cysteine linker at the 5' terminus ($R_5F_2R_4$-C-DSscr-FL) (SEQ ID NO 52-SEQ ID NO: 10). After 24 hours the mice were sacrificed, the spleens and four lymph nodes from each mouse were taken, and single cell suspensions were prepared and analyzed unstained for fluorescence by flow cytometry. The cells were gated for lymphocytes by forward/side scatter.

Figure 27:
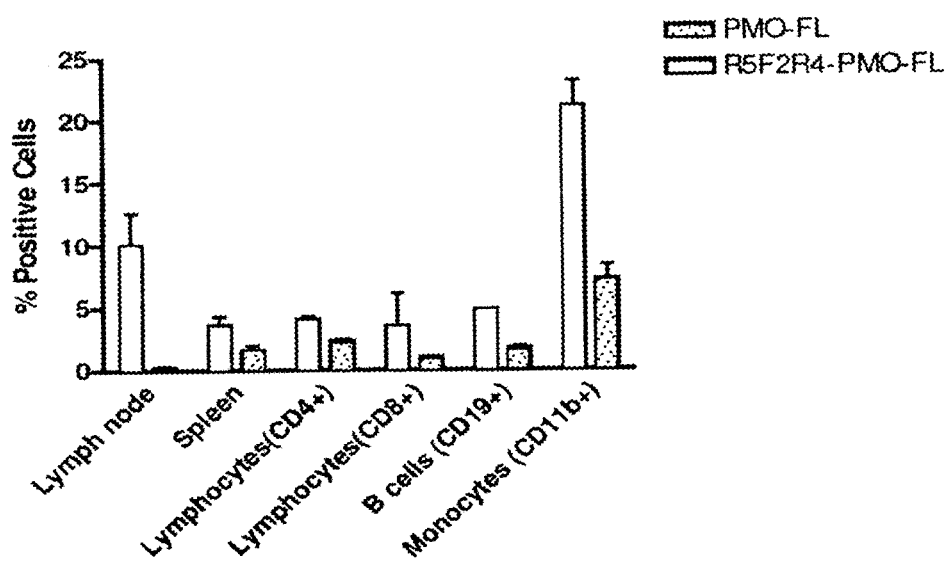
FIG. 27 shows the in vivo bioavailability and relative intracellular delivery of unconjugated and peptide conjugated, fluorescein-labeled PMO in mouse lymph node and spleen cells and subpopulations of cells from those tissues.

FIG. 27 shows that cells from both the spleens and lymph nodes had substantially higher uptake of the peptide conjugated PMO ($R_5F_2R_4$-PMO-FL) (SEQ ID NO: 20-SEQ ID NO: 1) as compared to unconjugated PMO (PMO-FL) (SEQ ID NO: 1). In addition, splenocytes were stained for different subpopulations of lymphocytes by specific cell surface markers (CD4 and CD8 for lymphocytes, CD19 for B-cells and CD11b for monocytes/macrophages). Flow cytometric analysis of the stained lymphocytes for fluorescence of the fluorescein-labeled PMO was performed. All these subpopulations demonstrated enhanced uptake of the peptide conjugated PMO compared to unconjugated PMO, as shown in FIG. 27.

The effect of multiple injections of peptide conjugated PMO on the relative uptake and residence time in vivo was analyzed as follows. Nine month old, female Y10A mice (n=3) were injected intravenously (tail vein) with 150 µg $R_5F_2R_4$-C-DSscr-FL (SEQ ID NO: 52-SEQ ID NO: 10) on days 0, 3, 5, and 7. At 11 days post injection, mice were sacrificed and single cell suspensions prepared from the spleens and four lymph nodes of each mouse. Unstained flow cytometric analysis of both cell preparations were performed as described above. A substantial percentage of both splenocytes (6.6%±2.6) and lymphocytes (4.3%+0.7) were positive for $R_5F_2R_4$-C-DSscr-FL (SEQ ID NO: 52-SEQ ID NO: 10) uptake.

SEQUENCE LISTING TABLE

| Designation | Sequence (5' to 3' or N-terminal to C-terminal) | SEQ ID NO: |
|---|---|---|
| 705 | 5'- CCT CTT ACC TCA GTT ACA-acetyl-3' | 1 |
| 705-FL | 5'- CCT CTT ACC TCA GTT ACA-fluorescein-3' | 1 |
| $705_{2MM}$ | 5'- CCT CTT A<u>A</u>C TC<u>C</u> GTT ACA-acetyl-3' | 2 |
| $705_{4MM}$ | 5'- CCT <u>A</u>TT <u>A</u>AC TC<u>C</u> GTT <u>C</u>CA-acetyl-3' | 3 |
| $705_{SCR}$ | 5'- CTC TCT CAC CAT TGA CAT-acetyl-3' | 4 |
| c-myc | 5'- ACG TTG AGG GGC ATC GTC GC-acetyl-3' | 5 |
| DEN5'CS | 5'- CGT TTC AGC ATA TTG AAA GG-3' | 6 |
| DEN3'CS | 5'- CCC AGC GTC AAT ATG CTG-3' | 7 |
| DEN AUG | 5'- GGT TAT TCA TCA GAG ATC TG-3' | 8 |
| MHV 1ab | 5'- GCC CAT CTT TGC CAT TAT GC-3' | 9 |
| DSscr | 5'-AGT CTC GAC TTG CTA CCT CA-3' | 10 |
| pTat | CYGRKKRRQRRR | 11 |
| rTat | RRRQRRKKR | 12 |
| $R_9F_2$ | RRRRRRRRRFF | 13 |
| 2d-$R_9F_2$ | $_DR_D$RRRRRRRRFF (mixed isomer) | 14 |
| D-$R_9F_2$ | $_DR_DR_DR_DR_DR_DR_DR_DR_DR_DF_DF_D$ (D-isomer) | 15 |
| $R_9CF_2$ | RRRRRRRRRCFF | 16 |
| $R_8CF_2R$ | RRRRRRRRCFFR | 17 |
| $R_6CF_2R_3$ | RRRRRRCFFRRR | 18 |
| $R_5FCFR_4$ | RRRRRFCFRRRR | 19 |
| $R_5F_2R_4$ | RRRRRFFRRRR | 20 |
| $R_4CF_2R_5$ | RRRRCFFRRRRR | 21 |
| $R_2CF_2R_7$ | RRCFFRRRRRRR | 22 |
| $CF_2R_9$ | CFFRRRRRRRRR | 23 |
| $CR_9F_2$ | CRRRRRRRRRFF | 24 |
| $F_2R_9$ | FFRRRRRRRRR | 25 |
| $R_5F_2CF_2R_4$ | RRRRRFFCFFRRRR | 26 |

SEQUENCE LISTING TABLE

| Designation | Sequence (5' to 3' or N-terminal to C-terminal) | SEQ ID NO: |
|---|---|---|
| $R_9I_2$ | RRRRRRRRRII | 27 |
| $R_8F_3$ | RRRRRRRRFFF | 28 |
| $R_9F_4$ | RRRRRRRRRFFFF | 29 |
| $R_8F_2$ | RRRRRRRRFF | 30 |
| $R_6F_2$ | RRRRRRFF | 31 |
| $R_5F_2$ | RRRRRFF | 32 |
| $(RRAhx)_4$ | RRAhxRRAhxRRAhxRRAhx | 33 |
| $(RAhxR)_4$ | RAhxRRAhxRRAhxRRAhxR | 34 |
| $(AhxRR)_4$ | AhxRRAhxRRAhxRRAhxRR | 35 |
| $(RAhx)_6$ | RAhxRAhxRAhxRAhxRAhxRAhx | 36 |
| $(RAhxR)_3$ | RAhxRRAhxRRAhxR | 37 |
| $(RAhxR)_2R$ | RAhxRRAhxRR | 38 |
| $(RAhxR)_2$ | RAhxRRAhxR | 39 |
| $(RKAhx)_4$ | RKAhxRKAhxRKAhxRKAhx | 40 |
| $(RHAhx)_4$ | RHAhxRHAhxRHAhxRHAhx | 41 |
| human c-myc ATG region | AGCCTCCCGCGACGATGCCCCTCAACGTTA | 42 |

It is claimed:

1. A peptide-nucleic acid analog conjugate comprising:
   i) a carrier peptide consisting of from ten to fifteen subunits connected by amide bonds, wherein each subunit is selected from X and Y subunits, including from eight to thirteen X subunits and from two to four contiguous Y subunits;
   ii) a nucleic acid analog comprising a substantially uncharged backbone and a targeting base sequence; and
   iii) a linker consisting of one or more linker subunits connected by amide bonds, and optionally a piperazine moiety; and
   iv) a covalent attachment between the nucleic acid analog and the carrier peptide, the covalent attachment consisting of amide bonds to the linker,
   wherein:
   (a) each X subunit is independently an amino acid subunit comprising a side chain of the structure $R^1N=C(NH_2)R^2$, where $R^1$ is H or R; $R^2$ is R, $NH_2$, NHR, or $NR_2$, where R is lower alkyl or lower alkenyl and optionally comprises oxygen or nitrogen or $R^1$ and $R^2$ may together form a ring; and wherein the side chain is linked to the amino acid via $R^1$ or R2;
   (b) each Y subunit is independently a hydrophobic amino acid comprising a substituted or unsubstituted alkyl, alkenyl, alkynyl, aryl or aralkyl side chain, wherein the alkyl, alkenyl or alkynyl side chain includes at most one heteroatom for every six carbon atoms; and
   (c) each linker subunit is of the formula —C(O)—$(CH_2)_n$—NH—, wherein n is an integer from 2 to 7.

2. The peptide-nucleic acid analog conjugate of claim 1, wherein the linker comprises a β-alanine subunit, a 6-aminohexanoic acid subunit or combinations thereof.

3. The peptide-nucleic acid analog conjugate of claim 1, wherein each Y subunit is phenylalanine.

4. The peptide-nucleic acid analog conjugate of claim 1, wherein each X subunit is arginine.

5. The peptide-nucleic acid analog conjugate of claim 1, wherein the carrier peptide comprises the sequence identified as SEQ ID NO: 13.

6. The peptide-nucleic acid analog conjugate of claim 1, wherein the carrier peptide comprises the sequence identified as SEQ ID NO: 20.

7. The peptide-nucleic acid analog conjugate of claim 1, wherein the nucleic acid analog comprises a morpholino nucleic acid analog, the morpholino nucleic acid analog comprising morpholino subunits linked by phosphorus-containing linkages, the phosphorus-containing linkages linking the morpholino nitrogen of one morpholino subunit to an exocyclic carbon at the morpholino 3-position of an adjacent morpholino subunit.

8. The peptide-nucleic acid analog conjugate of claim 7, wherein the morpholino subunits are linked by phosphorous-containing linkages in accordance with the structure:

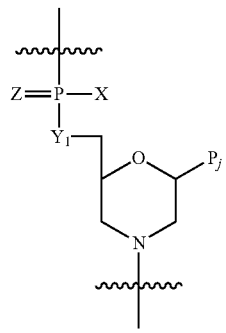

wherein:
Y$_i$ is O;
Z is O;
X is alkyl, alkoxy, thioalkoxy or alkyl amino; and
Pj is a purine or pyrimidine base-pairing moiety effective to bind to a base in a polynucleotide by base-specific hydrogen bonding.

9. The peptide-nucleic acid analog conjugate of claim 8, wherein X is dimethylamino.

10. The peptide-nucleic acid analog conjugate of claim 1, wherein the carrier peptide is attached to the 5' terminus or the 3' terminus of the nucleic acid analog.

11. The peptide-nucleic acid analog conjugate of claim 1, wherein the targeting base sequence of the nucleic acid analog is targeted to an antisense target in a polynucleotide, wherein the antisense target is a splice site in a pre-mRNA, a translation start site in an mRNA or a cis-acting element in a viral genome.

12. The peptide-nucleic acid analog conjugate of claim 1, wherein the carrier peptide comprises two Y subunits.

13. The peptide-nucleic acid analog conjugate of claim 1, wherein the carrier peptide comprises the sequence identified as SEQ ID NO: 13, SEQ ID NO: 14, SEQ ID NO: 15, SEQ ID NO: 16, SEQ ID NO: 17, SEQ ID NO: 18, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29 or SEQ ID NO: 30.

14. The peptide-nucleic acid analog conjugate of claim 1, wherein the carrier peptide consists of the sequence identified as SEQ ID NO: 13, SEQ ID NO: 14, SEQ ID NO: 15, SEQ ID NO: 16, SEQ ID NO: 17, SEQ ID NO: 18, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29 or SEQ ID NO: 30.

15. The peptide-nucleic acid analog conjugate of claim 1, wherein the carrier peptide comprises the sequence identified as SEQ ID NO: 20.

16. The peptide-nucleic acid analog conjugate of claim 10, wherein the carrier peptide is attached to the 5' terminus of the nucleic acid analog.

17. The peptide nucleic-acid analog conjugate of claim 16, wherein the carrier peptide is attached to the 5' terminus of the nucleic acid analog via a piperazinyl moiety having the following structure:

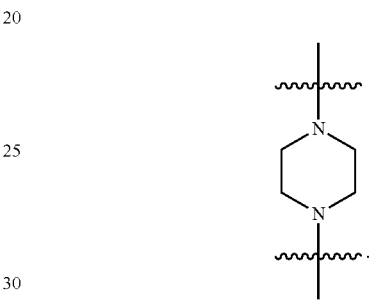

18. A peptide moiety comprising an amino acid sequence selected from one of SEQ ID NOS: 13-41, and a linker covalently bound to the carboxy terminus of the peptide moiety consisting of one or more linker subunits of the formula —C(O)(CH$_2$)$_n$NH—, wherein n is an integer from 2 to 7.

19. The peptide moiety of claim 18, wherein the amino acid sequence is as SEQ ID NO: 13.

20. A peptide moiety consisting of an amino acid sequence selected from one of SEQ ID NOS: 13-41, and a linker covalently bound to the carboxy terminus of the peptide moiety consisting of one or more linker subunits of the formula —C(O)(CH$_2$)$_n$NH—, wherein n is an integer from 2 to 7.

21. The peptide moiety of claim 20, wherein the amino acid is SEQ ID NO: 13.

22. The peptide-nucleic acid analog conjugate of claim 17, wherein the nucleic acid analog comprises a morpholino nucleic acid analog, the morpholino nucleic acid analog comprising morpholino subunits linked by phosphorus-containing linkages, the phosphorus-containing linkages linking the morpholino nitrogen of one morpholino subunit to an exocyclic carbon at the morpholino 3'-position of an adjacent morpholino subunit.

* * * * *

SEQUENCE LISTING

<160> NUMBER OF SEQ ID NOS: 52

<210> SEQ ID NO 1
<211> LENGTH: 18
<212> TYPE: DNA
<213> ORGANISM: Artificial
<220> FEATURE:
<223> OTHER INFORMATION: synthetic oligomer

<400> SEQUENCE: 1
cctcttacct cagttaca                                            18

<210> SEQ ID NO 2
<211> LENGTH: 18
<212> TYPE: DNA
<213> ORGANISM: Artificial
<220> FEATURE:
<223> OTHER INFORMATION: synthetic oligomer

<400> SEQUENCE: 2
cctcttaact ccgttaca                                            18

<210> SEQ ID NO 3
<211> LENGTH: 18
<212> TYPE: DNA
<213> ORGANISM: Artificial
<220> FEATURE:
<223> OTHER INFORMATION: synthetic oligomer

<400> SEQUENCE: 3
cctattaact ccgttcca                                            18

<210> SEQ ID NO 4
<211> LENGTH: 18
<212> TYPE: DNA
<213> ORGANISM: Artificial
<220> FEATURE:
<223> OTHER INFORMATION: synthetic oligomer

<400> SEQUENCE: 4
ctctctcacc attgacat                                                18

<210> SEQ ID NO 5
<211> LENGTH: 20
<212> TYPE: DNA
<213> ORGANISM: Artificial
<220> FEATURE:
<223> OTHER INFORMATION: synthetic oligomer

<400> SEQUENCE: 5
acgttgaggg gcatcgtcgc                                              20

<210> SEQ ID NO 6
<211> LENGTH: 20
<212> TYPE: DNA
<213> ORGANISM: Artificial
<220> FEATURE:
<223> OTHER INFORMATION: synthetic oligomer

<400> SEQUENCE: 6
cgtttcagca tattgaaagg                                              20

<210> SEQ ID NO 7
<211> LENGTH: 18
<212> TYPE: DNA
<213> ORGANISM: Artificial
<220> FEATURE:
<223> OTHER INFORMATION: synthetic oligomer

<400> SEQUENCE: 7
cccagcgtca atatgctg                                                18

<210> SEQ ID NO 8
<211> LENGTH: 20
<212> TYPE: DNA
<213> ORGANISM: Artificial
<220> FEATURE:
<223> OTHER INFORMATION: synthetic oligomer

<400> SEQUENCE: 8
ggttattcat cagagatctg                                              20

<210> SEQ ID NO 9
<211> LENGTH: 20
<212> TYPE: DNA
<213> ORGANISM: Artificial
<220> FEATURE:
<223> OTHER INFORMATION: synthetic oligomer

<400> SEQUENCE: 9
gcccatcttt gccattatgc                                              20

<210> SEQ ID NO 10
<211> LENGTH: 20
<212> TYPE: DNA
<213> ORGANISM: Artificial
<220> FEATURE:

```
<223> OTHER INFORMATION: synthetic oligomer

<400> SEQUENCE: 10
agtctcgact tgctacctca                                               20

<210> SEQ ID NO 11
<211> LENGTH: 12
<212> TYPE: PRT
<213> ORGANISM: Artificial
<220> FEATURE:
<223> OTHER INFORMATION: synthetic tranport peptide

<400> SEQUENCE: 11

Cys Tyr Gly Arg Lys Lys Arg Arg Gln Arg Arg Arg
1               5                   10

<210> SEQ ID NO 12
<211> LENGTH: 9
<212> TYPE: PRT
<213> ORGANISM: Artificial
<220> FEATURE:
<223> OTHER INFORMATION: synthetic transport peptide

<400> SEQUENCE: 12

Arg Arg Arg Gln Arg Arg Lys Lys Arg
1               5

<210> SEQ ID NO 13
<211> LENGTH: 11
<212> TYPE: PRT
<213> ORGANISM: Artificial
<220> FEATURE:
<223> OTHER INFORMATION: synthetic transport peptide

<400> SEQUENCE: 13

Arg Arg Arg Arg Arg Arg Arg Arg Arg Phe Phe
1               5                   10

<210> SEQ ID NO 14
<211> LENGTH: 11
<212> TYPE: PRT
<213> ORGANISM: Artificial
<220> FEATURE:
<223> OTHER INFORMATION: synthetic transport peptide

<400> SEQUENCE: 14

Arg Arg Arg Arg Arg Arg Arg Arg Arg Phe Phe
1               5                   10

<210> SEQ ID NO 15
<211> LENGTH: 11
<212> TYPE: PRT
<213> ORGANISM: Artificial
<220> FEATURE:
<223> OTHER INFORMATION: synthetic transport peptide

<400> SEQUENCE: 15

Arg Arg Arg Arg Arg Arg Arg Arg Arg Phe Phe
1               5                   10

<210> SEQ ID NO 16
<211> LENGTH: 12
<212> TYPE: PRT
<213> ORGANISM: Artificial
<220> FEATURE:
<223> OTHER INFORMATION: synthetic transport peptide
```

<400> SEQUENCE: 16

Arg Arg Arg Arg Arg Arg Arg Arg Cys Phe Phe
1               5                   10

<210> SEQ ID NO 17
<211> LENGTH: 12
<212> TYPE: PRT
<213> ORGANISM: Artificial
<220> FEATURE:
<223> OTHER INFORMATION: synthetic transport peptide

<400> SEQUENCE: 17

Arg Arg Arg Arg Arg Arg Arg Arg Cys Phe Phe Arg
1               5                   10

<210> SEQ ID NO 18
<211> LENGTH: 12
<212> TYPE: PRT
<213> ORGANISM: Artificial
<220> FEATURE:
<223> OTHER INFORMATION: synthetic transport peptide

<400> SEQUENCE: 18

Arg Arg Arg Arg Arg Arg Cys Phe Phe Arg Arg Arg
1               5                   10

<210> SEQ ID NO 19
<211> LENGTH: 12
<212> TYPE: PRT
<213> ORGANISM: Artificial
<220> FEATURE:
<223> OTHER INFORMATION: synthetic transport peptide

<400> SEQUENCE: 19

Arg Arg Arg Arg Arg Phe Cys Phe Arg Arg Arg Arg
1               5                   10

<210> SEQ ID NO 20
<211> LENGTH: 11
<212> TYPE: PRT
<213> ORGANISM: Artificial
<220> FEATURE:
<223> OTHER INFORMATION: synthetic transport peptide

<400> SEQUENCE: 20

Arg Arg Arg Arg Arg Phe Phe Arg Arg Arg Arg
1               5                   10

<210> SEQ ID NO 21
<211> LENGTH: 12
<212> TYPE: PRT
<213> ORGANISM: Artificial
<220> FEATURE:
<223> OTHER INFORMATION: synthetic transport peptide

<400> SEQUENCE: 21

Arg Arg Arg Arg Cys Phe Phe Arg Arg Arg Arg Arg
1               5                   10

<210> SEQ ID NO 22
<211> LENGTH: 12
<212> TYPE: PRT
<213> ORGANISM: Artificial
<220> FEATURE:
<223> OTHER INFORMATION: synthetic transport peptide

<400> SEQUENCE: 22

```
Arg Arg Cys Phe Phe Arg Arg Arg Arg Arg Arg
1               5                   10
```

<210> SEQ ID NO 23
<211> LENGTH: 12
<212> TYPE: PRT
<213> ORGANISM: Artificial
<220> FEATURE:
<223> OTHER INFORMATION: synthetic transport peptide

<400> SEQUENCE: 23

```
Cys Phe Phe Arg Arg Arg Arg Arg Arg Arg Arg
1               5                   10
```

<210> SEQ ID NO 24
<211> LENGTH: 12
<212> TYPE: PRT
<213> ORGANISM: Artificial
<220> FEATURE:
<223> OTHER INFORMATION: synthetic transport peptide

<400> SEQUENCE: 24

```
Cys Arg Arg Arg Arg Arg Arg Arg Arg Arg Phe Phe
1               5                   10
```

<210> SEQ ID NO 25
<211> LENGTH: 11
<212> TYPE: PRT
<213> ORGANISM: Artificial
<220> FEATURE:
<223> OTHER INFORMATION: synthetic transport peptide

<400> SEQUENCE: 25

```
Phe Phe Arg Arg Arg Arg Arg Arg Arg Arg Arg
1               5                   10
```

<210> SEQ ID NO 26
<211> LENGTH: 14
<212> TYPE: PRT
<213> ORGANISM: Artificial
<220> FEATURE:
<223> OTHER INFORMATION: synthetic transport peptide

<400> SEQUENCE: 26

```
Arg Arg Arg Arg Arg Phe Phe Cys Phe Phe Arg Arg Arg
1               5                   10
```

<210> SEQ ID NO 27
<211> LENGTH: 11
<212> TYPE: PRT
<213> ORGANISM: Artificial
<220> FEATURE:
<223> OTHER INFORMATION: synthetic transport peptide

<400> SEQUENCE: 27

```
Arg Arg Arg Arg Arg Arg Arg Arg Arg Ile Ile
1               5                   10
```

<210> SEQ ID NO 28
<211> LENGTH: 11
<212> TYPE: PRT
<213> ORGANISM: Artificial
<220> FEATURE:
<223> OTHER INFORMATION: synthetic transport peptide

<400> SEQUENCE: 28

Arg Arg Arg Arg Arg Arg Arg Arg Phe Phe Phe
1               5                   10

<210> SEQ ID NO 29
<211> LENGTH: 13
<212> TYPE: PRT
<213> ORGANISM: Artificial
<220> FEATURE:
<223> OTHER INFORMATION: synthetic transport peptide

<400> SEQUENCE: 29

Arg Arg Arg Arg Arg Arg Arg Arg Arg Phe Phe Phe Phe
1               5                   10

<210> SEQ ID NO 30
<211> LENGTH: 10
<212> TYPE: PRT
<213> ORGANISM: Artificial
<220> FEATURE:
<223> OTHER INFORMATION: synthetic transport peptide

<400> SEQUENCE: 30

Arg Arg Arg Arg Arg Arg Arg Arg Phe Phe
1               5                   10

<210> SEQ ID NO 31
<211> LENGTH: 8
<212> TYPE: PRT
<213> ORGANISM: Artificial
<220> FEATURE:
<223> OTHER INFORMATION: synthetic transport peptide

<400> SEQUENCE: 31

Arg Arg Arg Arg Arg Arg Phe Phe
1               5

<210> SEQ ID NO 32
<211> LENGTH: 7
<212> TYPE: PRT
<213> ORGANISM: Artificial
<220> FEATURE:
<223> OTHER INFORMATION: synthetic transport peptide

<400> SEQUENCE: 32

Arg Arg Arg Arg Arg Phe Phe
1               5

<210> SEQ ID NO 33
<211> LENGTH: 12
<212> TYPE: PRT
<213> ORGANISM: Artificial
<220> FEATURE:
<223> OTHER INFORMATION: synthetic transport peptide
<220> FEATURE:
<221> NAME/KEY: misc_feature
<222> LOCATION: 3, 6, 9, 12
<223> OTHER INFORMATION: Xaa = 6-aminohexanoic acid

<400> SEQUENCE: 33

Arg Arg Xaa Arg Arg Xaa Arg Arg Xaa Arg Arg Xaa
1               5                   10

<210> SEQ ID NO 34
<211> LENGTH: 12
<212> TYPE: PRT
<213> ORGANISM: Artificial
<220> FEATURE:
<223> OTHER INFORMATION: synthetic transport peptide

```
<220> FEATURE:
<221> NAME/KEY: misc_feature
<222> LOCATION: 2, 5, 8, 11
<223> OTHER INFORMATION: Xaa = 6-aminohexanoic acid

<400> SEQUENCE: 34

Arg Xaa Arg Arg Xaa Arg Arg Xaa Arg Arg Xaa Arg
1               5                   10

<210> SEQ ID NO 35
<211> LENGTH: 12
<212> TYPE: PRT
<213> ORGANISM: Artificial
<220> FEATURE:
<223> OTHER INFORMATION: synthetic transport peptide
<220> FEATURE:
<221> NAME/KEY: misc_feature
<222> LOCATION: 1, 4, 7, 10
<223> OTHER INFORMATION: Xaa = 6-aminohexanoic acid

<400> SEQUENCE: 35

Xaa Arg Arg Xaa Arg Arg Xaa Arg Arg Xaa Arg Arg
1               5                   10

<210> SEQ ID NO 36
<211> LENGTH: 12
<212> TYPE: PRT
<213> ORGANISM: Artificial
<220> FEATURE:
<223> OTHER INFORMATION: synthetic transport peptide
<220> FEATURE:
<221> NAME/KEY: misc_feature
<222> LOCATION: 2, 4, 6, 8, 10, 12
<223> OTHER INFORMATION: Xaa = 6-aminohexanoic acid

<400> SEQUENCE: 36

Arg Xaa Arg Xaa Arg Xaa Arg Xaa Arg Xaa Arg Xaa
1               5                   10

<210> SEQ ID NO 37
<211> LENGTH: 9
<212> TYPE: PRT
<213> ORGANISM: Artificial
<220> FEATURE:
<223> OTHER INFORMATION: synthetic transport peptide
<220> FEATURE:
<221> NAME/KEY: misc_feature
<222> LOCATION: 2, 5, 8
<223> OTHER INFORMATION: Xaa = 6-aminohexanoic acid

<400> SEQUENCE: 37

Arg Xaa Arg Arg Xaa Arg Arg Xaa Arg
1               5

<210> SEQ ID NO 38
<211> LENGTH: 7
<212> TYPE: PRT
<213> ORGANISM: Artificial
<220> FEATURE:
<223> OTHER INFORMATION: synthetic transport protein
<220> FEATURE:
<221> NAME/KEY: misc_feature
<222> LOCATION: 2, 5
<223> OTHER INFORMATION: Xaa = 6-aminohexanoic acid

<400> SEQUENCE: 38

Arg Xaa Arg Arg Xaa Arg Arg
1               5
```

```
<210> SEQ ID NO 39
<211> LENGTH: 6
<212> TYPE: PRT
<213> ORGANISM: Artificial
<220> FEATURE:
<223> OTHER INFORMATION: synthetic transport peptide
<220> FEATURE:
<221> NAME/KEY: misc_feature
<222> LOCATION: 2, 5
<223> OTHER INFORMATION: Xaa = 6-aminohexanoic acid

<400> SEQUENCE: 39

Arg Xaa Arg Arg Xaa Arg
1               5

<210> SEQ ID NO 40
<211> LENGTH: 12
<212> TYPE: PRT
<213> ORGANISM: Artificial
<220> FEATURE:
<223> OTHER INFORMATION: synthetic transport peptide
<220> FEATURE:
<221> NAME/KEY: misc_feature
<222> LOCATION: 3, 6, 9, 12
<223> OTHER INFORMATION: Xaa = 6-aminohexanoic acid

<400> SEQUENCE: 40

Arg Lys Xaa Arg Lys Xaa Arg Lys Xaa Arg Lys Xaa
1               5                   10

<210> SEQ ID NO 41
<211> LENGTH: 12
<212> TYPE: PRT
<213> ORGANISM: Artificial
<220> FEATURE:
<223> OTHER INFORMATION: synthetic transport peptide
<220> FEATURE:
<221> NAME/KEY: misc_feature
<222> LOCATION: 3, 6, 9, 12
<223> OTHER INFORMATION: Xaa = 6-aminohexanoic acid

<400> SEQUENCE: 41

Arg His Xaa Arg His Xaa Arg His Xaa Arg His Xaa
1               5                   10

<210> SEQ ID NO 42
<211> LENGTH: 9
<212> TYPE: PRT
<213> ORGANISM: Artificial
<220> FEATURE:
<223> OTHER INFORMATION: synthetic transport peptide

<400> SEQUENCE: 42

Arg Lys Lys Arg Arg Gln Arg Arg Arg
1               5

<210> SEQ ID NO 43
<211> LENGTH: 12
<212> TYPE: PRT
<213> ORGANISM: Artificial
<220> FEATURE:
<223> OTHER INFORMATION: synthetic transport peptide

<400> SEQUENCE: 43

Arg Arg Arg Arg Arg Arg Arg Arg Arg Phe Phe Cys
1               5                   10

<210> SEQ ID NO 44
<211> LENGTH: 14
```

```
<212> TYPE: PRT
<213> ORGANISM: Artificial
<220> FEATURE:
<223> OTHER INFORMATION: synthetic transport peptide
<220> FEATURE:
<221> NAME/KEY: misc_feature
<222> LOCATION: 2, 5, 8, 11, 13
<223> OTHER INFORMATION: Xaa = 6-aminohexanoic acid
<220> FEATURE:
<221> NAME/KEY: misc_feature
<222> LOCATION: 14
<223> OTHER INFORMATION: Xaa = beta-Alanine

<400> SEQUENCE: 44

Arg Xaa Arg Arg Xaa Arg Arg Xaa Arg Arg Xaa Arg Xaa Xaa
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (2)...(11)
<223> OTHER INFORMATION: Xaa = non-natural variable amino acid sequence

<400> SEQUENCE: 45

Arg Xaa Arg Arg Xaa Arg Arg Xaa Arg Arg Xaa Arg
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (3)...(12)
<223> OTHER INFORMATION: Xaa = non-natural variable amino acid sequence

<400> SEQUENCE: 46

Arg Arg Xaa Arg Arg Xaa Arg Arg Xaa Arg Arg Xaa
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Synthetic transport peptide

<400> SEQUENCE: 47

Arg Arg Arg Arg Arg Arg Arg Arg Arg Cys
1               5                   10

<210> SEQ ID NO 48
<211> LENGTH: 30
<212> TYPE: DNA
<213> ORGANISM: Artificial Sequence
<220> FEATURE:
<223> OTHER INFORMATION: Synthetic plasmid construct sequence

<400> SEQUENCE: 48
agcctcccgc gacgatgccc ctcaacgtta                               30

<210> SEQ ID NO 49
```

```
<211> LENGTH: 12
<212> TYPE: PRT
<213> ORGANISM: Artificial Sequence
<220> FEATURE:
<223> OTHER INFORMATION: synthetic transport peptide
<220> FEATURE:
<221> NAME/KEY: MOD_RES
<222> LOCATION: (1)...(12)
<223> OTHER INFORMATION: D-amino acids

<400> SEQUENCE: 49

Arg Arg Arg Arg Arg Arg Arg Arg Arg Phe Phe Cys
1               5                   10

<210> SEQ ID NO 50
<211> LENGTH: 10
<212> TYPE: PRT
<213> ORGANISM: Artificial Sequence
<220> FEATURE:
<223> OTHER INFORMATION: synthetic transport peptide

<400> SEQUENCE: 50

Arg Arg Arg Gln Arg Arg Lys Lys Arg Cys
1               5                   10

<210> SEQ ID NO 51
<211> LENGTH: 9
<212> TYPE: PRT
<213> ORGANISM: Artificial Sequence
<220> FEATURE:
<223> OTHER INFORMATION: synthetic transport peptide

<400> SEQUENCE: 51

Arg Arg Arg Arg Arg Arg Arg Arg Arg
1               5

<210> SEQ ID NO 52
<211> LENGTH: 12
<212> TYPE: PRT
<213> ORGANISM: Artificial Sequence
<220> FEATURE:
<223> OTHER INFORMATION: synthetic transport peptide

<400> SEQUENCE: 52

Arg Arg Arg Arg Arg Phe Phe Arg Arg Arg Arg Cys
1               5                   10
```